United States Patent
Los et al.

(10) Patent No.: US 10,787,649 B2
(45) Date of Patent: Sep. 29, 2020

(54) MALATE DEHYDROGENASES

(71) Applicant: DSM IP ASSETS B.V., Heerlen (NL)

(72) Inventors: Alrik Pieter Los, Echt (NL); Rene Marcel De Jong, Echt (NL); Remko Tsjibbe Winter, Echt (NL); Ben Den Dulk, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/316,988

(22) PCT Filed: Jul. 11, 2017

(86) PCT No.: PCT/EP2017/067318
§ 371 (c)(1),
(2) Date: Jan. 10, 2019

(87) PCT Pub. No.: WO2018/011161
PCT Pub. Date: Jan. 18, 2018

(65) Prior Publication Data
US 2019/0225947 A1    Jul. 25, 2019

(30) Foreign Application Priority Data
Jul. 13, 2016    (EP) .................................. 16179315

(51) Int. Cl.
| C12N 9/04 | (2006.01) |
| C12P 7/46 | (2006.01) |
| C12N 1/20 | (2006.01) |
| C12N 15/00 | (2006.01) |
| C12N 1/14 | (2006.01) |
| C12R 1/865 | (2006.01) |

(52) U.S. Cl.
CPC ............. *C12N 9/0006* (2013.01); *C12N 1/14* (2013.01); *C12N 15/00* (2013.01); *C12P 7/46* (2013.01); *C12R 1/865* (2013.01); *C12Y 101/01037* (2013.01)

(58) Field of Classification Search
None
See application file for complete search history.

(56) References Cited

U.S. PATENT DOCUMENTS

| 9,340,804 B2 | 5/2016 | Verwaal et al. |
| 9,689,005 B2 | 6/2017 | Verwaal et al. |
| 2011/0081694 A1 | 4/2011 | Verwaal et al. |
| 2012/0165569 A1 | 6/2012 | Verwaal et al. |
| 2012/0219999 A1 | 8/2012 | Fischer et al. |
| 2014/0031587 A1 | 1/2014 | Verwaal et al. |

FOREIGN PATENT DOCUMENTS

| EP | 2149607 A1 | 2/2010 |
| WO | 2008/144626 A1 | 11/2008 |
| WO | 2009/065778 A1 | 5/2009 |
| WO | 2014/018755 A1 | 1/2014 |
| WO | 2014/018757 A1 | 1/2014 |

OTHER PUBLICATIONS

Studer. Residue mutations and their impact on protein structure and function: detecting beneficial and pathogenic changes. Biochem. J. (2013) 449, 581-594.*
Nishiyama M. et al., "Alteration of Coenzyme Specificity of Malate Dehydrogenase from Thermus Flavus by Site-directed Mutagenesis", The Journal of Biological Chemistry, Mar. 5, 1993, pp. 4656-4660, vol. 268, No. 7.
Tomita, Takeo et al., "Structural basis for the alteration of coenzyme specificity in malate dehydrogenase mutant", Biochemical and Biophysical Research Communications, Aug. 25, 2006, pp. 502-508, vol. 347, No. 2.
Database UniProt [Online], Jan. 15, 2008, XP002765251, retrieved from EBI accession No. UNIPROT: Q4JV42 Database accession No. Q4JV42 sequence.
Database UniProt [Online], Feb. 1, 2005, XP002765252, retrieved from EBI accession No. UNIPROT:Q5NE17, Database accession No. Q5NE17 sequence.
Zelle, Rintze M. et al., "Malic acid production by *Saccharomyces cerevisiae*: engineering of pyruvate carboxylation, oxaloacetate reduction, and malate export", Applied and Environmental Microbiology, May 1, 2008, pp. 2766-2777, vol. 74, No. 9.
Steffan, Joan S. et al., "Isolation and Characterization of the Yeast Gene Encoding the MDH3 Isozyme of Malate Dehydrogenase", The Journal of Biological Chemistry, Dec. 5, 1992, pp. 24708-24715, vol. 267, No. 34.
Musrati, R. A. et al., "Malate Dehydrogenase: Distribution, Function and Properties", General Physiology and Biophysics, Jan. 1, 1998, pp. 193-210, vol. 17, No. 3.
Minarik, P. et al., "Malate Dehydrogenases—Structure and Function", General Physiology and Biophysics, Sep. 1, 2002, pp. 257-265, vol. 21.
International Search Report of International Patent Application No. PCT/EP2017/067318 dated Sep. 18, 2017.

* cited by examiner

*Primary Examiner* — Yong D Pak
(74) *Attorney, Agent, or Firm* — McBee Moore Woodward & Vanik IP, LLC

(57) ABSTRACT

The present invention relates to a recombinant host cell which is capable of producing a dicarboxylic acid and which comprises a mutant malate dehydrogenase resulting in an increased production of the dicarboxylic acid. The invention also relates to a process for producing a dicarboxylic acid, which method comprises fermenting said recombinant host cell in a suitable fermentation medium and producing the dicarboxylic acid.

19 Claims, 10 Drawing Sheets
Specification includes a Sequence Listing.

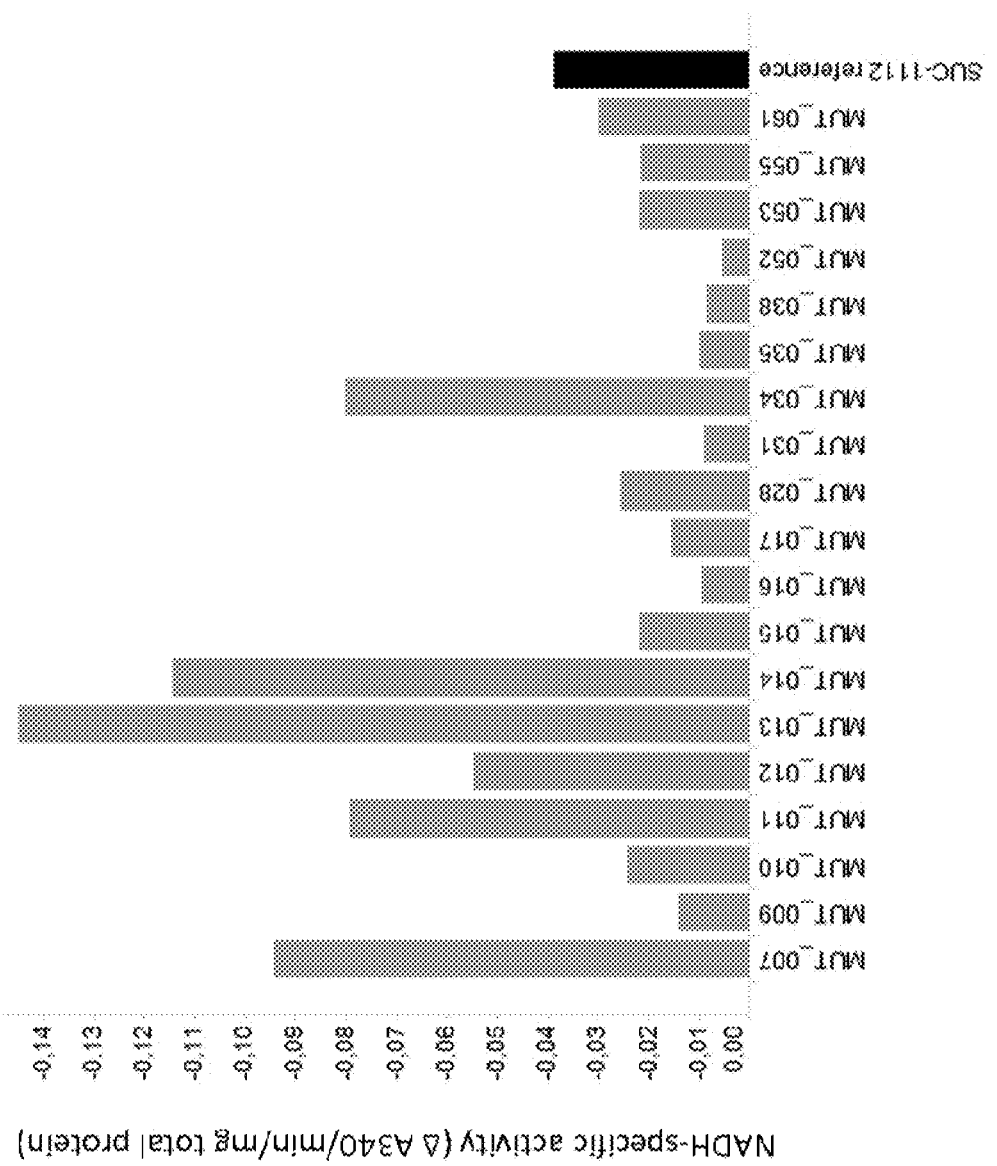

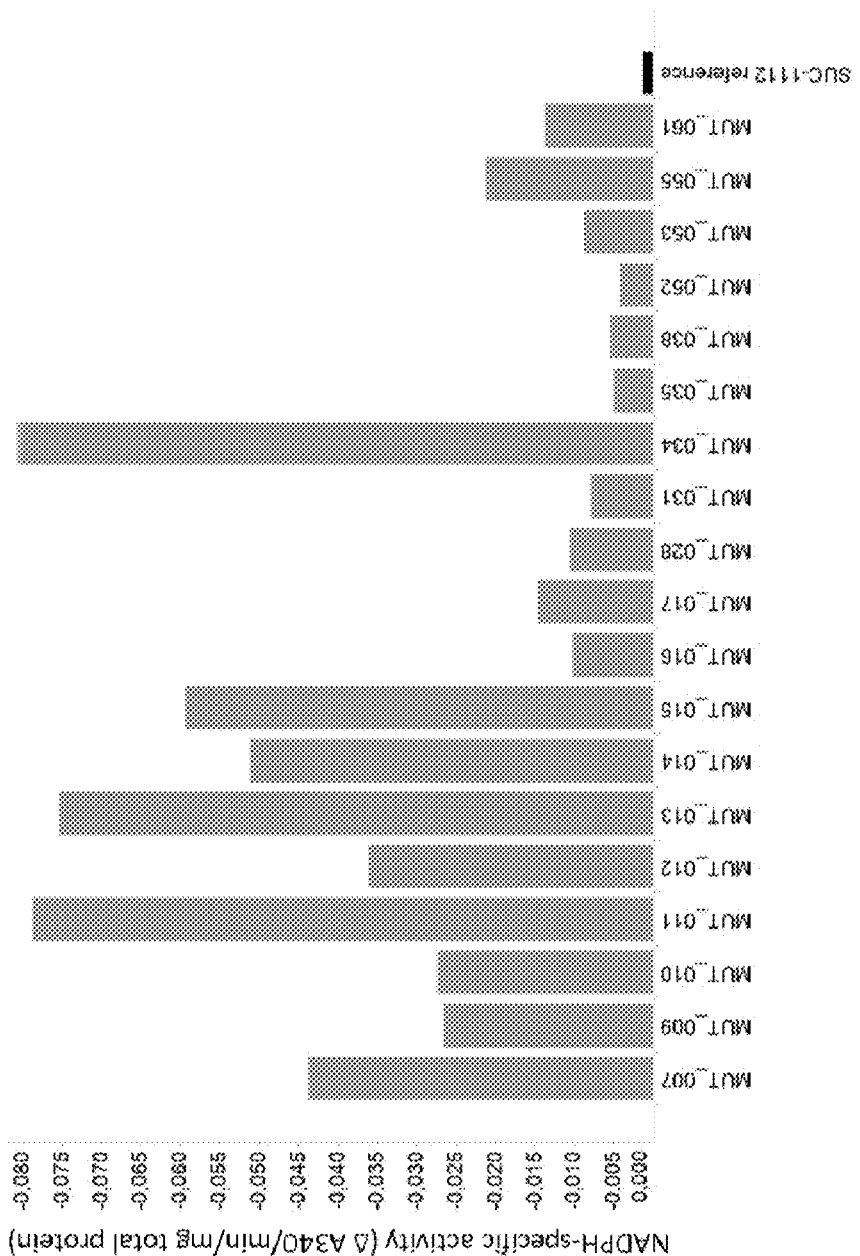

SEQUENCE LISTING

```
<160> NUMBER OF SEQ ID NOS: 67

<210> SEQ ID NO 1
<211> LENGTH: 10504
<212> TYPE: DNA
<213> ORGANISM: Artificial Sequence
<220> FEATURE:
<223> OTHER INFORMATION: nucleotide sequence of fragment 2 (Figure 2),
      which includes PEP carboxykinase from Actinobacillus succinogenes
      codon pair optimized for expression in Saccharomyces cerevisiae

<400> SEQUENCE: 1
ttgcccatcg aacgtacaag tactcctctg ttctctcctt cctttgcttt gtgcgacacc      60
taactacata gtgtttaaag attacggata tttaacttac ttagaataat gccattttt     120 tgagttataa taatcctacg ttagtgtgag cgggatttaa actgtgagga ccttaataca    180
ttcagacact tctgcggtat caccctactt attcccttcg agattatatc taggaaccca    240
```

```
tcaggttggt ggaagattac ccgttctaag acttttcagc ttcctctatt gatgttacac      300
ctggacaccc cttttctggc atccagtttt taatcttcag tggcatgtga gattctccga      360
aattaattaa agcaatcaca caattctctc ggataccacc tcggttgaaa ctgacaggtg      420
gtttgttacg catgctaatg caaaggagcc tatataccct tggctcggct gctgtaacag      480
ggaatataaa gggcagcata atttaggagt ttagtgaact tgcaacattt actattttcc      540
cttcttacgt aaatatttt cttttaatt ctaaatcaat ctttttcaat tttttgtttg       600
tattcttttc ttgcttaaat ctataactac aaaaacaca tacataaact aaaaatgact       660
gatttgaaca aattggtcaa ggaattgaat gatttgggtt tgactgacgt caaggaaatt       720
gtctacaacc catcttacga acaattattc gaagaagaaa ccaagccagg tttggaaggt       780
ttcgacaagg gtactttgac cactttaggt gctgttgctg ttgacaccgg tattttcacc       840
ggtcgttctc caaaggacaa atacattgtt tgtgatgaaa ccaccaagga caccgtctgg       900
tggaactctg aagctgccaa gaacgataac aagccaatga ctcaagaaac ctggaaatct       960
ttgagagaat tggttgccaa gcaattgtct ggtaagagat tattcgttgt tgacgctttc      1020
tgtggtgctt ctgaaaagca cagaattggt gtcagaatgg tcactgaagt tgcttggcaa      1080
gctcatttcg tcaagaacat gttcatcaga ccaactgacg aagaattgaa gaacttcaag      1140
gctgacttca ccgttttgaa tggtgccaag tgtaccaacc caaactggaa ggaacaaggt      1200
ttgaactctg aaaactttgt tgctttcaac atcactgaag gtatccaatt gattggtggt      1260
acttggtacg gtggtgaaat gaagaagggt atgttctcca tgatgaacta tttcttgcca      1320
ttgaaaggtg ttgcttccat gcactgttct gccaatgtcg gtaaggatgg tgacgttgcc      1380
atcttcttcg gtctatccgg tactggtaag accactctat ccactgaccc aaagagacaa      1440
ttgattggtg atgacgaaca cggttgggac gaatctggtg tctttaactt tgaaggtggt      1500
tgttacgcca agaccatcaa cttatctcaa gaaaacgaac cagatatcta cggtgccatc      1560
cgtcgtgatg ctttgttgga aaacgttgtt gtcagagctg acggtctgt tgacttcgac      1620 gacggttcca agactgaaaa caccagagtt tcttacccaa tctaccacat tgacaacatt      1680
gtcagacctg tttccaaggc tggtcacgct accaaggtta tcttcttgac tgctgatgct      1740
ttcggtgtct tgccacctgt ttccaaattg actccagaac aaaccgaata ctacttcttg      1800
tccggtttca ctgccaaatt ggctggtact gaaagaggtg tcactgaacc aactccaact      1860
ttctctgctt gtttcggtgc tgcttcttta tctttgcacc caatccaata cgctgatgtc      1920
ttggttgaaa gaatgaaggc ttctggtgct gaagcttact ggtcaacac cggttggaac      1980 ggtactggta agagaatctc catcaaggat accagaggta tcattgatgc tatcttggac      2040
ggttccattg aaaaggctga atgggtgaa ttgccaatct tcaacttggc cattccaaag      2100
gctttgccag gtgttgaccc agccatctta gatccaagag acacctacgc tgacaaggct      2160
caatggcaag tcaaggctga agatttggct aacagattcg tcaagaactt tgtcaaatac      2220
actgctaacc cagaagctgc caaattggtt ggtgctggtc aaaggcttaa aggagttaa      2280 aggcaaagtt ttcttttcta gagccgttcc cacaaataat tatacgtata tgcttctttt      2340
cgtttactat atatctatat ttacaagcct ttattcactg atgcaattg tttccaaata      2400 cttttttgga gatctcataa ctagatatca tgatggcgca acttggcgct atcttaatta      2460
ctctggctgc caggccgtg tagagggccg caagaccttc tgtacgccat atagtctcta      2520
agaacttgaa caagtttcta gacctattgc cgcctttcgg atcgctattg ttcctccgga      2580
```

-continued

```
tcgatgtaca caaccgactg cacccaaacg aacacaaatc ttagcattgc ccatcgaacg       2640
tacaagtact cctctgttct ctccttcctt tgctttgtgc gacacctaac tacatagtgt       2700
ttaaagatta cggatattta acttacttag aataatgcca ttttttttgag ttataataat      2760 cctacgttag tgtgagcggg atttaaactg tgaggacctt aatacattca gacacttctg      2820
cggtatcacc ctacttattc ccttcgagat tatatctagg aacccatcag gttggtggaa       2880
gattacccgt tctaagactt ttcagcttcc tctattgatg ttacacctgg acaccccttt      2940
tctggcatcc agttttttaat cttcagtggc atgtgagatt ctccgaaatt aattaaagca     3000
atcacacaat tctctcggat accacctcgg ttgaaactga caggtggttt gttacgcatg      3060
ctaatgcaaa ggagcctata tacctttggc tcggctgctg taacagggaa tataaagggc      3120
agcataattt aggagtttag tgaacttgca acatttacta ttttcccttc ttacgtaaat      3180 attttttcttt ttaattctaa atcaatcttt ttcaattttt tgtttgtatt cttttcttgc     3240
ttaaatctat aactacaaaa aacacataca taaactaaaa atgactgatt tgaacaaatt      3300
ggtcaaggaa ttgaatgatt tgggtttgac tgacgtcaag gaaattgtct acaacccatc      3360
ttacgaacaa ttattcgaag aagaaaccaa gccaggtttg aaggtttcg acaagggtac       3420 tttgaccact ttaggtgctg ttgctgttga caccggtatt ttcaccggtc gttctccaaa      3480
ggacaaatac attgtttgtg atgaaaccac caaggacacc gtctggtgga actctgaagc      3540
tgccaagaac gataacaagc caatgactca agaaacctgg aaatctttga gagaattggt     3600
tgccaagcaa ttgtctggta agagattatt cgttgttgac gctttctgtg gtgcttctga      3660
aaagcacaga attggtgtca gaatggtcac tgaagttgct tggcaagctc atttcgtcaa      3720
gaacatgttc atcagaccaa ctgacgaaga attgaagaac ttcaaggctg acttcaccgt      3780
tttgaatggt gccaagtgta ccaacccaaa ctggaaggaa caaggtttga actctgaaaa      3840
ctttgttgct ttcaacatca ctgaaggtat ccaattgatt ggtggtactt ggtacggtgg      3900
tgaaatgaag aagggtatgt ctccatgat gaactatttc ttgccattga aaggtgttgc       3960
ttccatgcac tgttctgcca atgtcggtaa ggatggtgac gttgccatct tcttcggtct      4020
atccggtact ggtaagacca ctctatccac tgacccaaag agacaattga ttggtgatga      4080
cgaacacggt tgggacgaat ctggtgtctt taactttgaa ggtggttgtt acgccaagac      4140
catcaactta tctcaagaaa acgaaccaga tatctacggt gccatccgtc gtgatgcttt      4200
gttggaaaac gttgttgtca gagctgacgg ttctgttgac ttcgacgacg gttccaagac      4260
tgaaaacacc agagtttctt acccaatcta ccacattgac aacattgtca gacctgtttc      4320
caaggctggt cacgctacca aggttatctt cttgactgct gatgctttcg gtgtcttgcc      4380 acctgttttcc aaattgactc agaacaaac cgaatactac ttcttgtccg gtttcactgc      4440
caaattggct ggtactgaaa gaggtgtcac tgaaccaact ccaactttct ctgcttgttt       4500
cggtgctgct ttcttatctt tgcacccaat ccaatacgct gatgtcttgg ttgaaagaat       4560
gaaggcttct ggtgctgaag cttacttggt caacaccggt tggaacggta ctggtaagag      4620
aatctccatc aaggatacca gaggtatcat tgatgctatc ttggacggtt ccattgaaaa      4680
ggctgaaatg ggtgaattgc caatcttcaa cttggccatt ccaaaggctt gccaggtgt       4740 tgacccagcc atcttagatc aagagacac ctacgctgac aaggctcaat ggcaagtcaa      4800
ggctgaagat ttggctaaca gattcgtcaa gaacttgtc aaatacactg ctaacccaga      4860
agctgccaaa ttggttggtg ctggtccaaa ggcttaaagg agttaaaggc aaagtttttct      4920 tttctagagc cgttcccaca aataattata cgtatatgct tcttttcgtt tactatatat      4980
```

```
ctatatttac aagcctttat tcactgatgc aatttgtttc caaatacttt tttggagatc    5040
tcataactag atatcatgat ggcgcaactt ggcgctatct taattactct ggctgccagg    5100
cccgtgtaga gggccgcaag accttctgta cgccatatag tctctaagaa cttgaacaag    5160
tttctagacc tattgccgcc tttcggatcg ctattgttcc tccggatcga tgtacacaac    5220
cgactgcacc caaacgaaca caaatcttag cattgcccat cgaacgtaca agtactcctc    5280
tgttctctcc ttcctttgct tgtgcgaca cctaactaca tagtgtttaa agattacgga     5340
tatttaactt acttagaata atgccatttt tttgagttat aataatccta cgttagtgtg    5400
agcgggattt aaactgtgag gaccttaata cattcagaca cttctgcggt atcaccctac    5460
ttattccctt cgagattata tctaggaacc catcaggttg gtggaagatt acccgttcta    5520 agactttca gcttcctcta ttgatgttac acctggacac cccttttctg gcatccagtt     5580
tttaatcttc agtggcatgt gagattctcc gaaattaatt aaagcaatca cacaattctc    5640
tcggatacca cctcggttga aactgacagg tggtttgtta cgcatgctaa tgcaaaggag    5700
cctatatacc tttggctcgg ctgctgtaac agggaatata aagggcagca taatttagga    5760
gtttagtgaa cttgcaacat ttactatttt cccttcttac gtaaatattt ttcttttaa     5820 ttctaaatca atcttttca atttttgtt tgtattcttt tcttgcttaa atctataact      5880
acaaaaaaca catacataaa ctaaaaatga ctgatttgaa caaattggtc aaggaattga    5940
atgatttggg tttgactgac gtcaaggaaa ttgtctacaa cccatcttac gaacaattat    6000
tcgaagaaga aaccaagcca ggtttggaag gtttcgacaa gggtactttg accactttag    6060
gtgctgttgc tgttgacacc ggtattttca ccggtcgttc tccaaaggac aaatacattg    6120
tttgtgatga aaccaccaag gacaccgtct ggtggaactc tgaagctgcc aagaacgata    6180
acaagccaat gactcaagaa acctggaaat ctttgagaga attggttgcc aagcaattgt    6240
ctggtaagag attattcgtt gttgacgctt tctgtggtgc ttctgaaaag cacagaattg    6300
gtgtcagaat ggtcactgaa gttgcttggc aagctcattt cgtcaagaac atgttcatca    6360
gaccaactga cgaagaattg aagaacttca aggctgactt caccgttttg aatggtgcca    6420
agtgtaccaa cccaaactgg aaggaacaag gtttgaactc tgaaaacttt gttgctttca    6480
acatcactga aggtatccaa ttgattggtg gtacttggta cggtggtgaa atgaagaagg    6540
gtatgttctc catgatgaac tatttcttgc cattgaaagg tgttgcttcc atgcactgtt    6600
ctgccaatgt cggtaaggat ggtgacgttg ccatcttctt cggtctatcc ggtactggta    6660
agaccactct atccactgac ccaaagagac aattgattgg tgatgacgaa cacggttggg    6720
acgaatctgg tgtctttaac tttgaaggtg gttgttacgc caagaccatc aacttatctc    6780
aagaaaacga accagatatc tacggtgcca tccgtcgtga tgctttgttg gaaaacgttg    6840
ttgtcagagc tgacggttct gttgacttcg acgacggttc caagactgaa aacaccagag    6900
tttcttaccc aatctaccac attgacaaca ttgtcagacc tgtttccaag gctggtcacg    6960
ctaccaaggt tatcttcttg actgctgatg ctttcggtgt cttgccacct gtttccaaat    7020
tgactccaga acaaaccgaa tactacttct tgtccggttt cactgccaaa ttggctggta    7080
ctgaaagagg tgtcactgaa ccaactccaa cttttctctgc ttgtttcggt gctgctttct    7140
tatctttgca cccaatccaa tacgctgatg tcttggttga agaatgaag gcttctggtg    7200 ctgaagctta cttggtcaac accggttgga acggtactgg taagagaatc tccatcaagg    7260
ataccagagg tatcattgat gctatcttgg acggttccat tgaaaaggct gaaatgggtg    7320
```

```
aattgccaat cttcaacttg gccattccaa aggctttgcc aggtgttgac ccagccatct    7380
tagatccaag agacacctac gctgacaagg ctcaatggca agtcaaggct gaagatttgg    7440
ctaacagatt cgtcaagaac tttgtcaaat acactgctaa cccagaagct gccaaattgg    7500
ttggtgctgg tccaaaggct taaaggagtt aaaggcaaag ttttctttc tagagccgtt     7560 cccacaaata attatacgta tatgcttctt ttcgtttact atatatctat atttacaagc    7620
ctttattcac tgatgcaatt tgtttccaaa tactttttg gagatctcat aactagatat     7680
catgatggcg caacttggcg ctatcttaat tactctggct gccaggcccg tgtagagggc    7740
cgcaagacct tctgtacgcc atatagtctc taagaacttg aacaagtttc tagacctatt    7800
gccgcctttc ggatcgctat tgttcctccg gatcgatgta cacaaccgac tgcacccaaa    7860
cgaacacaaa tcttagcatt gcccatcgaa cgtacaagta ctcctctgtt ctctccttcc    7920
tttgctttgt gcgacaccta actacatagt gtttaaagat tacggatatt taacttactt    7980
agaataatgc cattttttg agttataata atcctacgtt agtgtgagcg ggatttaaac     8040
tgtgaggacc ttaatacatt cagacacttc tgcggtatca ccctacttat tcccttcgag    8100
attatatcta ggaacccatc aggttggtgg aagattaccc gttctaagac ttttcagctt    8160
cctctattga tgttacacct ggacacccct tttctggcat ccagttttta atcttcagtg    8220
gcatgtgaga ttctccgaaa ttaattaaag caatcacaca attctctcgg ataccacctc    8280
ggttgaaact gacaggtggt ttgttacgca tgctaatgca aaggagccta tacctttg      8340 gctcggctgc tgtaacaggg aatataaagg gcagcataat ttaggagttt agtgaacttg    8400
caacatttac tattttccct tcttacgtaa atatttttct ttttaattct aaatcaatct    8460
ttttcaattt tttgtttgta ttctttttctt gcttaaatct ataactacaa aaaacacata   8520
cataaactaa aaatgactga tttgaacaaa ttggtcaagg aattgaatga tttgggtttg    8580
actgacgtca aggaaattgt ctacaaccca tcttacgaac aattattcga agaagaaacc    8640
aagccaggtt tggaaggttt cgacaagggt actttgacca ctttaggtgc tgttgctgtt    8700
gacaccggta ttttcaccgg tcgttctcca aaggacaaat acattgtttg tgatgaaacc    8760
accaaggaca ccgtctggtg gaactctgaa gctgccaaga acgataacaa gccaatgact    8820
caagaaacct ggaaatcttt gagagaattg gttgccaagc aattgtctgg taagagatta    8880
ttcgttgttg acgcttttctg tggtgcttct gaaaagcaca gaattggtgt cagaatggtc    8940
actgaagttg cttggcaagc tcatttcgtc aagaacatgt tcatcagacc aactgacgaa    9000
gaattgaaga acttcaaggc tgacttcacc gttttgaatg gtgccaagtg taccaaccca    9060
aactggaagg aacaaggttt gaactctgaa aactttgttg cttcaacat cactgaaggt    9120 atccaattga ttggtggtac ttggtacggt ggtgaaatga agaagggtat gttctccatg    9180
atgaactatt tcttgccatt gaaaggtgtt gcttccatgc actgttctgc caatgtcggt    9240
aaggatggtg acgttgccat cttcttcggt ctatccggta ctggtaagac cactctatcc    9300
actgacccaa agagacaatt gattggtgat gacgaacacg gttgggacga atctggtgtc    9360
tttaactttg aaggtggttg ttacgccaag accatcaact tatctcaaga aaacgaacca    9420
gatatctacg tgccatccg tcgtgatgct tgttggaaa cgttgttgt cagagctgac       9480 ggttctgttg acttcgacga cggttccaag actgaaaaca ccagagtttc ttacccaatc    9540
taccacattg acaacattgt cagacctgtt tccaaggctg gtcacgctac caaggttatc    9600
ttcttgactg ctgatgcttt cggtgtcttg ccacctgttt ccaaattgac tccagaacaa    9660
accgaatact acttcttgtc cggtttcact gccaaattgg ctggtactga aagaggtgtc    9720
```

```
actgaaccaa ctccaacttt ctctgcttgt ttcggtgctg ctttcttatc tttgcaccca    9780
atccaatacg ctgatgtctt ggttgaaaga atgaaggctt ctggtgctga agcttacttg    9840
gtcaacaccg gttggaacgg tactggtaag agaatctcca tcaaggatac cagaggtatc    9900
attgatgcta tcttggacgg ttccattgaa aaggctgaaa tgggtgaatt gccaatcttc    9960
aacttggcca ttccaaaggc tttgccaggt gttgacccag ccatcttaga tccaagagac   10020
acctacgcta caaggctca atggcaagtc aaggctgaag atttggctaa cagattcgtc   10080
aagaactttg tcaaatacac tgctaaccca gaagctgcca aattggttgg tgctggtcca   10140
aaggcttaaa ggagttaaag gcaaagtttt cttttctaga gccgttccca caataatta   10200 tacgtatatg cttcttttcg tttactatat atctatattt acaagccttt attcactgat   10260
gcaatttgtt tccaaatact tttttggaga tctcataact agatatcatg atggcgcaac   10320
ttggcgctat cttaattact ctggctgcca ggcccgtgta gagggccgca agaccttctg   10380
tacgccatat agtctctaag aacttgaaca agtttctaga cctattgccg cctttcggat   10440
cgctattgtt cctccggatc gatgtacaca accgactgca cccaaacgaa cacaaatctt   10500
agca                                                               10504
```

<210> SEQ ID NO 2
<211> LENGTH: 4552
<212> TYPE: DNA
<213> ORGANISM: Artificial Sequence
<220> FEATURE:
<223> OTHER INFORMATION: nucleotide sequence of fragment 3 (Figure 2),
      which includes pyruvate carboxylase (PYC2) from S. cerevisiae
      codon pair optimized for expression in S. cerevisiae

<400> SEQUENCE: 2

```
cggatcgatg tacacaaccg actgcaccca acgaacaca aatcttagca gtgcgggcca      60 gaaaaggaa gtgtttccct ccttcttgaa ttgatgttac cctcataaag cacgtggcct     120
cttatcgaga aagaaattac cgtcgctcgt gatttgtttg caaaaagaac aaaactgaaa     180
aaacccagac acgctcgact tcctgtcttc ctattgattg cagcttccaa tttcgtcaca     240
caacaaggtc ctagcgacgg ctcacaggtt ttgtaacaag caatcgaagg ttctggaatg     300
gcgggaaagg gtttagtacc acatgctatg atgcccactg tgatctccag agcaaagttc     360
gttcgatcgt actgttactc tctctctttc aaacagaatt gtccgaatcg tgtgacaaca     420
acagcctgtt ctcacacact ctttcttct aaccaagggg gtggtttagt ttagtagaac     480
ctcgtgaaac ttcatttac atatatataa acttgcataa attggtcaat gcaagaaata     540
catatttggt ctttttctaat tcgtagtttt tcaagttctt agatgctttc tttttctctt     600
ttttacagat catcaaggaa gtaattatct acttttttaca acaaatataa acaatgtcc     660 tcttccaaga tcttggctgg tttgagagac aacttttctt tgttgggtga aaagaacaag     720
attttggtcg ccaacagagg tgaaatccca atcagaattt tcagatctgc tcacgaattg     780
tctatgagaa ctatcgccat ctactctcac gaagatagat tatccatgca cagattgaag     840
gctgatgaag cctacgttat cggtgaagaa ggtcaataca cccagtcgg tgcttacttg     900 gccatggacg aaatcatcga aattgccaag aagcacaagg tcgatttcat ccacccaggt     960
tacggtttct gtctgaaaa ctctgaattt gctgacaagg ttgttaaggc tggtattacc    1020
tggattggtc caccagctga agtcattgaa tctgttggtg acaaggtttc tgccagacat    1080
ttggctgctc gtgccaacgt tccaactgtc ccaggtactc caggtcctat cgaaaccgtt    1140
```

```
caagaagctc tagatttcgt caatgaatac ggttacccag ttatcatcaa ggctgctttc    1200
ggtggtggtg tcgtggtat  gagagttgtc agagaaggtg acgatgtcgc tgatgctttc    1260
caaagagcca cttctgaagc tagaactgct ttcggtaacg tacttgttt  cgtcgaaaga    1320 ttccttggaca agccaaagca cattgaagtt caattattag ctgacaacca cggtaacgtt    1380
gtccacttgt tcgaaagaga ctgttccgtc aaagacgtc  accaaaaggt tgtcgaagtt    1440
gctccagcta agactttacc aagagaagtt agagatgcta tcttgaccga tgccgttaag    1500
ttggctaagg tttgtggtta cagaaacgct ggtactgctg aattcttggt tgacaaccaa    1560
aacagacatt acttcattga aatcaaccca agaattcaag tcgaacacac catcactgaa    1620
gaaatcactg gtattgacat tgtctccgct caaatccaaa tcgccgctgg tgctactttg    1680
actcaattag gtctattaca agacaaaatc accaccagag gtttctctat ccaatgtcgt    1740
atcaccactg aagatccatc caagaacttc caaccagaca ctggtcgttt ggaagtctac    1800
agatccgctg gtggtaacgg tgtcagattg acggtggta  acgccacgc  tggtgctacc    1860 atctctccac actacgactc catgttggtt aagtgttcct gttctggttc tacctacgaa    1920
attgtcagaa gaaagatgat cagagctttg attgaattca gaatcagagg tgtcaagacc    1980
aacatcccat tcttgttgac tttgttgacc aacccagttt tcattgaagg tacctactgg    2040
accactttca tcgatgacac tccacaattg ttccaaatgg tttcctctca aaacagagct    2100
caaaaattgt tgcactactt ggctgacttg gccgtcaacg ttcctctat  caagggtcaa    2160 atcggtttac caaagttgaa gtccaaccct tccgttccac atttgcacga tgctcaaggt    2220
aatgtcatca acgttaccaa atctgcccca ccatccggtt ggagacaagt cttgttggaa    2280
aagggtccat ccgaatttgc caagcaagtc agacaattca acggtacttt gttgatggac    2340
accacctgga gagatgctca ccaatctttg ctagctacca gagtcagaac tcacgatttg    2400
gccaccattg ctccaaccac tgctcacgct ttggctggtg cctttgcttt ggaatgttgg    2460
ggtggtgcta ctttcgatgt cgccatgaga ttcttgcatg aggacccatg gaaagattg     2520 agaaaattga gatctttggt cccaaacatt ccattccaaa tgttgttgag aggtgctaac    2580
ggtgttgctt actcctcttt gccagacaac gccattgacc atttcgttaa gcaagccaag    2640
gacaatggtg ttgacatttt cagagtcttt gacgctttga acgacttgga acaattgaag    2700
gttggtgtta atgctgtcaa gaaggctggt ggtgttgtcg aagctaccgt tgttactct    2760 ggtgacatgt tgcaaccagg taagaaatac aacttggact actacttaga agttgtcgaa    2820
aagatcgttc aaatgggtac tcacatcttg ggtatcaagg acatggctgg taccatgaag    2880
ccagctgctg ccaaattgtt gattggttct ttacgtacca gatacccaga cttgccaatc    2940
cacgttcact ctcatgactc cgctggtact gctgttgctt ccatgactgc ttgtgctttg    3000
gccggtgctg atgttgttga cgttgccatt aactccatgt ccggtttgac ctctcaacca    3060
tctattaacg ctttgttggc ctccttggaa ggtaacattg acactggtat caacgtcgaa    3120
cacgttagag aattggacgc ttactgggct gaaatgagat tattatactc ttgtttcgaa    3180
gctgacttga agggtccaga ccctgaagtt taccaacacg aaattccagg tggtcaattg    3240
accaacttgt tgttccaagc tcaacaatta ggtctaggtg aacatgggc  tgaaaccaag    3300 agagcttaca gagaagctaa ctacttgttg ggtgacattg ttaaggtcac cccaacttct    3360
aaggtcgttg gtgatttggc tcaattcatg gtttctaaca aattgacttc tgatgacatc    3420
agaagattag ctaactcttt ggacttccca gactccgtta tggacttctt cgaaggtttg    3480
atcggtcaac catacggtgg tttcccagaa ccattgagat ccgatgtttt gagaaacaag    3540
```

```
cgtcgtaaat tgacttgtag accaggttta gaattggaac cattcgattt ggaaaagatc    3600
agagaagatt tgcaaaacag attcggtgat atcgatgaat gtgatgttgc ctcctacaac    3660
atgtatcctc gtgtctacga agatttccaa aagattagag aaacttacgg tgacttgtct    3720
gtcttaccaa ccaagaactt cttggctcca gctgaaccag acgaagaaat cgaagtcacc    3780
attgaacaag gtaagacttt gattatcaaa ttacaagctg ttggtgattt gaacaagaaa    3840
accggtcaaa gagaagtcta cttcgaattg aacggtgaat tgagaaagat cagagttgct    3900
gacaaatctc aaaacattca atctgttgcc aagccaaagg ctgatgtcca cgacacccac    3960
caaatcggtg ctccaatggc tggtgtcatc attgaagtca aggttcacaa gggttctttg    4020
gtcaagaagg gtgaatctat cgccgttttg tctgctatga agatggaaat ggttgtttcc    4080
tctccagctg atggtcaagt caaagatgtc tttatccgtg acggtgaatc cgtcgatgct    4140
tctgacttgt tggttgtttt ggaagaagaa actctaccac cttctcaaaa gaaataaagc    4200
gaatttctta tgatttatga ttttattat taaataagtt ataaaaaaaa taagtgtata    4260
caaattttaa agtgactctt aggttttaaa acgaaaattc ttattcttga gtaactcttt    4320
cctgtaggtc aggttgcttt ctcaggtata gcatgaggtc gctcttattg accacacctc    4380
taccggcatg ccgagcaaat gcctgcaaat cgctccccat ttcacccaat tgtagatatg    4440
ctaactccag caatgagttg atgaatctcg gtgtgtattt tatgtcctca gaggacaacc    4500
tcacgctttc cggcatcttc cagaccacag tatatccatc cgcctcctgt tg            4552
```

<210> SEQ ID NO 3  
<211> LENGTH: 1572  
<212> TYPE: DNA  
<213> ORGANISM: Artificial Sequence  
<220> FEATURE:  
<223> OTHER INFORMATION: nucleotide sequence of the PCR template for
     fragment 4 (Figure 2), which includes a KanMX selection marker
     functional in S. cerevisiae

<400> SEQUENCE: 3

```
tcgtacgctg caggtcgacg aattctaccg ttcgtataat gtatgctata cgaagttata      60
gatctgttta gcttgcctcg tccccgccgg gtcacccggc cagcgacatg gaggcccaga     120
ataccctcct tgacagtctt gacgtgcgca gctcaggggc atgatgtgac tgtcgcccgt     180
acatttagcc catacatccc catgtataat catttgcatc catacatttt gatggccgca     240
cggcgcgaag caaaaattac ggctcctcgc tgcagacctg cgagcaggga acgctcccc     300 tcacagacgc gttgaattgt ccccacgccg cgcccctgta gagaaatata aaggttagg     360 atttgccact gaggttcttc tttcatatac ttccttttaa aatcttgcta ggatacagtt    420
ctcacatcac atccgaacat aaacaaccat gggtaaggaa aagactcacg tttcgaggcc    480
gcgattaaat tccaacatgg atgctgattt atatgggtat aaatgggctc gcgataatgt    540
cgggcaatca ggtgcgacaa tctatcgatt gtatgggaag cccgatgcgc cagagttgtt    600
tctgaaacat ggcaaaggta gcgttgccaa tgatgttaca gatgagatgg tcagactaaa    660
ctggctgacg gaatttatgc ctcttccgac catcaagcat tttatccgta ctcctgatga    720
tgcatggtta ctcaccactg cgatccccgg caaaacagca ttccaggtat tagaagaata    780
tcctgattca ggtgaaaata ttgttgatgc gctggcagtg ttcctgcgcc ggttgcattc    840
gattcctgtt tgtaattgtc cttttaacag cgatcgcgta tttcgtctcg ctcaggcgca    900
atcacgaatg aataacggtt tggttgatgc gagtgatttt gatgacgagc gtaatggctg    960
```

```
gcctgttgaa caagtctgga agaaatgca taagcttttg ccattctcac cggattcagt    1020
cgtcactcat ggtgatttct cacttgataa ccttattttt gacgagggga aattaatagg    1080
ttgtattgat gttggacgag tcggaatcgc agaccgatac caggatcttg ccatcctatg    1140
gaactgcctc ggtgagtttt ctccttcatt acagaaacgg cttttcaaa aatatggtat    1200 tgataatcct gatatgaata aattgcagtt tcatttgatg ctcgatgagt ttttctaatc    1260
agtactgaca ataaaaagat tcttgttttc aagaacttgt catttgtata gttttttat    1320 attgtagttg ttctatttta atcaaatgtt agcgtgattt atatttttt tcgcctcgac    1380 atcatctgcc cagatgcgaa gttaagtgcg cagaaagtaa tatcatgcgt caatcgtatg    1440
tgaatgctgg tcgctatact gctgtcgatt cgatactaac gccgccatcc agtgtcgaaa    1500
acgagctcat aacttcgtat aatgtatgct atacgaacgg tagaattcga tatcagatcc    1560
actagtggcc ta                                                         1572

<210> SEQ ID NO 4
<211> LENGTH: 2260
<212> TYPE: DNA
<213> ORGANISM: Artificial Sequence
<220> FEATURE:
<223> OTHER INFORMATION: nucleotide sequence of fragment 5 (Figure 2),
      which includes a putative dicarboxylic acid transporter from
      Aspergillus niger codon pair optimized for expression in S.
      cerevisiae

<400> SEQUENCE: 4
aacgttgtcc aggtttgtat ccacgtgtgt ccgttccgcc aatattccgc gtgcccgcgg      60
aaccgccaga tattcattac ttgacgcaaa agcgtttgaa ataatgacga aaagaagga     120 agaaaaaaaa agaaaatac cgcttctagg cgggttatct actgatccga gcttccacta    180
ggatagcacc caaacacctg catatttgga cgacctttac ttacaccacc aaaaaccact    240
ttcgcctctc ccgcccctga taacgtccac taattgagcg attacctgag cggtcctctt    300
ttgtttgcag catgagactt gcatactgca aatcgtaagt agcaacgtgt caaggtcaaa    360
actgtatgga aaccttgtca cctcacttaa ttctagctag cctaccctgc aagtcaagag    420
gtgtccgtga ttcctagcca cctcaaggta tgcctctccc cggaaactgt ggcctttcct    480
ggcacacatg atctccacga tttcaacata taaatagctt ttgataatgg caatattaat    540
caaatttatt ttacttcttt cttgtaacat ctctcttgta atcccttatt ccttctagct    600
atttttcata aaaaccaag caactgctta tcaacacaca aacactaaat caaaatgaac    660
gttgaaactt ctttgccagg ttcttctggt tctgacttgg aaactttcca ccacgaaacc    720
aagaagcatg ccaaccacga ctctggtatt ccgtcaacc atgaagctga aattggtgtt    780
aaccacactt tcgaaaagcc aggtccagtt ggtatcagag aaagattacg tcacttcacc    840
tgggcttggt acactttgac catgtcctgt ggtggtttgg cttttgttgat tgtcaaccaa    900 ccacacgact tcaagggttt gaaagatatt gccagagttg tctactgttt gaacttggct    960
ttctttgtta tcgttacctc tttgatggcc atcagattca tcttgcacaa gaacatgtgg   1020
gaatccttgg gtcacgacag agaaggtttg ttttccccaa ctttctggtt atccattgct   1080
accatgatca ctggtttgta caagtgtttc ggtgatgatg ctaacgaaaa gttcaccaag   1140
tgtttgcaag ttttgttctg gatctactgt ggttgtacca tgatcactgc tgtcggtcaa   1200 tactcttcg tctttgctac ccacaaatac gaattgcaca ccatgatgcc atcctggatc   1260
ttgccagctt tcccagttat gttgtctggt actatcgcct ccgtcatcgg ttctggtcaa   1320
```

```
ccagcttccg atggtattcc aattattatt gctggtatca ctttccaagg tttaggtttc    1380
tccatctcct tcatgatgta cgctcactac attggtagat tgatggaagt tggtttacca    1440
tctccagaac acagaccagg tatgttcatc tgtgttggtc ctccagcttt caccgctttg    1500
gctttggtcg gtatggccaa ggctttacca gacgacttcc aaattgtcgg tgaccctcac    1560
gctgtcattg acggtcgtgt tatgttgttc ttggctgtct ctgctgccat cttcttatgg    1620
gctttgtctt tctggttctt ctgtatcgct gttgttgctg ttgtcagatc tccaccaaag    1680
ggtttccatt tgaactggtt tgccatggtt ttcccaaaca ctggtttcac cttggctacc    1740
atcactttgg ctaacatgtt cgaatctcca ggtgtcaagg gtgttgccac tgctatgtcc    1800
ctatgtgtca tcatcatgtt tattttcgtc ttggtttctg ccatcagagc tgtcatcaga    1860
aaggacatca tgtggccagg tcaagatgaa gatgtttctg aataaagagt aataattatt    1920
gcttccatat aatattttta tatacctctt attttatgt attagttaat taagtatttt     1980
tatctatctg cttatcattt tcttttcata taggggggt tggtgttttc ttgcccatca     2040
gattgatgtc ctccaactcg gcactatttt acaaagggtt tttttgtaag agaaggagaa    2100
gacagatact aaaccatacg ttactcgaaa caaaaaaaaa aaaaatggaa aaagctgcta    2160
tcaacaaaag acggcctcat caaacctaaa gaaaccatgt cagcgtcctc aaataaccac    2220
aaacatcctt cccatatgct cggtcgtgct tgttgtacct                          2260
```

<210> SEQ ID NO 5
<211> LENGTH: 2432
<212> TYPE: DNA
<213> ORGANISM: Artificial Sequence
<220> FEATURE:
<223> OTHER INFORMATION: nucleotide sequence of fragment 6 (Figure 2), which includes malate dehydrogenase (MDH3) from S. cerevisiae codon pair optimized for expression in S. cerevisiae

<400> SEQUENCE: 5

```
aaataaccac aaacatcctt cccatatgct cggtcgtgct tgttgtacct gtgcttttct      60 tttttttgcgg tcacccccat gtggcgggga ggcagaggag taggtagagc aacgaatcct    120
actatttatc caaattagtc taggaactct ttttctagat tttttagatt tgagggcaag    180
cgctgttaac gactcagaaa tgtaagcact acggagtaga acgagaaatc cgccataggt    240
ggaaatccta gcaaaatctt gcttacccta gctagcctca ggtaagctag ccttagcctg    300
tcaaattttt ttcaaaattt ggtaagtttc tactagcaaa gcaaacacgg ttcaacaaac    360
cgaaaactcc actcattata cgtggaaacc gaaacaaaaa aacaaaaacc aaaatactcg    420
ccaatgagaa agttgctgcg tttctacttt cgaggaagag gaactgagag gattgactac    480
gaaaggggca aaaacgagtc gtattctccc attattgtct gctaccacgc ggtctagtag    540
aataagcaac cagtcaacgc taagacaggt aatcaaaata ccagtctgct ggctacgggc    600 tagttttac ctcttttaga acccactgta aaagtccgtt gtaaagcccg ttctcactgt     660
tggcgttttt tttttttggg tttagtttct tattttcat ttttttctttt catgaccaaa    720 aacaaacaaa tctcgcgatt tgtactgcgg ccactggggc gtggccaaaa aaatgacaaa    780
tttagaaacc ttagtttctg attttttcctg ttatgaggag atatgataaa aaatattact    840
gctttattgt ttttttttta tctactgaaa tagagaaact tacccaagga ggaggcaaaa    900
aaaagagtat atatacagca ggtaccattc agatttttaat atattctttt ctcttcttct    960
acactattat tataataatt ttactatatt catttttagc ttaaaacctc atagaatatt    1020
attcttcagt cactcgctta aatacttatc aaaaatggtt aaggttgcca tcttaggtgc   1080
```

```
ttctggtggt gtcggtcaac cattatctct attattgaaa ttgtctccat acgtttctga    1140
attggctttg tacgatatca gagctgctga aggtattggt aaggatttgt cccacatcaa    1200
caccaactcc tcttgtgttg gttacgacaa ggattccatc gaaaacactt tgtccaatgc    1260
tcaagttgtc ttgattccag ctggtgttcc aagaaagcca ggtttgacca gagatgattt    1320
gttcaagatg aacgctggta tcgttaagtc tttggttact gctgtcggta aatttgcccc    1380
aaacgctcgt atcttagtca tctccaaccc tgttaactct ttggttccaa ttgccgttga    1440
aactttgaag aagatgggta agttcaagcc aggtaacgtt atgggtgtca ccaacttgga    1500
tttggtcaga gctgaaactt tcttggttga ctacttgatg ttgaagaacc aaagatcgg    1560 tcaagaacaa gacaagacca ccatgcacag aaaggtcacc gtcatcggtg gtcactctgg    1620
tgaaaccatc attccaatca tcactgacaa atccttggtt ttccaattgg acaagcaata    1680
cgaacatttc atccacagag tccaattcgg tggtgacgaa attgtcaagg ccaagcaagg    1740
tgccggttct gctaccttgt ccatggcttt cgctggtgcc aaatttgctg aagaagtctt    1800
acgttctttc cacaacgaaa agccagaaac tgaatctttg tctgctttcg tctacttgcc    1860
aggtttgaag aacggtaaga aggctcaaca attagtcggt gacaactcca ttgaatactt    1920
ctctttgcca attgttttga gaacggttc cgttgtttcc attgacactt ctgttttgga    1980
aaaattgtct ccaagagaag aacaattggt caacactgct gtcaaggaat gagaaagaa    2040 cattgaaaag ggtaagtctt tcatcttgga cagttaaagt ctgaagaatg aatgatttga    2100
tgatttcttt ttccctccat ttttcttact gaatatatca atgatataga cttgtatagt    2160
ttattatttc aaattaagta gctatatata gtcaagataa cgtttgtttg acacgattac    2220
attattcgtc gacatctttt ttcagcctgt cgtggtagca atttgaggag tattattaat    2280
tgaataggtt cattttgcgc tcgcataaac agttttcgtc agggacagta tgttggaatg    2340
agtggtaatt aatggtgaca tgacatgtta tagcaatacc tcgaaaccaa cgaatccagc    2400
cagcatgtcg acacccacaa gatgtagtgc ac                                  2432
```

<210> SEQ ID NO 6
<211> LENGTH: 2656
<212> TYPE: DNA
<213> ORGANISM: Artificial Sequence
<220> FEATURE:
<223> OTHER INFORMATION: nucleotide sequence of fragment 7 (Figure 2),
which includes fumarase (fumB) from Escherichia coli codon pair
optimized for expression in S. cerevisiae

<400> SEQUENCE: 6

```
gaaaccttcg aatccagcca gcatgtcgac acccacaaga tgtagtgcac gtgcttagtc     60
aaaaaattag cctttttaatt ctgctgtaac ccgtacatgc ccaaaatagg gggcgggtta   120
cacagaatat ataacatcgt aggtgtctgg gtgaacagtt tattcctggc atccactaaa   180
tataatggag cccgcttttt aagctggcat ccagaaaaaa aagaatccc agcaccaaaa    240 tattgttttc ttcaccaacc atcagttcat aggtccattc tcttagcgca actacagaga   300 acagggggcac aaacaggcaa aaacgggca caacctcaat ggagtgatgc aacctgcctg   360
gagtaaatga tgacacaagg caattgaccc acgcatgtat ctatctcatt ttcttacacc   420
ttctattacc ttctgctctc tctgatttgg aaaaagctga aaaaaaggt tgaaaccagt    480 tccctgaaat tattccccta cttgactaat aagtatataa agacggtagg tattgattgt   540
aattctgtaa atctatttct taaacttctt aaattctact tttatagtta gtcttttttt    600
```

```
tagttttaaa acaccaagaa cttagtttcg aataaacaca cataaacaaa caaaatgtcc    660
aacaagcctt tcatctacca agctccattc ccaatgggta aggacaacac tgaatactac    720
ttgttgactt ctgactacgt ttccgttgct gatttcgatg gtgaaaccat cttgaaggtt    780
gaaccagaag ccttgacttt gttggctcaa caagccttcc acgatgcttc tttcatgttg    840
cgtccagctc accaaaagca agttgctgcc attttgcacg acccagaagc ctccgaaaac    900
gacaaatacg ttgctttgca attcttgaga aactctgaaa ttgctgccaa gggtgtctta    960
ccaacttgtc aagacactgg tactgccatc attgtcggta agaagggtca agagtctgg   1020
accggtggtg gtgacgaaga aactctatcc aagggtgttt acaacactta cattgaagat   1080
aatttacgtt actctcaaaa tgctgctttg gacatgtaca aggaagtcaa cactggtact   1140
aacttgccag ctcaaatcga cttatacgct gttgacggtg acgaatacaa gttcttgtgt   1200
gttgccaagg tggtggttc tgctaacaag acctacttgt accagaaaac caaggctttg   1260
ttgactccag gtaaattgaa gaacttcttg gtcgaaaaga tgagaacttt gggtactgct   1320
gcttgtccac ataccacat tgctttcgtt atcggtggta cttccgctga aaccaacttg   1380
aaaaccgtca aattggcttc cgctcactac tacgatgaat tgccaactga aggtaacgaa   1440
cacggtcaag ccttcagaga tgtccaattg aacaagaat tgttggaaga agctcaaaaa   1500
ttaggtttgg gtgctcaatt tggtggtaaa tactttgctc acgatatcag agttatcaga   1560
ttaccaagac atggtgcttc ttgtccagtt ggtatgggtg tttcctgttc tgctgacaga   1620
aacatcaagg ccaagatcaa cagagaaggt atctggattg aaaaattgga acacaaccca   1680
ggtcaataca tccccacaaga attgagacaa gctggtgaag tgaagctgt caaggttgac   1740
ttgaacagac caatgaagga aatcttggct caattatctc aatacccagt tccaccaga   1800
ttatctttga ccggtactat cattgtcggt cgtgacattg ctcatgccaa gttgaaggaa   1860
ttgattgatg ctggtaagga attgcctcaa tacatcaagg accatccaat ctactacgct   1920
ggtccagcca agaccccagc tggttaccca tctggttctt gggtccaac caccgctggt   1980
agaatggact cttacgttga cttgctacaa tctcacggtg gttccatgat catgttggct   2040
aagggtaaca gatctcaaca agtcaccgat gcttgtcaca agcacggtgg tttctatttg   2100
ggttccattg gtggtccagc tgctgtcttg gctcaacaat ctatcaagca cttggaatgt   2160
gttgcttacc cagaatttggg tatggaagcc atctggaaga ttgaagtcga agatttccca   2220
gctttcatct tagtcgatga caagggtaac gacttcttcc aacaaattgt caacaagcaa   2280
tgtgccaact gtaccaagta aaataaagca atcttgatga ggataatgat ttttttttga   2340
atatacataa atactaccgt ttttctgcta gattttgtga agacgtaaat aagtacatat   2400
tactttttaa gccaagacaa gattaagcat taacttacc cttttctctt ctaagtttca   2460
atactagtta tcactgttta aaagttatgg cgagaacgtc ggcggttaaa atatattacc   2520
ctgaacgtgg tgaattgaag ttctaggatg gtttaaagat ttttcctttt tgggaaataa   2580
gtaaacaata tattgctgcc ttcctcaaag ccaaagttcg cgttccgacc ttgcctccca   2640
aatccgagtt gcgatt                                                   2656
```

<210> SEQ ID NO 7
<211> LENGTH: 4429
<212> TYPE: DNA
<213> ORGANISM: Artificial Sequence
<220> FEATURE:
<223> OTHER INFORMATION: nucleotide sequence of fragment 8 (Figure 2), which includes fumarate reductase from Trypanosoma brucei (FRDg) codon pair optimized for expression in S. cerevisiae

<400> SEQUENCE: 7

```
aaagccaaag ttcgcgttcc gaccttgcct cccaaatccg agttgcgatt gtgcttggct      60
gataatagcg tataaacaat gcatactttg tacgttcaaa atacaatgca gtagatatat     120
ttatgcatat tacatataat acatatcaca taggaagcaa caggcgcgtt ggacttttaa     180
ttttcgagga ccgcgaatcc ttacatcaca cccaatcccc cacaagtgat cccccacaca     240
ccatagcttc aaaatgtttc tactcctttt ttactcttcc agattttctc ggactccgcg     300
catcgccgta ccacttcaaa acacccaagc acagcatact aaatttcccc tctttcttcc     360
tctagggtgt cgttaattac ccgtactaaa ggtttggaaa agaaaaaaga caccgcctcg     420
tttcttttc ttcgtcgaaa aaggcaataa aaattttat cacgtttctt tttcttgaaa     480
atttttttt ttgatttttt tctcttcga tgacctccca ttgatattta agttaataaa     540
cggtcttcaa tttctcaagt ttcagtttca tttttcttgt tctattacaa cttttttttac    600
ttcttgctca ttagaaagaa agcatagcaa tctaatctaa gttttaatta caaaatggtt     660
gatggtagat cttctgcttc cattgttgcc gttgacccag aaagagctgc cagagaaaga     720
gatgctgctg ccagagcttt gttgcaagac tctccattgc acaccaccat gcaatacgct     780
acctctggtt tggaattgac tgttccatac gctttgaagg ttgttgcttc tgctgacact     840
ttcgacagag ccaaggaagt tgctgatgaa gtcttgagat gtgcctggca attggctgac     900
accgttttga actctttcaa cccaaactct gaagtctctt tagtcggtag attaccagtc     960
ggtcaaaagc atcaaatgtc tgctccattg aaacgtgtca tggcttgttg tcaaagagtc    1020
tacaactcct ctgctggttg tttcgaccca tccactgctc cagttgccaa ggctttgaga    1080
gaaattgctt tgggtaagga agaaacaat gcttgtttgg aagctttgac tcaagcttgt    1140
accttgccaa actctttcgt cattgatttc gaagctggta ctatctccag aaagcacgaa    1200
cacgcttctt tggatttggg tggtgttttcc aagggttaca tcgtcgatta cgtcattgac    1260
aacatcaatg ctgctggttt ccaaaacgtt ttctttgact ggggtggtga ctgtcgtgcc    1320
tccggtatga acgccagaaa cactccatgg gttgtcggta tcactagacc tccttccttg    1380
gacatgttgc aaaccctcc aaaggaagct tcttacatct ccgtcatctc tttggacaat    1440
gaagctttgg ctacctctgg tgattacgaa aacttgatct acactgctga cgataaacca    1500
ttgacctgta cctacgattg gaaaggtaag gaattgatga agccatctca atccaatatc    1560
gctcaagttt ccgtcaagtg ttactctgcc atgtacgctg acgctttggc taccgcttgt    1620
ttcatcaagc gtgacccagc caaggtcaga caattgttgg atggttggag atacgttaga    1680
gacaccgtca gagattaccg tgtctacgtc agagaaaacg aaagagttgc caagatgttc    1740
gaaattgcca ctgaagatgc tgaaatgaga aagagaagaa tttccaacac tttaccagct    1800
cgtgtcattg ttgttggtgg tggtttggct ggtttgtccg ctgccattga agctgctggt    1860
tgtggtgctc aagttgtttt gatggaaaag gaagccaagt gggtggtaa ctctgccaag    1920
gctacctctg gtatcaacgg ttggggtact agagcccaag ctaaggcttc cattgtcgat    1980
ggtggtaagt acttcgaaag agataccta caagtctggta tcggtggtaa caccgatcca    2040
gctttggtta agactttgtc catgaaatct gctgacgcta tcggttggtt gacttctcta    2100
ggtgttccat tgactgtttt gtcccaatta ggtggtcact ccagaaagag aactcacaga    2160
gccccagaca agaaggatgg tactccattg ccaattggtt tcaccatcat gaaaacttta    2220
gaagatcatg ttagaggtaa cttgtccggt agaatcacca tcatggaaaa ctgttccgtt    2280
```

```
acctctttgt tgtctgaaac caaggaaaga ccagacggta ctaagcaaat cagagttacc      2340
ggtgtcgaat tcactcaagc tggttctggt aagaccacca ttttggctga tgctgttatc      2400
ttggccaccg gtggtttctc caacgacaag actgctgatt cttgttgag agaacatgcc      2460 ccacacttgg ttaacttccc aaccaccaac ggtccatggg ctactggtga tggtgtcaag      2520
ttggctcaaa gattaggtgc tcaattggtc gatatggaca aggttcaatt gcacccaact      2580
ggtttgatca acccaaagga cccagccaac caaccaaat tcttgggtcc agaagctcta      2640
agaggttctg gtggtgtttt gttgaacaaa caaggtaaga gatttgtcaa cgaattggat      2700
ttgagatctg ttgttttccaa ggccatcatg gaacaaggtg ctgaataccc aggttctggt      2760
ggttccatgt ttgcttactg tgtcttgaac gctgctgctc aaaaattgtt tggtgtttcc      2820
tctcacgaat tctactggaa gaagatgggt tgttcgtca aggctgacac catgagagac      2880
ttggctgctt tgattggttg tccagttgaa tccgttcaac aaactttaga agaatacgaa      2940
agattatcca tctctcaaag atcttgtcca attaccagaa aatctgttta cccatgtgtt      3000
ttgggtacta aaggtccata ctatgtcgcc tttgtcactc catctatcca ctacaccatg      3060
ggtggttgtt tgatttctcc atctgctgaa atccaaatga gaacacttc ttccagagcc      3120 ccattgtccc actccaaccc aatcttgggt ttattcggtg ctggtgaagt caccggtggt      3180
gtccacggtg gtaacagatt aggtggtaac tctttgttgg aatgtgttgt tttcggtaga      3240
attgccggtg acagagcttc taccattttg caaagaaagt cctctgcttt gtctttcaag      3300
gtctggacca ctgttgtttt gagagaagtc agagaaggtg gtgtctacgg tgctggttcc      3360
cgtgtcttga gattcaactt accaggtgct ctacaaagat ctggtctatc cttgggtcaa      3420
ttcattgcca tcagaggtga ctgggacggt caacaattga ttggttacta ctctccaatc      3480
actttgccag acgatttggg tatgattgac attttggcca gatctgacaa gggtacttta      3540
cgtgaatgga tctctgcttt ggaaccaggt gacgctgtcg aaatgaaggc ttgtggtggt      3600
ttggtcatcg aaagaagatt atctgacaag cacttcgttt tcatgggtca cattatcaac      3660
aagctatgtt tgattgctgg tggtactggt gttgctccaa tgttgcaaat catcaaggcc      3720
gctttcatga agccattcat cgacactttg gaatccgtcc acttgatcta cgctgctgaa      3780
gatgtcactg aattgactta cagagaagtt ttggaagaac gtcgtcgtga atccagaggt      3840
aaattcaaga aaactttcgt tttgaacaga cctcctccat tatggactga cggtgtcggt      3900
ttcatcgacc gtggtatctt gaccaaccac gttcaaccac catctgacaa cttattggtt      3960 gccatcgtg tcccaccagt tatgcaaaga attgtcaagg ccactttaaa gactttaggt      4020
tacaacatga acttggtcag aaccgttgac gaaactgaac catctggaag ttaaaggaag      4080
tatctcggaa atattaattt aggccatgtc cttatgcacg tttctttga tacttacggg      4140 tacatgtaca caagtatatc tatatatata aattaatgaa aatcccctat ttatatat      4200 gactttaacg agacagaaca gtttttttatt ttttatccta tttgatgaat gatacagttt      4260
cttattcacg tgttataccc acaccaaatc caatagcaat accggccatc acaatcactg      4320
tttcggcagc ccctaagatc agacaaaaca tccggaacca ccttaaatca acgtccctca      4380
gaaagcctgt atgcgaagcc acaatccttt ccaacagacc atactaagt               4429
```

<210> SEQ ID NO 8
<211> LENGTH: 1138
<212> TYPE: PRT
<213> ORGANISM: Trypanosoma brucei
<220> FEATURE:
<221> NAME/KEY: MISC_FEATURE
<222> LOCATION: (1)..(1138)
<223> OTHER INFORMATION: Fumarate reductase (FRDg)

<400> SEQUENCE: 8

```
Met Val Asp Gly Arg Ser Ser Ala Ser Ile Val Ala Val Asp Pro Glu
1               5                   10                  15

Arg Ala Ala Arg Glu Arg Asp Ala Ala Arg Ala Leu Leu Gln Asp
            20                  25                  30

Ser Pro Leu His Thr Thr Met Gln Tyr Ala Thr Ser Gly Leu Glu Leu
            35                  40                  45

Thr Val Pro Tyr Ala Leu Lys Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
            115                 120                 125

Cys Phe Asp Pro Ser Thr Ala Pro Val Ala Lys Ala Leu Arg Glu Ile
130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
            195                 200                 205

Phe Gln Asn Val Phe Phe Asp Trp Gly Gly Asp Cys Arg Ala Ser Gly
210                 215                 220

Met Asn Ala Arg Asn Thr Pro Trp Val Val Gly Ile Thr Arg Pro Pro
225                 230                 235                 240

Ser Leu Asp Met Leu Pro Asn Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
            275                 280                 285

Trp Lys Gly Lys Glu Leu Met Lys Pro Ser Gln Ser Asn Ile Ala Gln
290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
            340                 345                 350

Arg Glu Asn Glu Arg Val Ala Lys Met Phe Glu Ile Ala Thr Glu Asp
            355                 360                 365

Ala Glu Met Arg Lys Arg Ile Ser Asn Thr Leu Pro Ala Arg Val
370                 375                 380

Ile Val Val Gly Gly Gly Leu Ala Gly Leu Ser Ala Ala Ile Glu Ala
385                 390                 395                 400
```

-continued

Ala Gly Cys Gly Ala Gln Val Leu Met Glu Lys Glu Ala Lys Leu
            405                 410                 415

Gly Gly Asn Ser Ala Lys Ala Thr Ser Gly Ile Asn Gly Trp Gly Thr
                420                 425                 430

Arg Ala Gln Ala Lys Ala Ser Ile Val Asp Gly Gly Lys Tyr Phe Glu
            435                 440                 445

Arg Asp Thr Tyr Lys Ser Gly Ile Gly Gly Asn Thr Asp Pro Ala Leu
            450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                485                 490                 495

Arg Lys Arg Thr His Arg Ala Pro Asp Lys Lys Asp Gly Thr Pro Leu
            500                 505                 510

Pro Ile Gly Phe Thr Ile Met Lys Thr Leu Glu Asp His Val Arg Gly
            515                 520                 525

Asn Leu Ser Gly Arg Ile Thr Ile Met Glu Asn Cys Ser Val Thr Ser
            530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
            580                 585                 590

Thr Ala Asp Ser Leu Leu Arg Glu His Ala Pro His Leu Val Asn Phe
            595                 600                 605

Pro Thr Thr Asn Gly Pro Trp Ala Thr Gly Asp Gly Val Lys Leu Ala
            610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Val Leu Leu Asn Lys
            660                 665                 670

Gln Gly Lys Arg Phe Val Asn Glu Leu Asp Leu Arg Ser Val Val Ser
            675                 680                 685

Lys Ala Ile Met Glu Gln Gly Ala Glu Tyr Pro Gly Ser Gly Gly Ser
            690                 695                 700

Met Phe Ala Tyr Cys Val Leu Asn Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
            755                 760                 765

Arg Ser Cys Pro Ile Thr Arg Lys Ser Val Tyr Pro Cys Val Leu Gly
            770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

-continued

Asn Thr Ser Ser Arg Ala Pro Leu Ser His Ser Asn Pro Ile Leu Gly
            820                 825                 830

Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ser Thr Ile Leu Gln Arg Lys Ser Ser Ala Leu Ser
865                 870                 875                 880

Phe Lys Val Trp Thr Thr Val Val Leu Arg Glu Val Arg Glu Gly Gly
                885                 890                 895

Val Tyr Gly Ala Gly Ser Arg Val Leu Arg Phe Asn Leu Pro Gly Ala
            900                 905                 910

Leu Gln Arg Ser Gly Leu Ser Leu Gly Gln Phe Ile Ala Ile Arg Gly
        915                 920                 925

Asp Trp Asp Gly Gln Gln Leu Ile Gly Tyr Tyr Ser Pro Ile Thr Leu
    930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
            980                 985                 990

His Phe Val Phe Met Gly His Ile Ile Asn Lys Leu Cys Leu Ile Ala
        995                 1000                1005

Gly Gly Thr Gly Val Ala Pro Met Leu Gln Ile Ile Lys Ala Ala
    1010                1015                1020

Phe Met Lys Pro Phe Ile Asp Thr Leu Glu Ser Val His Leu Ile
    1025                1030                1035

Tyr Ala Ala Glu Asp Val Thr Glu Leu Thr Tyr Arg Glu Val Leu
    1040                1045                1050

Glu Glu Arg Arg Arg Glu Ser Arg Gly Lys Phe Lys Lys Thr Phe
    1055                1060                1065

Val Leu Asn Arg Pro Pro Pro Leu Trp Thr Asp Gly Val Gly Phe
    1070                1075                1080

Ile Asp Arg Gly Ile Leu Thr Asn His Val Gln Pro Pro Ser Asp
    1085                1090                1095

Asn Leu Leu Val Ala Ile Cys Gly Pro Pro Val Met Gln Arg Ile
    1100                1105                1110

Val Lys Ala Thr Leu Lys Thr Leu Gly Tyr Asn Met Asn Leu Val
    1115                1120                1125

Arg Thr Val Asp Glu Thr Glu Pro Ser Gly
    1130                1135

<210> SEQ ID NO 9
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 1 (Figure 2)

<400> SEQUENCE: 9
cattatatcg aggaaagccc                                              20

<210> SEQ ID NO 10
<211> LENGTH: 75

```
<212> TYPE: DNA
<213> ORGANISM: Artificial Sequence
<220> FEATURE:
<223> OTHER INFORMATION: nucleotide sequence of the primer used to
      generate fragment 1 (Figure 2)

<400> SEQUENCE: 10
aaagcaaagg aaggagagaa cagaggagta cttgtacgtt cgatgggcaa agaaagagac    60
acaaaactac gtggg                                                     75

<210> SEQ ID NO 11
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 2 (Figure 2)

<400> SEQUENCE: 11
ttgcccatcg aacgtacaag                                                20

<210> SEQ ID NO 12
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 2 (Figure 2)

<400> SEQUENCE: 12
tgctaagatt tgtgttcgtt tgg                                            23

<210> SEQ ID NO 13
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 3 (Figure 2)

<400> SEQUENCE: 13
cggatcgatg tacacaaccg                                                20

<210> SEQ ID NO 14
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 3 (Figure 2)

<400> SEQUENCE: 14
caacaggagg cggatggata tac                                            23

<210> SEQ ID NO 15
<211> LENGTH: 79
<212> TYPE: DNA
<213> ORGANISM: Artificial Sequence
<220> FEATURE:
<223> OTHER INFORMATION: nucleotide sequence of the primer used to
      generate fragment 4 (Figure 2)

<400> SEQUENCE: 15
acgctttccg gcatcttcca gaccacagta tatccatccg cctcctgttg tcgtacgctg    60
caggtcgacg aattctacc                                                 79
```

<210> SEQ ID NO 16
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 4 (Figure 2)

<400> SEQUENCE: 16
gcggaatatt ggcggaacgg acacacgtgg atacaaacct ggacaacgtt taggccacta    60
gtggatctga tatcg                                                    75

<210> SEQ ID NO 17
<211> LENGTH: 22
<212> TYPE: DNA
<213> ORGANISM: Artificial Sequence
<220> FEATURE:
<223> OTHER INFORMATION: nucleotide sequence of the primer used to
      generate fragment 5 (Figure 2)

<400> SEQUENCE: 17
aacgttgtcc aggtttgtat cc                                            22

<210> SEQ ID NO 18
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 5 (Figure 2)

<400> SEQUENCE: 18
aggtacaaca agcacgaccg                                               20

<210> SEQ ID NO 19
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 6 (Figure 2) and fragments 120, 121, 122 and 123
      (Figure 7)

<400> SEQUENCE: 19
aaataaccac aaacatcctt ccc                                           23

<210> SEQ ID NO 20
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 6 (Figure 2) and fragments 120, 121, 122 and 123
      (Figure 7)

<400> SEQUENCE: 20
gtgcactaca tcttgtgggt gtc                                           23

<210> SEQ ID NO 21
<211> LENGTH: 22
<212> TYPE: DNA
<213> ORGANISM: Artificial Sequence
<220> FEATURE:
<223> OTHER INFORMATION: nucleotide sequence of the primer used to
      generate fragment 7 (Figure 2)

<400> SEQUENCE: 21

```
gaaaccttcg aatccagcca gc                                              22
```

<210> SEQ ID NO 22
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 7 (Figure 2)

<400> SEQUENCE: 22

```
aatcgcaact cggatttggg                                                 20
```

<210> SEQ ID NO 23
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 8 (Figure 2)

<400> SEQUENCE: 23

```
aaagccaaag ttcgcgttcc                                                 20
```

<210> SEQ ID NO 24
<211> LENGTH: 24
<212> TYPE: DNA
<213> ORGANISM: Artificial Sequence
<220> FEATURE:
<223> OTHER INFORMATION: nucleotide sequence of the primer used to
      generate fragment 8 (Figure 2)

<400> SEQUENCE: 24

```
acttagtatg gtctgttgga aagg                                            24
```

<210> SEQ ID NO 25
<211> LENGTH: 25
<212> TYPE: DNA
<213> ORGANISM: Artificial Sequence
<220> FEATURE:
<223> OTHER INFORMATION: nucleotide sequence of the primer used to
      generate fragment 13 (Figure 3)

<400> SEQUENCE: 25

```
cggcattatt gtgtatggct caata                                           25
```

<210> SEQ ID NO 26
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 13 (Figure 3)

<400> SEQUENCE: 26

```
gaacttcgac ctgttgcaat acttcgggtt cggcacaaac gtgtacggat agggtttcaa     60
agatccatac ttctc                                                      75
```

<210> SEQ ID NO 27
<211> LENGTH: 79
<212> TYPE: DNA
<213> ORGANISM: Artificial Sequence
<220> FEATURE:
<223> OTHER INFORMATION: nucleotide sequence of the primer used to
      generate fragment 14 (Figure 4)

<400> SEQUENCE: 27

```
atccgtacac gtttgtgccg aacccgaagt attgcaacag gtcgaagttc tcgtacgctg    60
caggtcgacg aattctacc                                                  79
```

<210> SEQ ID NO 28
<211> LENGTH: 74
<212> TYPE: DNA
<213> ORGANISM: Artificial Sequence
<220> FEATURE:
<223> OTHER INFORMATION: nucleotide sequence of the primer used to
      generate fragment 115 (Figure 3) and fragment 14 (Figure 4)

<400> SEQUENCE: 28

```
aggtacaaca agcacgaccg agcatatggg aaggatgttt gtggttattt aggccactag    60
tggatctgat atcg                                                       74
```

<210> SEQ ID NO 29
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 15 (Figure 3) and fragments 17 to 110 (Figure 4)

<400> SEQUENCE: 29

```
aaataaccac aaacatcctt ccc                                             23
```

<210> SEQ ID NO 30
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 15 (Figure 3) and fragments 17 to 110 (Figure 4)

<400> SEQUENCE: 30

```
gtgcactaca tcttgtgggt gtc                                             23
```

<210> SEQ ID NO 31
<211> LENGTH: 2033
<212> TYPE: DNA
<213> ORGANISM: Artificial Sequence
<220> FEATURE:
<223> OTHER INFORMATION: nucleotide sequence of fragment 15 (Figure 3)
      and fragment 120 (Figure 7), which includes the nucleotide
      sequence encoding SEQ ID NO: 39 codon pair optimized for
      expression in S. cerevisiae

<400> SEQUENCE: 31

```
taaataacca aaacatcct tcccatatgc tcggtcgtgc ttgttgtacc tgtgcttagt     60
caaaaaatta gccttttaat tctgctgtaa cccgtacatg cccaaaatag ggggcgggtt   120
acacagaata tataacatcg taggtgtctg ggtgaacagt ttattcctgg catccactaa   180
atataatgga gcccgctttt taagctggca tccagaaaaa aaaagaatcc cagcaccaaa   240
atattgtttt cttcaccaac catcagttca taggtccatt ctcttagcgc aactacagag   300
aacaggggca caaacaggca aaaacgggc acaacctcaa tggagtgatg caacctgcct    360
ggagtaaatg atgacacaag gcaattgacc cacgcatgta tctatctcat tttcttacac   420
cttctattac cttctgctct ctctgatttg gaaaaagctg aaaaaaaagg ttgaaaccag    480
ttccctgaaa ttattcccct acttgactaa taagtatata aagacggtag gtattgattg    540
taattctgta aatctatttc ttaaacttct taaattctac ttttatagtt agtctttttt    600
```

```
ttagttttaa aacaccaaga acttagtttc gaataaacac acataaacaa acaaaatggt    660
taaggttgcc atcttaggtg cttctggtgg tgtcggtcaa ccattatctc tattattgaa    720
attgtctcca tacgtttctg aattggcttt gtacgatatc agagctgctg aaggtattgg    780
taaggatttg tcccacatca acaccaactc ctcttgtgtt ggttacgaca aggattccat    840
cgaaaacact tgtccaatg ctcaagttgt cttgattcca gctggtgttc caagaaagcc      900
aggtttgacc agagatgatt tgttcaagat gaacgctggt atcgttaagt ctttggttac    960
tgctgtcggt aaatttgccc aaacgctcg tatcttagtc atctccaacc tgttaactc      1020 tttggttcca attgccgttg aaactttgaa gaagatgggt aagttcaagc caggtaacgt    1080
tatgggtgtc accaacttgg atttggtcag agctgaaact ttcttggttg actacttgat    1140
gttgaagaac ccaaagatcg gtcaagaaca agacaagacc accatgcaca gaaaggtcac    1200
cgtcatcggt ggtcactctg gtgaaaccat cattccaatc atcactgaca aatccttggt    1260
tttccaattg gacaagcaat acgaacattt catccacaga gtccaattcg gtggtgacga    1320
aattgtcaag gccaagcaag gtgccggttc tgctaccttg tccatggctt cgctggtgc     1380 caaatttgct gaagaagtct tacgttcttt ccacaacgaa aagccagaaa ctgaatcttt    1440
gtctgctttc gtctacttgc caggtttgaa gaacggtaag aaggctcaac aattagtcgg    1500
tgacaactcc attgaatact ctctctttgcc aattgttttg agaaacggtt ccgttgtttc    1560
cattgacact tctgttttgg aaaaattgtc tccaagagaa gaacaattgg tcaacactgc    1620
tgtcaaggaa ttgagaaaga acattgaaaa gggtaagtct ttcatcttgg acagttaaag    1680
tctgaagaat gaatgatttg atgatttctt tttccctcca ttttttcttac tgaatatatc    1740 aatgatatag acttgtatag tttattattt caaattaagt agctatatat agtcaagata    1800
acgtttgttt gacacgatta cattattcgt cgacatcttt tttcagcctg tcgtggtagc    1860
aatttgagga gtattattaa ttgaataggt tcattttgcg ctcgcataaa cagttttcgt    1920
cagggacagt atgttggaat gagtggtaat taatggtgac atgacatgtt atagcaatac    1980
ctcgaaacct tcgaatccag ccagcatgtc gacacccaca agatgtagtg cac            2033
```

<210> SEQ ID NO 32
<211> LENGTH: 78
<212> TYPE: DNA
<213> ORGANISM: Artificial Sequence
<220> FEATURE:
<223> OTHER INFORMATION: nucleotide sequence of the primer used to generate fragment 16 (Figure 3)

<400> SEQUENCE: 32

```
gaaaccttcg aatccagcca gcatgtcgac acccacaaga tgtagtgcac acttttttta    60
gaatgacctg ttcccgac                                                  78
```

<210> SEQ ID NO 33
<211> LENGTH: 24
<212> TYPE: DNA
<213> ORGANISM: Artificial Sequence
<220> FEATURE:
<223> OTHER INFORMATION: nucleotide sequence of the primer used to generate fragment 16 (Figure 3)

<400> SEQUENCE: 33

```
cacaagctta ttcttccaaa aatc                                           24
```

<210> SEQ ID NO 34

<211> LENGTH: 3534
<212> TYPE: DNA
<213> ORGANISM: Artificial Sequence
<220> FEATURE:
<223> OTHER INFORMATION: nucleotide sequence of fragment 9 (Figure 1),
which includes fumarase from Rhizopus oryzae codon pair optimized
for expression in Saccharomyces cerevisiae

<400> SEQUENCE: 34

```
aaaggaggtg cacgcattat ggagaccact acgatacgat agctgcgttg ttgttgaagg     60
ggtttcttaa ggttgttttc gttgaaggta aatattggtc gtttttgtgc agcatattgt    120
cctctagatg caaactctgc aggtccattt gcagtaaagt gagttgcctc tcgaagaatc    180
attaatttcg tataaccgtc actattaaag tcagaaaata aattctgtcg tagacaatgt    240
taccataatg ttcttgtcca ttttgcatac actttaaata ttcatttgat ttctcagggt    300
tcatgatcat aataaattgc gcattcgcaa ggcggtagta ttataatggg gtccatcatt    360
ctgtagcaag aagttacagt acgctgttca agcgttaaac aagataagta atctcgaatg    420
aaacattcat atttcgcatg agccaacata cagttgctga gtaatcttca ttgcgcttat    480
ttatcggcat tgagattgta aaggaagtaa aacgcatttt tgcagatctg ttctcttatg    540
tatttttaat cgtccttgta tggaagtatc aaaggggacg ttcttcacct ccttggaagg    600
atcccttccc ttttacagtg cttcggaaaa gcacagcgtt gtccaaggga acaattttc    660
ttcaagttaa tgcataagaa atatcttttt ttatgtttag ctaagtaaaa gcagcttgga    720
gtaaaaaaaa aaatgagtaa atttctcgat ggattagttt ctcacaggta acataacaaa    780
aaccaagaaa agcccgcttc tgaaaactac agttgacttg tatgctaaag gccagacta    840
atgggaggag aaaagaaac gaatgtatat gctcatttac actctatatc accatatgga    900
ggataagttg ggctgagctt ctgatccaat ttattctatc cattagttgc tgatatgtcc    960
caccagccaa cacttgatag tatctactcg ccattcactt ccagcagcgc cagtagggtt   1020
gttgagctta gtaaaaatgt gcgcaccaca agcctacatg actccacgtc acatgaaacc   1080
acaccgtggg gccttgttgc gctaggaata ggatatgcga cgaagacgct tctgcttagt   1140
aaccacacca cattttcagg gggtcgatct gcttgcttcc tttactgtca cgagcggccc   1200
ataatcgcgc ttttttttta aaaggcgcga gacagcaaac aggaagctcg ggtttcaacc   1260
ttcggagtgg tcgcagatct ggagactgga tctttacaat acagtaaggc aagccaccat   1320
ctgcttctta ggtgcatgcg acggtatcca cgtgcagaac aacatagtct gaagaagggg   1380
gggaggagca tgttcattct ctgtagcagt aagagcttgg tgataatgac caaaactgga   1440
gtctcgaaat catataaata gacaatatat tttcacacaa tgagatttgt agtacagttc   1500
tattctctct cttgcataaa taagaaattc atcaagaact tggtttgata tttcaccaac   1560
acacacaaaa aacagtactt cactaaattt acacacaaaa caaaatgtcc tctgcttctg   1620
ctgctttgca aaaattcaga gctgaaagag ataccttcgg tgacttgcaa gttccagctg   1680
accgttactg gggtgctcaa actcaaagat ctttgcaaaa ctttgacatt ggtggtccaa   1740
ctgaaagaat gccagaacca ttaatcagag ctttcggtgt tttgaagaag ctgctgcca   1800
ccgtcaacat gacctacggt ttggacccaa aggttggtga agccatccaa aaggctgctg   1860
acgaagttat cgatggttct tgattgacc atttcccatt ggttgtctgg caaccggtt   1920
ctggtactca aaccaagatg aacgtcaatg aagtcatctc caacagagcc attgaattgt   1980
tgggtggtga attaggttcc aaggctccag tccacccaaa cgatcatgtc aacatgtctc   2040
aatcttccaa cgacactttc ccaactgcca tgcacgttgc tgccgttgtt gaaattcacg   2100
gtagattgat tccagctttg accactttga gagatgcttt gcaagccaaa tctgctgaat 2160
tcgaacacat catcaagatt ggtagaaccc acttgcaaga tgctacccca ttgactttag 2220
gtcaagaatt ctccggttac actcaacaat tgacctacgg tattgctcgt gttcaaggta 2280
ctttggaaag attatacaac ttggctcaag gtggtactgc tgtcggtact ggtttgaaca 2340
ccagaaaggg tttcgatgcc aaggttgctg aagccattgc ttccatcact ggtttaccat 2400
tcaagaccgc tccaaacaaa ttcgaagctt tggctgctca cgacgctttg gttgaagctc 2460
acggtgcttt gaacaccgtt gcttgttctt tgatgaagat tgccaacgat atccgttact 2520
tgggttctgg tccaagatgt ggtttaggtg aattgtctct accagaaaac gaaccaggtt 2580
cttccatcat gccaggtaag gtcaacccaa ctcaatgtga agctatgacc atggtttgtg 2640
ctcaagtcat gggtaacaac actgccatct ctgttgctgg ttccaacggt caattcgaat 2700
tgaatgtctt taaaccagtc atgatcaaga acttgatcca atccatcaga ttaatctctg 2760
acgcttccat ctctttcacc aagaactgtg ttgtcggtat tgaagctaac gaaaagaaga 2820
tctcctccat catgaacgaa tctttgatgt tggtcactgc tttgaaccct cacattggtt 2880
acgacaaggc tgccaagtgt gccaagaagg ctcacaagga aggtaccact ttgaaagaag 2940
ctgctctatc tttgggttac ttgacctctg aagaattcga ccaatgggtt agacctgagg 3000
acatgatttc tgccaaggat taaggcccgg gcataaagca atcttgatga ggataatgat 3060
tttttttga atatacataa atactaccgt ttttctgcta gattttgtga agacgtaaat 3120
aagtacatat tactttttaa gccaagacaa gattaagcat taactttacc cttttctctt 3180
ctaagtttca atactagtta tcactgttta aaagttatgg cgagaacgtc ggcggttaaa 3240
atatattacc ctgaacgtgg tgaattgaag ttctaggatg gtttaaagat ttttcctttt 3300
tgggaaataa gtaaacaata tattgctgcc tttgcaaaac gcacataccc acaatatgtg 3360
actattggca aagaacgcat tatcctttga agaggtggat actgatacta agagagtctc 3420
tattccggct ccacttttag tccagagatt acttgtcttc ttacgtatca gaacaagaaa 3480
gcatttccaa agtaattgca tttgcccttg agcagtatat atatactaag aagg 3534

<210> SEQ ID NO 35
<211> LENGTH: 2578
<212> TYPE: DNA
<213> ORGANISM: Artificial Sequence
<220> FEATURE:
<223> OTHER INFORMATION: nucleotide sequence of fragment 10 (Figure 1), which includes the 5' part of the Cre-recombinase
<400> SEQUENCE: 35
ttccaaagta attgcatttg cccttgagca gtatatatat actaagaagg tcgacctcga 60
gtaccgttcg tataatgtat gctatacgaa gttatattta aatcagtata gcgaccagca 120
ttcacatacg attgacgcat gatattactt tctgcgcact taacttcgca tctgggcaga 180
tgatgtcgag gcgaaaaaaa atataaatca cgctaacatt tgattaaaat agaacaacta 240
caatataaaa aaactataca aatgacaagt tcttgaaaac aagaatcttt ttattgtcag 300
tactgattag aaaaactcat cgagcatcaa atgaaactgc aatttattca tatcaggatt 360
atcaatacca tatttttgaa aaagccgttt ctgtaatgaa ggagaaaact caccgaggca 420
gttccatagg atggcaagat cctggtatcg gtctgcgatt ccgactcgtc caacatcaat 480
acaacctatt aatttcccct cgtcaaaaat aaggttatca agtgagaaat caccatgagt 540
gacgactgaa tccggtgaga atggcaaaag cttatgcatt tctttccaga cttgttcaac 600
aggccagcca ttacgctcgt catcaaaatc actcgcatca accaaaccgt tattcattcg    660
tgattgcgcc tgagcgagac gaaatacgcg atcgctgtta aaaggacaat tacaaacagg    720
aatcgaatgc aaccggcgca ggaacactgc cagcgcatca acaatatttt cacctgaatc    780
aggatattct tctaatacct ggaatgctgt tttgccgggg atcgcagtgg tgagtaacca    840
tgcatcatca ggagtacgga taaaatgctt gatggtcgga agaggcataa attccgtcag    900
ccagtttagt ctgaccatct catctgtaac atcattggca acgctacctt tgccatgttt    960
cagaaacaac tctggcgcat cgggcttccc atacaatcga tagattgtcg cacctgattg   1020
cccgacatta tcgcgagccc atttataccc atataaatca gcatccatgt tggaatttaa   1080
tcgcggcctc gaaacgtgag tcttttcctt acccatggtt gtttatgttc ggatgtgatg   1140
tgagaactgt atcctagcaa gattttaaaa ggaagtatat gaaagaagaa cctcagtggc   1200
aaatcctaac ctttatatt tctctacagg ggcgcggcgt ggggacaatt caacgcgtct   1260
gtgaggggag cgtttccctg ctcgcaggtc tgcagcgagg agccgtaatt tttgcttcgc   1320
gccgtgcggc catcaaaatg tatggatgca aatgattata catggggatg tatgggctaa   1380
atgtacgggc gacagtcaca tcatgcccct gagctgcgca cgtcaagact gtcaaggagg   1440
gtattctggg cctccatgtc atttaaatct agtacggatt agaagccgcc gagcgggtga   1500
cagccctccg aaggaagact ctcctccgtg cgtcctcgtc ttcaccggtc gcgttcctga   1560
aacgcagatg tgcctcgcgc cgcactgctc cgaacaataa agattctaca atactagctt   1620
ttatggttat gaagaggaaa aattggcagt aacctggccc cacaaacctt caaatgaacg   1680
aatcaaatta acaaccatag gatgataatg cgattagttt tttagcctta tttctggggt   1740
aattaatcag cgaagcgatg attttgatc tattaacaga tatataaatg caaaaactgc   1800
ataaccactt taactaatac tttcaacatt ttcggtttgt attacttctt attcaaatgt   1860
aataaaagta tcaacaaaaa attgttaata tacctctata ctttaacgtc aaggagaaaa   1920
aaccccggat tctagaacta gtggatcccc cgggctgcag gaattcgata tcaagcttat   1980
cgataccgtc gaggggcaga gccgatcctg tacactttac ttaaaaccat tatctgagtg   2040
ttaaatgtcc aatttactga ccgtacacca aaatttgcct gcattaccgg tcgatgcaac   2100
gagtgatgag gttcgcaaga acctgatgga catgttcagg gatcgccagg cgttttctga   2160
gcatacctgg aaaatgcttc tgtccgtttg ccggtcgtgg gcggcatggt gcaagttgaa   2220
taaccggaaa tggtttcccg cagaacctga agatgttcgc gattatcttc tatatcttca   2280
ggcgcgcggt ctggcagtaa aaactatcca gcaacatttg gccagctaa acatgcttca   2340 tcgtcggtcc gggctgccac gaccaagtga cagcaatgct gtttcactgg ttatgcggcg   2400
gatccgaaaa gaaaacgttg atgccggtga acgtgcaaaa caggctctag cgttcgaacg   2460
cactgatttc gaccaggttc gttcactcat ggaaaatagc gatcgctgcc aggatatacg   2520
taatctggca tttctgggga ttgcttataa caccctgtta cgtatagccg aaattgcc     2578
```

<210> SEQ ID NO 36
<211> LENGTH: 1263
<212> TYPE: DNA
<213> ORGANISM: Artificial Sequence
<220> FEATURE:
<223> OTHER INFORMATION: nucleotide sequence of fragment 11 (Figure 1),
      which includes the 3' part of the Cre-recombinase

<400> SEQUENCE: 36

```
cgttcactca tggaaaatag cgatcgctgc caggatatac gtaatctggc atttctgggg     60
```

```
attgcttata acaccctgtt acgtatagcc gaaattgcca ggatcagggt taaagatatc        120
tcacgtactg acggtgggag aatgttaatc catattggca gaacgaaaac gctggttagc        180
accgcaggtg tagagaaggc acttagcctg ggggtaacta aactggtcga gcgatggatt        240
tccgtctctg gtgtagctga tgatccgaat aactacctgt tttgccgggt cagaaaaaat        300
ggtgttgccg cgccatctgc caccagccag ctatcaactc gcgccctgga agggattttt        360
gaagcaactc atcgattgat ttacggcgct aaggatgact ctggtcagag atacctggcc        420
tggtctggac acagtgcccg tgtcggagcc gcgcgagata tggcccgcgc tggagtttca        480
ataccggaga tcatgcaagc tggtggctgg accaatgtaa atattgtcat gaactatatc        540
cgtaccctgg atagtgaaac aggggcaatg gtgcgcctgc tggaagatgg cgattagcca        600
ttaacgcgta atgattgct ataattattt gatatttatg gtgacatatg agaaaggat        660 tcaacatcga cggaaaatat gtagtgctgt ctgtaagcac taatattcag tcgccagccg        720
tcattgtcac tgtaaagctg agcgatgaaa tgcctgatat tgactcaata tccgttgcgt        780
ttcctgtcaa aagtatgcgt agtgctgaac atttcgtgat gaatgccacc gaggaagaag        840
cacggcgcgg ttttgcttaa agtgatgtct gagtttggcg aactcttggg taaggttgga        900
attgtcgacc tcgagtcatg taattagtta tgtcacgctt acattcacgc cctcccccca        960
catccgctct aaccgaaaag gaaggagtta gacaacctga agtctaggtc cctatttatt       1020
tttttatagt tatgttagta ttaagaacgt tatttatatt tcaaattttt cttttttttc       1080 tgtacgacg cgtgtacgca tgtaacatta tactgaaaac cttgcttgag aaggttttgg       1140
gacgctcgaa ggctttaatt tgcggccggt acataacttc gtataatgta tgctatacga       1200
acggtaggat ccggatggga cgtcagcact gtacttgttt ttgcgactag attgtaaatc       1260
att                                                                    1263
```

<210> SEQ ID NO 37
<211> LENGTH: 631
<212> TYPE: DNA
<213> ORGANISM: Artificial Sequence
<220> FEATURE:
<223> OTHER INFORMATION: nucleotide sequence of fragment 12 (Figure 1),
      which includes a region homologous to the YPRCtau3 locus

<400> SEQUENCE: 37

```
gatgggacgt cagcactgta cttgttttg cgactagatt gtaaatcatt ctttatttaa         60
tctctttctt taactactgc ttaaagtata atttggtccg tagtttaata actatactaa        120
gcgtaacaat gcatactgac attataagcc tgaacattac gagtttaagt tgtatgtagg        180
cgttctgtaa gaggttactg cgtaaattat caacgaatgc attggtgtat ttgcgaaagc        240
tacttctttt aacaagtatt tacataagaa taatggtgat ctgctcaact gatttggtga        300
taactctaac ttttttagca acaatttaaa agataattcg aacatatata acagtaggaa        360
gaatttgtgt acgtcaaatt aagataattt agcattacca aagttattaa cctaaacata        420
aaatatatat gagacacatg tggaaatcgt atgaaacaac tgttatgaaa ctgacaagaa        480
tgaatatata gagtaagctc cgcttgtaaa gaggaatcac ttaagtgtat aaatgtctcg        540
acgattactt tagatccaag attgatgatt gatattactc tgtaatactt aagctctttt        600
aatagctcac tgttgtatta cgggctcgag t                                      631
```

<210> SEQ ID NO 38
<211> LENGTH: 1334

<210> SEQ ID NO 38
<211> LENGTH: 1334
<212> TYPE: DNA
<213> ORGANISM: Artificial Sequence
<220> FEATURE:
<223> OTHER INFORMATION: nucleotide sequence of the PCR template for fragment 115 (Figure 3), fragment 14 (Figure 4) and fragment 117 (Figure 6), which includes the nourseothricin selection marker

<400> SEQUENCE: 38

```
tcgtacgctg caggtcgacg aattctaccg ttcgtataat gtatgctata cgaagttata    60
gatctgttta gcttgcctcg tcccgccgg gtcacccggc cagcgacatg gaggcccaga   120
ataccctcct tgacagtctt gacgtgcgca gctcaggggc atgatgtgac tgtcgcccgt   180
acatttagcc catacatccc catgtataat catttgcatc catacatttt gatggccgca   240
cggcgcgaag caaaaattac ggctcctcgc tgcagacctg cgagcaggga acgctcccc   300
tcacagacgc gttgaattgt ccccacgccg cgcccctgta gagaaatata aaaggttagg   360
atttgccact gaggttcttc tttcatatac ttccttttaa aatcttgcta ggatacagtt   420
ctcacatcac atccgaacat aaacaaccat gggtaccact cttgacgaca cggcttaccg   480
gtaccgcacc agtgtcccgg gggacgccga ggccatcgag gcactggatg ggtccttcac   540
caccgacacc gtcttccgcg tcaccgccac cggggacggc ttcaccctgc gggaggtgcc   600
ggtggacccg cccctgacca aggtgttccc cgacgacgaa tcggacgacg aatcggacga   660
cggggaggac ggcgacccgg actcccggac gttcgtcgcg tacggggacg acggcgacct   720
ggcgggcttc gtggtcgtct cgtactccgg ctggaaccgc cggctgaccg tcgaggacat   780
cgaggtcgcc ccggagcacc ggggcacgg ggtcgggcgc gcgttgatgg ggctcgcgac   840
ggagttcgcc cgcgagcggg gcgccgggca cctctggctg gaggtcacca acgtcaacgc   900
accggcgatc cacgcgtacc ggcggatggg gttcacccte tgcggcctgg acaccgccct   960
gtacgacggc accgcctcgg acggcgagca ggcgctctac atgagcatgc cctgccccta  1020
atcagtactg acaataaaaa gattcttgtt ttcaagaact tgtcatttgt atagtttttt  1080
tatattgtag ttgttctatt ttaatcaaat gttagcgtga tttatatttt ttttcgcctc  1140
gacatcatct gcccagatgc gaagttaagt gcgcagaaag taatatcatg cgtcaatcgt  1200
atgtgaatgc tggtcgctat actgctgtcg attcgatact aacgccgcca tccagtgtcg  1260
aaaacgagct cataacttcg tataatgtat gctatacgaa cggtagaatt cgatatcaga  1320
tccactagtg gcct                                                    1334
```

<210> SEQ ID NO 39
<211> LENGTH: 340
<212> TYPE: PRT
<213> ORGANISM: Artificial Sequence
<220> FEATURE:
<223> OTHER INFORMATION: MDH3 lacking 3C-terminal peroxisomal targeting sequence

<400> SEQUENCE: 39

```
Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
        35                  40                  45

Asn Thr Asn Ser Ser Cys Val Gly Tyr Asp Lys Asp Ser Ile Glu Asn
    50                  55                  60

Thr Leu Ser Asn Ala Gln Val Val Leu Ile Pro Ala Gly Val Pro Arg
```

```
            65                  70                  75                  80
Lys Pro Gly Leu Thr Arg Asp Asp Leu Phe Lys Met Asn Ala Gly Ile
                    85                  90                  95

Val Lys Ser Leu Val Thr Ala Val Gly Lys Phe Ala Pro Asn Ala Arg
                100                 105                 110

Ile Leu Val Ile Ser Asn Pro Val Asn Ser Leu Val Pro Ile Ala Val
                115                 120                 125

Glu Thr Leu Lys Lys Met Gly Lys Phe Lys Pro Gly Asn Val Met Gly
            130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175

Met His Arg Lys Val Thr Val Ile Gly Gly His Ser Gly Glu Thr Ile
                180                 185                 190

Ile Pro Ile Ile Thr Asp Lys Ser Leu Val Phe Gln Leu Asp Lys Gln
            195                 200                 205

Tyr Glu His Phe Ile His Arg Val Gln Phe Gly Gly Asp Glu Ile Val
210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
        275                 280                 285

Phe Ser Leu Pro Ile Val Leu Arg Asn Gly Ser Val Val Ser Ile Asp
            290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 40
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 113 (Figure 2)

<400> SEQUENCE: 40
agaaagcctg tatgcgaagc cacaatcctt tccaacagac catactaagt acaggtgatt    60
gtatgtgggc ttatg                                                    75

<210> SEQ ID NO 41
<211> LENGTH: 29
<212> TYPE: DNA
<213> ORGANISM: Artificial Sequence
<220> FEATURE:
<223> OTHER INFORMATION: nucleotide sequence of the primer used to
      generate fragment 113 (Figure 2)

<400> SEQUENCE: 41
```
acattattgt aaaaacggag tagaaaggg                                29

<210> SEQ ID NO 42
<211> LENGTH: 2927
<212> TYPE: DNA
<213> ORGANISM: Artificial Sequence
<220> FEATURE:
<223> OTHER INFORMATION: nucleotide sequence of fragment 114 (Figure 3),
      which includes the expression cassette of ZWF1 from S. cerevisiae
      codon pair optimized for expression in S. cerevisiae

<400> SEQUENCE: 42

```
atccgtacac gtttgtgccg aacccgaagt attgcaacag gtcgaagttc gtgccaaagg    60
gggggcaggg acagggatac gacaagggct ggggaaaaaa aaaagatag atacgattgg   120
ccgggtaagc ctggggaaat gtagcaagtg cgggtaagtt aaaaggtaac cacgtgactc   180
cggaagagtc acgtggttac ggacttttt ctctagatct cagcttttta tcggtcttac    240
cctgccctcc tgccccctgc cccttcccctt tgccccaaaa agaaaggaaa tctgttggat   300
ttcgctcagg ccatcccttt cgttaatatc ggttatcgct ttacacactg cacatccttc    360
tgtccaaaag gaatccagaa gtttagcttt tccttccttt cccacagaca ttagcctagg    420
ccctctctca tcatttgcat gcctcagcca atgtaccaag aataacgcaa cgaggttggg    480
aaattttaac ccaacaatcg atgcagatgt gacaagagat tagacacgtt ccagatacca    540
gattacacag cttgtgctag cagagtgaca tatggtggtg ttgtgtctcg tttagtacct    600
gtaatcgaga gtgttcaaat cagtcgattt gaacacccctt actgccactg aatattgatt    660
gaataccgtt tattgaaggt tttatgagtg atcttctttc ggtccaggac aatttgttga    720
gcttttcta tgtagagttc cgtccctttt ttttttttt ttgctttctc gcacttacta       780
gcactatttt tttttcacac actaaaaacac tttattttaa tctatatata tatatatata    840
tatatgtagg aatggaatca cagacatttg atactcatcc tcatccttat taattcttgt    900
tttaatttgt ttgacttagc caaaccacca atctcaaccc atcgtatttc aggtattgtg    960
tgtctagtgt gtctctggta tacggaaata agtgccagaa gtaaggaaga aacaaagaac   1020
aagtgtctga atactactag cctctctttt cataatgagt gaaggccccg tcaaattcga   1080
aaaaaatacc gtcatatctg tctttggtgc gtcaggtgat ctggcaaaga agaagacttt   1140
tcccgcctta tttgggcttt tcagagaagg ttaccttgat ccatctacca agatcttcgg   1200
ttatgcccgg tccaaattgt ccatggagga ggacctgaag tcccgtgtcc taccccactt   1260
gaaaaaccct cacggtgaag ccgatgactc taaggtcgaa cagttcttca agatggtcag   1320
ctacatttcg ggaaattacg acacagatga aggcttcgac gaattaagaa cgcagatcga   1380
gaaattcgag aaaagtgcca acgtcgatgt cccacaccgt ctcttctatc tggccttgcc   1440
gccaagcgtt tttttgacgg tggccaagca gatcaagagt cgtgtgtacg cagagaatgg   1500
catcaccgt gtaatcgtag agaaaccttt cggccacgac ctggcctctg ccagggagct   1560
gcaaaaaaac ctggggcccc tctttaaaga agaagagttg tacagaattg accattactt   1620
gggtaaagag ttggtcaaga atcttttagt cttgaggttc ggtaaccagt ttttgaatgc   1680
ctcgtggaat agagacaaca ttcaaagcgt tcagatttcg tttaaagaga ggttcggcac   1740
cgaaggccgt ggcggctatt tcgactctat aggcataatc agagacgtga tgcagaacca   1800
tctgttacaa atcatgactc tcttgactat ggaaagaccg gtgtcttttg acccggaatc   1860
tattcgtgac gaaaaggtta aggttctaaa ggccgtggcc cccatcgaca cggacgacgt   1920
cctcttgggc cagtacggta aatctgagga cgggtctaag cccgcctacg tggatgatga   1980
```

```
cactgtagac aaggactcta aatgtgtcac ttttgcagca atgactttca acatcgaaaa   2040
cgagcgttgg gagggcgtcc ccatcatgat gcgtgccggt aaggctttga atgagtccaa   2100
ggtggagatc agactgcagt acaaagcggt cgcatcgggt gtcttcaaag acattccaaa   2160
taacgaactg gtcatcagag tgcagcccga tgccgctgtg tacctaaagt ttaatgctaa   2220
gaccgctggt ctgtcaaatg ctacccaagt cacagatctg aatctaactt acgcaagcag   2280
gtaccaagac ttttggattc cagaggctta cgaggtgttg ataagagacg ccctactggg   2340
tgaccattcc aactttgtca gagatgacga attggatatc agttggggca tattcacccc   2400
attactgaag cacatagagc gtccggacgg tccaacaccg gaaatttacc cctacggatc   2460
aagaggtcca aagggattga aggaatatat gcaaaaacac aagtatgtta tgcccgaaaa   2520
gcacccttac gcttggcccg tgactaagcc agaagatacg aaggataatt aaaggagatt   2580
gataagactt ttctagttgc atatctttta tatttaaatc ttatctatta gttaattttt   2640
tgtaatttat ccttatatat agtctggtta ttctaaaata tcatttcagt atctaaaaat   2700
tccctctttt tttcagttat atcttaacag gcgacagtcc aaatgttgat ttatcccagt   2760
ccgattcatc agggttgtga agcattttgt caatggtcga aatcacatca gtaatagtgc   2820
ctcttacttg cctcatagaa tttctttctc ttaacgtcac cgtttggtct tttcctcacc   2880
cgatcccgaa gaaagtccaa ctccagttcg attccctgct ttcgagt                 2927

<210> SEQ ID NO 43
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 114 (Figure 3)

<400> SEQUENCE: 43
atccgtacac gtttgtgccg                                                 20

<210> SEQ ID NO 44
<211> LENGTH: 22
<212> TYPE: DNA
<213> ORGANISM: Artificial Sequence
<220> FEATURE:
<223> OTHER INFORMATION: nucleotide sequence of the primer used to
      generate fragment 114 (Figure 3)

<400> SEQUENCE: 44
actcgaaagc agggaatcga ac                                              22

<210> SEQ ID NO 45
<211> LENGTH: 79
<212> TYPE: DNA
<213> ORGANISM: Artificial Sequence
<220> FEATURE:
<223> OTHER INFORMATION: nucleotide sequence of the primer used to
      generate fragment 115 (Figure 3)

<400> SEQUENCE: 45
acccgatccc gaagaaagtc caactccagt tcgattccct gctttcgagt tcgtacgctg     60
caggtcgacg aattctacc                                                  79

<210> SEQ ID NO 46
<211> LENGTH: 1180
<212> TYPE: PRT
<213> ORGANISM: Saccharomyces cerevisiae
```

<400> SEQUENCE: 46

Met Ser Ser Ser Lys Ile Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Gly Gln Tyr Thr Pro Val Gly Ala
65                  70                  75                  80

Tyr Leu Ala Met Asp Glu Ile Ile Glu Ile Ala Lys Lys His Lys Val
                85                  90                  95

Asp Phe Ile His Pro Gly Tyr Gly Phe Leu Ser Glu Asn Ser Glu Phe
                100                 105                 110

Ala Asp Lys Val Val Lys Ala Gly Ile Thr Trp Ile Gly Pro Pro Ala
            115                 120                 125

Glu Val Ile Glu Ser Val Gly Asp Lys Val Ser Ala Arg His Leu Ala
130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
            180                 185                 190

Arg Glu Gly Asp Asp Val Ala Asp Ala Phe Gln Arg Ala Thr Ser Glu
        195                 200                 205

Ala Arg Thr Ala Phe Gly Asn Gly Thr Cys Phe Val Glu Arg Phe Leu
210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg Arg His
                245                 250                 255

Gln Lys Val Val Glu Val Ala Pro Ala Lys Thr Leu Pro Arg Glu Val
            260                 265                 270

Arg Asp Ala Ile Leu Thr Asp Ala Val Lys Leu Ala Lys Val Cys Gly
        275                 280                 285

Tyr Arg Asn Ala Gly Thr Ala Glu Phe Leu Val Asp Asn Gln Asn Arg
290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln Ile
                325                 330                 335

Ala Ala Gly Ala Thr Leu Thr Gln Leu Gly Leu Leu Gln Asp Lys Ile
            340                 345                 350

Thr Thr Arg Gly Phe Ser Ile Gln Cys Arg Ile Thr Thr Glu Asp Pro
        355                 360                 365

Ser Lys Asn Phe Gln Pro Asp Thr Gly Arg Leu Glu Val Tyr Arg Ser
    370                 375                 380

Ala Gly Gly Asn Gly Val Arg Leu Asp Gly Gly Asn Ala Tyr Ala Gly
385                 390                 395                 400

Ala Thr Ile Ser Pro His Tyr Asp Ser Met Leu Val Lys Cys Ser Cys

```
                405                 410                 415
Ser Gly Ser Thr Tyr Glu Ile Val Arg Arg Lys Met Ile Arg Ala Leu
            420                 425                 430

Ile Glu Phe Arg Ile Arg Gly Val Lys Thr Asn Ile Pro Phe Leu Leu
            435                 440                 445

Thr Leu Leu Thr Asn Pro Val Phe Ile Glu Gly Thr Tyr Trp Thr Thr
            450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
            485                 490                 495

Ser Ser Ile Lys Gly Gln Ile Gly Leu Pro Lys Leu Lys Ser Asn Pro
            500                 505                 510

Ser Val Pro His Leu His Asp Ala Gln Gly Asn Val Ile Asn Val Thr
            515                 520                 525

Lys Ser Ala Pro Pro Ser Gly Trp Arg Gln Val Leu Leu Glu Lys Gly
            530                 535                 540

Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
            565                 570                 575

Val Arg Thr His Asp Leu Ala Thr Ile Ala Pro Thr Thr Ala His Ala
            580                 585                 590

Leu Ala Gly Ala Phe Ala Leu Glu Cys Trp Gly Gly Ala Thr Phe Asp
            595                 600                 605

Val Ala Met Arg Phe Leu His Glu Asp Pro Trp Glu Arg Leu Arg Lys
            610                 615                 620

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
            645                 650                 655

Phe Val Lys Gln Ala Lys Asp Asn Gly Val Asp Ile Phe Arg Val Phe
            660                 665                 670

Asp Ala Leu Asn Asp Leu Glu Gln Leu Lys Val Gly Val Asn Ala Val
            675                 680                 685

Lys Lys Ala Gly Gly Val Val Glu Ala Thr Val Cys Tyr Ser Gly Asp
            690                 695                 700

Met Leu Gln Pro Gly Lys Lys Tyr Asn Leu Asp Tyr Tyr Leu Glu Val
705                 710                 715                 720

Val Glu Lys Ile Val Gln Met Gly Thr His Ile Leu Gly Ile Lys Asp
            725                 730                 735

Met Ala Gly Thr Met Lys Pro Ala Ala Ala Lys Leu Leu Ile Gly Ser
            740                 745                 750

Leu Arg Thr Arg Tyr Pro Asp Leu Pro Ile His Val His Ser His Asp
            755                 760                 765

Ser Ala Gly Thr Ala Val Ala Ser Met Thr Ala Cys Ala Leu Ala Gly
            770                 775                 780

Ala Asp Val Val Asp Val Ala Ile Asn Ser Met Ser Gly Leu Thr Ser
785                 790                 795                 800

Gln Pro Ser Ile Asn Ala Leu Leu Ala Ser Leu Glu Gly Asn Ile Asp
            805                 810                 815

Thr Gly Ile Asn Val Glu His Val Arg Glu Leu Asp Ala Tyr Trp Ala
            820                 825                 830
```

Glu Met Arg Leu Leu Tyr Ser Cys Phe Glu Ala Asp Leu Lys Gly Pro
            835                 840                 845

Asp Pro Glu Val Tyr Gln His Glu Ile Pro Gly Gly Gln Leu Thr Asn
    850                 855                 860

Leu Leu Phe Gln Ala Gln Gln Leu Gly Leu Gly Glu Gln Trp Ala Glu
865                 870                 875                 880

Thr Lys Arg Ala Tyr Arg Glu Ala Asn Tyr Leu Leu Gly Asp Ile Val
                885                 890                 895

Lys Val Thr Pro Thr Ser Lys Val Val Gly Asp Leu Ala Gln Phe Met
            900                 905                 910

Val Ser Asn Lys Leu Thr Ser Asp Asp Ile Arg Arg Leu Ala Asn Ser
            915                 920                 925

Leu Asp Phe Pro Asp Ser Val Met Asp Phe Phe Glu Gly Leu Ile Gly
        930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
                965                 970                 975

Phe Asp Leu Glu Lys Ile Arg Glu Asp Leu Gln Asn Arg Phe Gly Asp
            980                 985                 990

Ile Asp Glu Cys Asp Val Ala Ser Tyr Asn Met Tyr Pro Arg Val Tyr
            995                 1000                1005

Glu Asp Phe Gln Lys Ile Arg Glu Thr Tyr Gly Asp Leu Ser Val
1010                1015                1020

Leu Pro Thr Lys Asn Phe Leu Ala Pro Ala Glu Pro Asp Glu Glu
    1025                1030                1035

Ile Glu Val Thr Ile Glu Gln Gly Lys Thr Leu Ile Ile Lys Leu
    1040                1045                1050

Gln Ala Val Gly Asp Leu Asn Lys Lys Thr Gly Gln Arg Glu Val
    1055                1060                1065

Tyr Phe Glu Leu Asn Gly Glu Leu Arg Lys Ile Arg Val Ala Asp
    1070                1075                1080

Lys Ser Gln Asn Ile Gln Ser Val Ala Lys Pro Lys Ala Asp Val
    1085                1090                1095

His Asp Thr His Gln Ile Gly Ala Pro Met Ala Gly Val Ile Ile
    1100                1105                1110

Glu Val Lys Val His Lys Gly Ser Leu Val Lys Lys Gly Glu Ser
    1115                1120                1125

Ile Ala Val Leu Ser Ala Met Lys Met Glu Met Val Val Ser Ser
    1130                1135                1140

Pro Ala Asp Gly Gln Val Lys Asp Val Phe Ile Arg Asp Gly Glu
    1145                1150                1155

Ser Val Asp Ala Ser Asp Leu Leu Val Val Leu Glu Glu Glu Thr
    1160                1165                1170

Leu Pro Pro Ser Gln Lys Lys
    1175                1180

<210> SEQ ID NO 47
<211> LENGTH: 538
<212> TYPE: PRT
<213> ORGANISM: Artificial Sequence
<220> FEATURE:
<223> OTHER INFORMATION: amino acid sequence of phosphoenolpyruvate
      carboxykinase from Actinobacillus succinogenes, with EGY to DAF
      modification at position 120-122

<400> SEQUENCE: 47

| | | | | | | | | | | | | | | |
|---|---|---|---|---|---|---|---|---|---|---|---|---|---|---|
| Met | Thr | Asp | Leu | Asn | Lys | Leu | Val | Lys | Glu | Leu | Asn | Asp | Leu | Gly | Leu |
| 1 | | | | 5 | | | | | 10 | | | | | 15 | |

| Thr | Asp | Val | Lys | Glu | Ile | Val | Tyr | Asn | Pro | Ser | Tyr | Glu | Gln | Leu | Phe |
|---|---|---|---|---|---|---|---|---|---|---|---|---|---|---|---|
| | | | 20 | | | | | 25 | | | | | 30 | | |

| Glu | Glu | Glu | Thr | Lys | Pro | Gly | Leu | Glu | Gly | Phe | Asp | Lys | Gly | Thr | Leu |
|---|---|---|---|---|---|---|---|---|---|---|---|---|---|---|---|
| | | | 35 | | | | | 40 | | | | | 45 | | |

| Thr | Thr | Leu | Gly | Ala | Val | Ala | Val | Asp | Thr | Gly | Ile | Phe | Thr | Gly | Arg |
|---|---|---|---|---|---|---|---|---|---|---|---|---|---|---|---|
| | 50 | | | | | 55 | | | | | 60 | | | | |

| Ser | Pro | Lys | Asp | Lys | Tyr | Ile | Val | Cys | Asp | Glu | Thr | Thr | Lys | Asp | Thr |
|---|---|---|---|---|---|---|---|---|---|---|---|---|---|---|---|
| 65 | | | | | 70 | | | | | 75 | | | | | 80 |

| Val | Trp | Trp | Asn | Ser | Glu | Ala | Ala | Lys | Asn | Asp | Asn | Lys | Pro | Met | Thr |
|---|---|---|---|---|---|---|---|---|---|---|---|---|---|---|---|
| | | | | 85 | | | | | 90 | | | | | 95 | |

| Gln | Glu | Thr | Trp | Lys | Ser | Leu | Arg | Glu | Leu | Val | Ala | Lys | Gln | Leu | Ser |
|---|---|---|---|---|---|---|---|---|---|---|---|---|---|---|---|
| | | | | 100 | | | | | 105 | | | | | 110 | |

| Gly | Lys | Arg | Leu | Phe | Val | Val | Asp | Ala | Phe | Cys | Gly | Ala | Ser | Glu | Lys |
|---|---|---|---|---|---|---|---|---|---|---|---|---|---|---|---|
| | | | 115 | | | | | 120 | | | | | 125 | | |

| His | Arg | Ile | Gly | Val | Arg | Met | Val | Thr | Glu | Val | Ala | Trp | Gln | Ala | His |
|---|---|---|---|---|---|---|---|---|---|---|---|---|---|---|---|
| | | 130 | | | | | 135 | | | | | 140 | | | |

| Phe | Val | Lys | Asn | Met | Phe | Ile | Arg | Pro | Thr | Asp | Glu | Glu | Leu | Lys | Asn |
|---|---|---|---|---|---|---|---|---|---|---|---|---|---|---|---|
| 145 | | | | | 150 | | | | | 155 | | | | | 160 |

| Phe | Lys | Ala | Asp | Phe | Thr | Val | Leu | Asn | Gly | Ala | Lys | Cys | Thr | Asn | Pro |
|---|---|---|---|---|---|---|---|---|---|---|---|---|---|---|---|
| | | | | 165 | | | | | 170 | | | | | 175 | |

| Asn | Trp | Lys | Glu | Gln | Gly | Leu | Asn | Ser | Glu | Asn | Phe | Val | Ala | Phe | Asn |
|---|---|---|---|---|---|---|---|---|---|---|---|---|---|---|---|
| | | | 180 | | | | | 185 | | | | | 190 | | |

| Ile | Thr | Glu | Gly | Ile | Gln | Leu | Ile | Gly | Gly | Thr | Trp | Tyr | Gly | Gly | Glu |
|---|---|---|---|---|---|---|---|---|---|---|---|---|---|---|---|
| | | 195 | | | | | 200 | | | | | 205 | | | |

| Met | Lys | Lys | Gly | Met | Phe | Ser | Met | Met | Asn | Tyr | Phe | Leu | Pro | Leu | Lys |
|---|---|---|---|---|---|---|---|---|---|---|---|---|---|---|---|
| | 210 | | | | | 215 | | | | | 220 | | | | |

| Gly | Val | Ala | Ser | Met | His | Cys | Ser | Ala | Asn | Val | Gly | Lys | Asp | Gly | Asp |
|---|---|---|---|---|---|---|---|---|---|---|---|---|---|---|---|
| 225 | | | | | 230 | | | | | 235 | | | | | 240 |

| Val | Ala | Ile | Phe | Phe | Gly | Leu | Ser | Gly | Thr | Gly | Lys | Thr | Thr | Leu | Ser |
|---|---|---|---|---|---|---|---|---|---|---|---|---|---|---|---|
| | | | | 245 | | | | | 250 | | | | | 255 | |

| Thr | Asp | Pro | Lys | Arg | Gln | Leu | Ile | Gly | Asp | Asp | Glu | His | Gly | Trp | Asp |
|---|---|---|---|---|---|---|---|---|---|---|---|---|---|---|---|
| | | | 260 | | | | | 265 | | | | | 270 | | |

| Glu | Ser | Gly | Val | Phe | Asn | Phe | Glu | Gly | Gly | Cys | Tyr | Ala | Lys | Thr | Ile |
|---|---|---|---|---|---|---|---|---|---|---|---|---|---|---|---|
| | | 275 | | | | | 280 | | | | | 285 | | | |

| Asn | Leu | Ser | Gln | Glu | Asn | Glu | Pro | Asp | Ile | Tyr | Gly | Ala | Ile | Arg | Arg |
|---|---|---|---|---|---|---|---|---|---|---|---|---|---|---|---|
| | 290 | | | | | 295 | | | | | 300 | | | | |

| Asp | Ala | Leu | Leu | Glu | Asn | Val | Val | Val | Arg | Ala | Asp | Gly | Ser | Val | Asp |
|---|---|---|---|---|---|---|---|---|---|---|---|---|---|---|---|
| 305 | | | | | 310 | | | | | 315 | | | | | 320 |

| Phe | Asp | Asp | Gly | Ser | Lys | Thr | Glu | Asn | Thr | Arg | Val | Ser | Tyr | Pro | Ile |
|---|---|---|---|---|---|---|---|---|---|---|---|---|---|---|---|
| | | | | 325 | | | | | 330 | | | | | 335 | |

| Tyr | His | Ile | Asp | Asn | Ile | Val | Arg | Pro | Val | Ser | Lys | Ala | Gly | His | Ala |
|---|---|---|---|---|---|---|---|---|---|---|---|---|---|---|---|
| | | | 340 | | | | | 345 | | | | | 350 | | |

| Thr | Lys | Val | Ile | Phe | Leu | Thr | Ala | Asp | Ala | Phe | Gly | Val | Leu | Pro | Pro |
|---|---|---|---|---|---|---|---|---|---|---|---|---|---|---|---|
| | | | 355 | | | | | 360 | | | | | 365 | | |

| Val | Ser | Lys | Leu | Thr | Pro | Glu | Gln | Thr | Glu | Tyr | Tyr | Phe | Leu | Ser | Gly |
|---|---|---|---|---|---|---|---|---|---|---|---|---|---|---|---|
| | 370 | | | | | 375 | | | | | 380 | | | | |

| Phe | Thr | Ala | Lys | Leu | Ala | Gly | Thr | Glu | Arg | Gly | Val | Thr | Glu | Pro | Thr |
|---|---|---|---|---|---|---|---|---|---|---|---|---|---|---|---|
| 385 | | | | | 390 | | | | | 395 | | | | | 400 |

| Pro | Thr | Phe | Ser | Ala | Cys | Phe | Gly | Ala | Ala | Phe | Leu | Ser | Leu | His | Pro |
|---|---|---|---|---|---|---|---|---|---|---|---|---|---|---|---|

```
            405                 410                 415
Ile Gln Tyr Ala Asp Val Leu Val Glu Arg Met Lys Ala Ser Gly Ala
            420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
            485                 490                 495

Thr Tyr Ala Asp Lys Ala Gln Trp Gln Val Lys Ala Glu Asp Leu Ala
            500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
            530                 535

<210> SEQ ID NO 48
<211> LENGTH: 548
<212> TYPE: PRT
<213> ORGANISM: Escherichia coli

<400> SEQUENCE: 48

Met Ser Asn Lys Pro Phe Ile Tyr Gln Ala Pro Phe Pro Met Gly Lys
1               5                   10                  15

Asp Asn Thr Glu Tyr Tyr Leu Leu Thr Ser Asp Tyr Val Ser Val Ala
            20                  25                  30

Asp Phe Asp Gly Glu Thr Ile Leu Lys Val Glu Pro Glu Ala Leu Thr
        35                  40                  45

Leu Leu Ala Gln Gln Ala Phe His Asp Ala Ser Phe Met Leu Arg Pro
    50                  55                  60

Ala His Gln Lys Gln Val Ala Ala Ile Leu His Asp Pro Glu Ala Ser
65                  70                  75                  80

Glu Asn Asp Lys Tyr Val Ala Leu Gln Phe Leu Arg Asn Ser Glu Ile
                85                  90                  95

Ala Ala Lys Gly Val Leu Pro Thr Cys Gln Asp Thr Gly Thr Ala Ile
            100                 105                 110

Ile Val Gly Lys Lys Gly Gln Arg Val Trp Thr Gly Gly Gly Asp Glu
        115                 120                 125

Glu Thr Leu Ser Lys Gly Val Tyr Asn Thr Tyr Ile Glu Asp Asn Leu
    130                 135                 140

Arg Tyr Ser Gln Asn Ala Ala Leu Asp Met Tyr Lys Glu Val Asn Thr
145                 150                 155                 160

Gly Thr Asn Leu Pro Ala Gln Ile Asp Leu Tyr Ala Val Asp Gly Asp
                165                 170                 175

Glu Tyr Lys Phe Leu Cys Val Ala Lys Gly Gly Ser Ala Asn Lys
            180                 185                 190

Thr Tyr Leu Tyr Gln Glu Thr Lys Ala Leu Leu Thr Pro Gly Lys Leu
        195                 200                 205

Lys Asn Phe Leu Val Glu Lys Met Arg Thr Leu Gly Thr Ala Ala Cys
    210                 215                 220

Pro Pro Tyr His Ile Ala Phe Val Ile Gly Gly Thr Ser Ala Glu Thr
225                 230                 235                 240
```

```
Asn Leu Lys Thr Val Lys Leu Ala Ser Ala His Tyr Tyr Asp Glu Leu
                245                 250                 255

Pro Thr Glu Gly Asn Glu His Gly Gln Ala Phe Arg Asp Val Gln Leu
            260                 265                 270

Glu Gln Glu Leu Leu Glu Glu Ala Gln Lys Leu Gly Leu Gly Ala Gln
        275                 280                 285

Phe Gly Gly Lys Tyr Phe Ala His Asp Ile Arg Val Ile Arg Leu Pro
    290                 295                 300

Arg His Gly Ala Ser Cys Pro Val Gly Met Gly Val Ser Cys Ser Ala
305                 310                 315                 320

Asp Arg Asn Ile Lys Ala Lys Ile Asn Arg Glu Gly Ile Trp Ile Glu
                325                 330                 335

Lys Leu Glu His Asn Pro Gly Gln Tyr Ile Pro Gln Glu Leu Arg Gln
            340                 345                 350

Ala Gly Glu Gly Glu Ala Val Lys Val Asp Leu Asn Arg Pro Met Lys
        355                 360                 365

Glu Ile Leu Ala Gln Leu Ser Gln Tyr Pro Val Ser Thr Arg Leu Ser
    370                 375                 380

Leu Thr Gly Thr Ile Ile Val Gly Arg Asp Ile Ala His Ala Lys Leu
385                 390                 395                 400

Lys Glu Leu Ile Asp Ala Gly Lys Glu Leu Pro Gln Tyr Ile Lys Asp
                405                 410                 415

His Pro Ile Tyr Tyr Ala Gly Pro Ala Lys Thr Pro Ala Gly Tyr Pro
            420                 425                 430

Ser Gly Ser Leu Gly Pro Thr Thr Ala Gly Arg Met Asp Ser Tyr Val
        435                 440                 445

Asp Leu Leu Gln Ser His Gly Gly Ser Met Ile Met Leu Ala Lys Gly
    450                 455                 460

Asn Arg Ser Gln Gln Val Thr Asp Ala Cys His Lys His Gly Gly Phe
465                 470                 475                 480

Tyr Leu Gly Ser Ile Gly Gly Pro Ala Ala Val Leu Ala Gln Gln Ser
                485                 490                 495

Ile Lys His Leu Glu Cys Val Ala Tyr Pro Glu Leu Gly Met Glu Ala
            500                 505                 510

Ile Trp Lys Ile Glu Val Glu Asp Phe Pro Ala Phe Ile Leu Val Asp
        515                 520                 525

Asp Lys Gly Asn Asp Phe Phe Gln Gln Ile Val Asn Lys Gln Cys Ala
    530                 535                 540

Asn Cys Thr Lys
545

<210> SEQ ID NO 49
<211> LENGTH: 472
<212> TYPE: PRT
<213> ORGANISM: Artificial Sequence
<220> FEATURE:
<223> OTHER INFORMATION: amino acid sequence of fumarase from Rhizopus
      oryzae, lacking the first 23 N-terminal amino acids

<400> SEQUENCE: 49

Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45
```

```
Met Pro Glu Pro Leu Ile Arg Ala Phe Gly Val Leu Lys Ala Ala
    50                  55                  60
Ala Thr Val Asn Met Thr Tyr Gly Leu Asp Pro Lys Val Gly Glu Ala
65                  70                  75                  80
Ile Gln Lys Ala Ala Asp Glu Val Ile Asp Gly Ser Leu Ile Asp His
                85                  90                  95
Phe Pro Leu Val Val Trp Gln Thr Gly Ser Gly Thr Gln Thr Lys Met
                100                 105                 110
Asn Val Asn Glu Val Ile Ser Asn Arg Ala Ile Glu Leu Leu Gly Gly
            115                 120                 125
Glu Leu Gly Ser Lys Ala Pro Val His Pro Asn Asp His Val Asn Met
    130                 135                 140
Ser Gln Ser Ser Asn Asp Thr Phe Pro Thr Ala Met His Val Ala Ala
145                 150                 155                 160
Val Val Glu Ile His Gly Arg Leu Ile Pro Ala Leu Thr Thr Leu Arg
                165                 170                 175
Asp Ala Leu Gln Ala Lys Ser Ala Glu Phe Glu His Ile Ile Lys Ile
                180                 185                 190
Gly Arg Thr His Leu Gln Asp Ala Thr Pro Leu Thr Leu Gly Gln Glu
        195                 200                 205
Phe Ser Gly Tyr Thr Gln Gln Leu Thr Tyr Gly Ile Ala Arg Val Gln
    210                 215                 220
Gly Thr Leu Glu Arg Leu Tyr Asn Leu Ala Gln Gly Gly Thr Ala Val
225                 230                 235                 240
Gly Thr Gly Leu Asn Thr Arg Lys Gly Phe Asp Ala Lys Val Ala Glu
                245                 250                 255
Ala Ile Ala Ser Ile Thr Gly Leu Pro Phe Lys Thr Ala Pro Asn Lys
                260                 265                 270
Phe Glu Ala Leu Ala Ala His Asp Ala Leu Val Glu Ala His Gly Ala
            275                 280                 285
Leu Asn Thr Val Ala Cys Ser Leu Met Lys Ile Ala Asn Asp Ile Arg
    290                 295                 300
Tyr Leu Gly Ser Gly Pro Arg Cys Gly Leu Gly Glu Leu Ser Leu Pro
305                 310                 315                 320
Glu Asn Glu Pro Gly Ser Ser Ile Met Pro Gly Lys Val Asn Pro Thr
                325                 330                 335
Gln Cys Glu Ala Met Thr Met Val Cys Ala Gln Val Met Gly Asn Asn
                340                 345                 350
Thr Ala Ile Ser Val Ala Gly Ser Asn Gly Gln Phe Glu Leu Asn Val
            355                 360                 365
Phe Lys Pro Val Met Ile Lys Asn Leu Ile Gln Ser Ile Arg Leu Ile
    370                 375                 380
Ser Asp Ala Ser Ile Ser Phe Thr Lys Asn Cys Val Val Gly Ile Glu
385                 390                 395                 400
Ala Asn Glu Lys Lys Ile Ser Ser Ile Met Asn Glu Ser Leu Met Leu
                405                 410                 415
Val Thr Ala Leu Asn Pro His Ile Gly Tyr Asp Lys Ala Ala Lys Cys
            420                 425                 430
Ala Lys Lys Ala His Lys Glu Gly Thr Thr Leu Lys Glu Ala Ala Leu
    435                 440                 445
Ser Leu Gly Tyr Leu Thr Ser Glu Glu Phe Asp Gln Trp Val Arg Pro
    450                 455                 460
```

Glu Asp Met Ile Ser Ala Lys Asp
465                 470

<210> SEQ ID NO 50
<211> LENGTH: 416
<212> TYPE: PRT
<213> ORGANISM: Aspergillus niger

<400> SEQUENCE: 50

Met Asn Val Glu Thr Ser Leu Pro Gly Ser Gly Ser Asp Leu Glu
1               5                   10                  15

Thr Phe His His Glu Thr Lys Lys His Ala Asn His Asp Ser Gly Ile
                20                  25                  30

Ser Val Asn His Glu Ala Glu Ile Gly Val Asn His Thr Phe Glu Lys
            35                  40                  45

Pro Gly Pro Val Gly Ile Arg Glu Arg Leu Arg His Phe Thr Trp Ala
        50                  55                  60

Trp Tyr Thr Leu Thr Met Ser Cys Gly Gly Leu Ala Leu Leu Ile Val
65                  70                  75                  80

Asn Gln Pro His Asp Phe Lys Gly Leu Lys Asp Ile Ala Arg Val Val
                85                  90                  95

Tyr Cys Leu Asn Leu Ala Phe Phe Val Ile Val Thr Ser Leu Met Ala
            100                 105                 110

Ile Arg Phe Ile Leu His Lys Asn Met Trp Glu Ser Leu Gly His Asp
        115                 120                 125

Arg Glu Gly Leu Phe Phe Pro Thr Phe Trp Leu Ser Ile Ala Thr Met
    130                 135                 140

Ile Thr Gly Leu Tyr Lys Cys Phe Gly Asp Asp Ala Asn Glu Lys Phe
145                 150                 155                 160

Thr Lys Cys Leu Gln Val Leu Phe Trp Ile Tyr Cys Gly Cys Thr Met
                165                 170                 175

Ile Thr Ala Val Gly Gln Tyr Ser Phe Val Phe Ala Thr His Lys Tyr
            180                 185                 190

Glu Leu His Thr Met Met Pro Ser Trp Ile Leu Pro Ala Phe Pro Val
        195                 200                 205

Met Leu Ser Gly Thr Ile Ala Ser Val Ile Gly Ser Gly Gln Pro Ala
    210                 215                 220

Ser Asp Gly Ile Pro Ile Ile Ala Gly Ile Thr Phe Gln Gly Leu
225                 230                 235                 240

Gly Phe Ser Ile Ser Phe Met Met Tyr Ala His Tyr Ile Gly Arg Leu
                245                 250                 255

Met Glu Val Gly Leu Pro Ser Pro Glu His Arg Pro Gly Met Phe Ile
            260                 265                 270

Cys Val Gly Pro Pro Ala Phe Thr Ala Leu Ala Leu Val Gly Met Ala
        275                 280                 285

Lys Ala Leu Pro Asp Asp Phe Gln Ile Val Gly Asp Pro His Ala Val
    290                 295                 300

Ile Asp Gly Arg Val Met Leu Phe Leu Ala Val Ser Ala Ala Ile Phe
305                 310                 315                 320

Leu Trp Ala Leu Ser Phe Trp Phe Phe Cys Ile Ala Val Val Ala Val
                325                 330                 335

Val Arg Ser Pro Pro Lys Gly Phe His Leu Asn Trp Phe Ala Met Val
            340                 345                 350

Phe Pro Asn Thr Gly Phe Thr Leu Ala Thr Ile Thr Leu Ala Asn Met
        355                 360                 365

Phe Glu Ser Pro Gly Val Lys Gly Val Ala Thr Ala Met Ser Leu Cys
        370                 375                 380

Val Ile Ile Met Phe Ile Phe Val Leu Val Ser Ala Ile Arg Ala Val
385                 390                 395                 400

Ile Arg Lys Asp Ile Met Trp Pro Gly Gln Asp Glu Asp Val Ser Glu
                405                 410                 415

<210> SEQ ID NO 51
<211> LENGTH: 542
<212> TYPE: PRT
<213> ORGANISM: Kluyveromyces lactis

<400> SEQUENCE: 51

Met Val Ser Val Lys Ala Ser Ala Ala Glu Lys Lys Glu Phe Leu Gln
1               5                   10                  15

Ser Gln Ile Asp Glu Ile Glu Lys Trp Trp Ser Glu Pro Arg Trp Lys
            20                  25                  30

Asp Thr Lys Arg Ile Tyr Ser Ala Tyr Glu Ile Ala Lys Arg Arg Gly
        35                  40                  45

Ser Val Lys Pro Asn Thr Phe Pro Ser Thr Val Met Ser Gln Lys Leu
50                  55                  60

Phe Lys Ile Leu Gly Glu His Ala Lys Asn Gly Thr Val Ser Lys Thr
65                  70                  75                  80

Phe Gly Ala Leu Asp Pro Val Gln Val Thr Gln Met Ser Lys Tyr Leu
                85                  90                  95

Asp Thr Ile Tyr Val Ser Gly Trp Gln Cys Ser Ser Thr Ala Ser Thr
            100                 105                 110

Ser Asn Glu Pro Gly Pro Asp Leu Ala Asp Tyr Pro Met Asp Thr Val
        115                 120                 125

Pro Asn Lys Val Glu His Leu Phe Lys Ala Gln Gln Phe His Asp Arg
130                 135                 140

Lys Gln Trp Glu Arg Ile Cys Asp Gly Thr Ile Glu Glu Ser Glu Ile
145                 150                 155                 160

Ile Asp Tyr Leu Thr Pro Ile Val Ala Asp Gly Asp Ala Gly His Gly
                165                 170                 175

Gly Leu Thr Ala Val Phe Lys Leu Thr Lys Met Phe Ile Glu Arg Gly
            180                 185                 190

Ala Ala Gly Ile His Ile Glu Asp Gln Thr Ser Thr Asn Lys Lys Cys
        195                 200                 205

Gly His Met Ala Gly Arg Cys Val Ile Pro Val Gln Glu His Ile Asn
210                 215                 220

Arg Leu Ile Thr Cys Arg Met Ala Ala Asp Val Leu Gly Ser Asp Leu
225                 230                 235                 240

Ile Leu Val Ala Arg Thr Asp Ser Glu Ala Ala Thr Leu Leu Ser Ser
                245                 250                 255

Thr Ala Asp Ser Arg Asp His Tyr Phe Ile Leu Gly Ala Ser Asn Pro
            260                 265                 270

Ala Val Lys Gly Lys Pro Leu Asn Asp Leu Leu Asn Lys Ala Ile Leu
        275                 280                 285

Asp Gly Ala Thr Ile Asp Asp Leu Gln Thr Ile Glu Lys Glu Trp Leu
290                 295                 300

Ala Lys Ala Asp Val Lys Leu Phe His Glu Val Phe Ala Asp Ala Ala
305                 310                 315                 320

Lys Ala Ala Gly Lys Asp Gln Ser Val Ile Asp Gln Phe Asn Ser Lys

```
                325                 330                 335
Val Asn Pro Leu Ser Glu Thr Ser Ile Tyr Glu Met Gln Ala Leu Ala
                340                 345                 350

Lys Glu Leu Leu Gly Thr Glu Leu Phe Phe Asp Trp Asp Leu Pro Arg
                355                 360                 365

Gly Arg Glu Gly Leu Tyr Arg Tyr Gln Gly Gly Thr Gln Cys Ser Val
            370                 375                 380

Met Arg Ala Arg Ala Phe Ala Pro Tyr Ala Asp Leu Cys Trp Met Glu
385                 390                 395                 400

Ser Asn Tyr Pro Asp Tyr Glu Gln Ala Lys Glu Phe Ala Glu Gly Val
                405                 410                 415

Thr Ala Lys Phe Pro Gly Lys Trp Met Ala Tyr Asn Leu Ser Pro Ser
                420                 425                 430

Phe Asn Trp Thr Lys Ala Met Ser Val Asp Glu Gln Glu Thr Phe Ile
                435                 440                 445

Gln Arg Leu Gly Asp Leu Gly Tyr Ile Trp Gln Phe Ile Thr Leu Ala
            450                 455                 460

Gly Leu His Thr Ser Gly Leu Ala Ile Glu Gln Phe Ser Lys Asn Phe
465                 470                 475                 480

Ala Lys Leu Gly Met Lys Ala Tyr Ala Gln Asp Ile Gln Lys Lys Glu
                485                 490                 495

Leu Asp Asn Gly Ile Asp Met Val Lys His Gln Lys Trp Ser Gly Ala
                500                 505                 510

Glu Tyr Ile Asp Gly Leu Leu Arg Leu Ala Gln Gly Gly Leu Ala Ala
            515                 520                 525

Thr Ala Ala Met Gly Gln Gly Val Thr Glu Asp Gln Phe Lys
                530                 535                 540

<210> SEQ ID NO 52
<211> LENGTH: 551
<212> TYPE: PRT
<213> ORGANISM: Artificial Sequence
<220> FEATURE:
<223> OTHER INFORMATION: amino acid sequence of Saccharomyces cerevisiae
      peroxisomal malate synthase (Mls1) amino acid sequence, lacking
      the 3 C-terminal peroxisomal targeting sequence

<400> SEQUENCE: 52

Met Val Lys Val Ser Leu Asp Asn Val Lys Leu Leu Val Asp Val Asp
1               5                   10                  15

Lys Glu Pro Phe Phe Lys Pro Ser Ser Thr Val Gly Asp Ile Leu
                20                  25                  30

Thr Lys Asp Ala Leu Glu Phe Ile Val Leu Leu His Arg Thr Phe Asn
                35                  40                  45

Asn Lys Arg Lys Gln Leu Leu Glu Asn Arg Gln Val Val Gln Lys Lys
            50                  55                  60

Leu Asp Ser Gly Ser Tyr His Leu Asp Phe Leu Pro Glu Thr Ala Asn
65                  70                  75                  80

Ile Arg Asn Asp Pro Thr Trp Gln Gly Pro Ile Leu Ala Pro Gly Leu
                85                  90                  95

Ile Asn Arg Ser Thr Glu Ile Thr Gly Pro Pro Leu Arg Asn Met Leu
                100                 105                 110

Ile Asn Ala Leu Asn Ala Pro Val Asn Thr Tyr Met Thr Asp Phe Glu
            115                 120                 125

Asp Ser Ala Ser Pro Thr Trp Asn Asn Met Val Tyr Gly Gln Val Asn
            130                 135                 140
```

```
Leu Tyr Asp Ala Ile Arg Asn Gln Ile Asp Phe Asp Thr Pro Arg Lys
145                 150                 155                 160

Ser Tyr Lys Leu Asn Gly Asn Val Ala Asn Leu Pro Thr Ile Ile Val
            165                 170                 175

Arg Pro Arg Gly Trp His Met Val Glu Lys His Leu Tyr Val Asp Asp
            180                 185                 190

Glu Pro Ile Ser Ala Ser Ile Phe Asp Phe Gly Leu Tyr Phe Tyr His
            195                 200                 205

Asn Ala Lys Glu Leu Ile Lys Leu Gly Lys Gly Pro Tyr Phe Tyr Leu
            210                 215                 220

Pro Lys Met Glu His His Leu Glu Ala Lys Leu Trp Asn Asp Val Phe
225                 230                 235                 240

Cys Val Ala Gln Asp Tyr Ile Gly Ile Pro Arg Gly Thr Ile Arg Ala
            245                 250                 255

Thr Val Leu Ile Glu Thr Leu Pro Ala Ala Phe Gln Met Glu Glu Ile
            260                 265                 270

Ile Tyr Gln Leu Arg Gln His Ser Ser Gly Leu Asn Cys Gly Arg Trp
            275                 280                 285

Asp Tyr Ile Phe Ser Thr Ile Lys Arg Leu Arg Asn Asp Pro Asn His
            290                 295                 300

Ile Leu Pro Asn Arg Asn Gln Val Thr Met Thr Ser Pro Phe Met Asp
305                 310                 315                 320

Ala Tyr Val Lys Arg Leu Ile Asn Thr Cys His Arg Arg Gly Val His
            325                 330                 335

Ala Met Gly Gly Met Ala Ala Gln Ile Pro Ile Lys Asp Asp Pro Ala
            340                 345                 350

Ala Asn Glu Lys Ala Met Thr Lys Val Arg Asn Asp Lys Ile Arg Glu
            355                 360                 365

Leu Thr Asn Gly His Asp Gly Ser Trp Val Ala His Pro Ala Leu Ala
            370                 375                 380

Pro Ile Cys Asn Glu Val Phe Ile Asn Met Gly Thr Pro Asn Gln Ile
385                 390                 395                 400

Tyr Phe Ile Pro Glu Asn Val Val Thr Ala Ala Asn Leu Leu Glu Thr
            405                 410                 415

Lys Ile Pro Asn Gly Glu Ile Thr Thr Glu Gly Ile Val Gln Asn Leu
            420                 425                 430

Asp Ile Gly Leu Gln Tyr Met Glu Ala Trp Leu Arg Gly Ser Gly Cys
            435                 440                 445

Val Pro Ile Asn Asn Leu Met Glu Asp Ala Ala Thr Ala Glu Val Ser
            450                 455                 460

Arg Cys Gln Leu Tyr Gln Trp Val Lys His Gly Val Thr Leu Lys Asp
465                 470                 475                 480

Thr Gly Glu Lys Val Thr Pro Glu Leu Thr Glu Lys Ile Leu Lys Glu
            485                 490                 495

Gln Val Glu Arg Leu Ser Lys Ala Ser Pro Leu Gly Asp Lys Asn Lys
            500                 505                 510

Phe Ala Leu Ala Ala Lys Tyr Phe Leu Pro Glu Ile Arg Gly Glu Lys
            515                 520                 525

Phe Ser Glu Phe Leu Thr Thr Leu Leu Tyr Asp Glu Ile Val Ser Thr
            530                 535                 540

Lys Ala Thr Pro Thr Asp Leu
545                 550
```

<210> SEQ ID NO 53
<211> LENGTH: 343
<212> TYPE: PRT
<213> ORGANISM: Saccharomyces cerevisiae

<400> SEQUENCE: 53

Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
        35                  40                  45

Asn Thr Asn Ser Ser Cys Val Gly Tyr Asp Lys Asp Ser Ile Glu Asn
    50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
                85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
        115                 120                 125

Glu Thr Leu Lys Lys Met Gly Lys Phe Lys Pro Gly Asn Val Met Gly
    130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175

Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
        195                 200                 205

Tyr Glu His Phe Ile His Arg Val Gln Phe Gly Gly Asp Glu Ile Val
    210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
        275                 280                 285

Phe Ser Leu Pro Ile Val Leu Arg Asn Gly Ser Val Val Ser Ile Asp
    290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser Ser Lys Leu
            340

<210> SEQ ID NO 54
<211> LENGTH: 25
<212> TYPE: DNA
<213> ORGANISM: Artificial Sequence

```
<220> FEATURE:
<223> OTHER INFORMATION: nucleotide sequence of the primer used to
      generate fragment 116 (Figure 6)

<400> SEQUENCE: 54
cggcattatt gtgtatggct caata                                              25

<210> SEQ ID NO 55
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 116 (Figure 6)

<400> SEQUENCE: 55
gaacttcgac ctgttgcaat acttcgggtt cggcacaaac gtgtacggat agggtttcaa        60
agatccatac ttctc                                                         75

<210> SEQ ID NO 56
<211> LENGTH: 79
<212> TYPE: DNA
<213> ORGANISM: Artificial Sequence
<220> FEATURE:
<223> OTHER INFORMATION: nucleotide sequence of the primer used to
      generate fragment 117 (Figure 6)

<400> SEQUENCE: 56
atccgtacac gtttgtgccg aacccgaagt attgcaacag gtcgaagttc tcgtacgctg        60
caggtcgacg aattctacc                                                     79

<210> SEQ ID NO 57
<211> LENGTH: 74
<212> TYPE: DNA
<213> ORGANISM: Artificial Sequence
<220> FEATURE:
<223> OTHER INFORMATION: nucleotide sequence of the primer used to
      generate fragment 117 (Figure 6)

<400> SEQUENCE: 57
aatcgcaact cggatttggg aggcaaggtc ggaacgcgaa ctttggcttt aggccactag        60
tggatctgat atcg                                                          74

<210> SEQ ID NO 58
<211> LENGTH: 90
<212> TYPE: DNA
<213> ORGANISM: Artificial Sequence
<220> FEATURE:
<223> OTHER INFORMATION: nucleotide sequence of the primer used to
      generate fragment 119 (Figure 6)

<400> SEQUENCE: 58
agaaagcctg tatgcgaagc cacaatcctt tccaacagac catactaagt attttatttt        60
acttttttta gaatgacctg ttcccgacac                                         90

<210> SEQ ID NO 59
<211> LENGTH: 24
<212> TYPE: DNA
<213> ORGANISM: Artificial Sequence
<220> FEATURE:
<223> OTHER INFORMATION: nucleotide sequence of the primer used to
      generate fragment 119 (Figure 6)

<400> SEQUENCE: 59
```

```
cacaagctta ttcttccaaa aatc                                         24
```

<210> SEQ ID NO 60
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 118 (Figure 6)

<400> SEQUENCE: 60

```
aaagccaaag ttcgcgttcc                                              20
```

<210> SEQ ID NO 61
<211> LENGTH: 24
<212> TYPE: DNA
<213> ORGANISM: Artificial Sequence
<220> FEATURE:
<223> OTHER INFORMATION: nucleotide sequence of the primer used to
      generate fragment 118 (Figure 6)

<400> SEQUENCE: 61

```
acttagtatg gtctgttgga aagg                                         24
```

<210> SEQ ID NO 62
<211> LENGTH: 4429
<212> TYPE: DNA
<213> ORGANISM: Artificial Sequence
<220> FEATURE:
<223> OTHER INFORMATION: nucleotide sequence of fragment 118 (Figure 6)
      which includes coding sequence for fumarate reductase from
      Trypanosoma brucei (FRDg) codon pair optimized for expression in
      S. cerevisiae

<400> SEQUENCE: 62

```
aaagccaaag ttcgcgttcc gaccttgcct cccaaatccg agttgcgatt gtgcttagtc    60
aaaaaattag ccttttaatt ctgctgtaac ccgtacatgc ccaaaatagg gggcgggtta   120
cacagaatat ataacatcgt aggtgtctgg gtgaacagtt tattcctggc atccactaaa   180
tataatggag cccgcttttt aagctggcat ccagaaaaaa aaagaatccc agcaccaaaa   240
tattgttttc ttcaccaacc atcagttcat aggtccattc tcttagcgca actacagaga   300 acagggcac aaacaggcaa aaacgggca caacctcaat ggagtgatgc aacctgcctg    360
gagtaaatga tgacacaagg caattgaccc acgcatgtat ctatctcatt ttcttacacc   420
ttctattacc ttctgctctc tctgatttgg aaaagctga aaaaaaggt tgaaaccagt     480 tccctgaaat tattccccta cttgactaat aagtatataa agacggtagg tattgattgt   540
aattctgtaa atctatttct taaacttctt aaattctact tttatagtta gtcttttttt   600
tagttttaaa acaccaagaa cttagtttcg aataaacaca cataaacaaa caaatggtt    660 gatggtagat cttctgcttc cattgttgcc gttgacccag aaagagctgc cagagaaaga   720
gatgctgctg ccagagcttt gttgcaagac tctccattgc acaccaccat gcaatacgct   780
acctctggtt tggaattgac tgttccatac gctttgaagg ttgttgcttc tgctgacact   840
ttcgacagag ccaaggaagt tgctgatgaa gtcttgagat gtgcctggca attggctgac   900
accgttttga actctttcaa cccaaactct gaagtctctt tagtcggtag attaccagtc   960
ggtcaaaagc atcaaatgtc tgctccattg aaacgtgtca tggcttgttg tcaaagagtc  1020
tacaactcct ctgctggttg tttcgaccca tccactgctc cagttgccaa ggctttgaga  1080
gaaattgctt tgggtaagga agaaacaat gcttgtttgg aagctttgac tcaagcttgt  1140
```

```
accttgccaa actctttcgt cattgatttc gaagctggta ctatctccag aaagcacgaa    1200
cacgcttctt tggatttggg tggtgtttcc aagggttaca tcgtcgatta cgtcattgac    1260
aacatcaatg ctgctggttt ccaaaacgtt ttctttgact ggggtggtga ctgtcgtgcc    1320
tccggtatga acgccagaaa cactccatgg gttgtcggta tcactagacc tccttccttg    1380
gacatgttgc aaaccctcc aaaggaagct tcttacatct ccgtcatctc tttggacaat    1440
gaagctttgg ctacctctgg tgattacgaa aacttgatct acactgctga cgataaacca    1500
ttgacctgta cctacgattg gaaaggtaag gaattgatga agccatctca atccaatatc    1560
gctcaagttt ccgtcaagtg ttactctgcc atgtacgctg acgctttggc taccgcttgt    1620
ttcatcaagc gtgacccagc caaggtcaga caattgttgg atggttggag atacgttaga    1680
gacaccgtca gagattaccg tgtctacgtc agagaaaacg aaagagttgc caagatgttc    1740
gaaattgcca ctgaagatgc tgaaatgaga agagaagaa tttccaacac tttaccagct    1800
cgtgtcattg ttgttggtgg tggtttggct ggtttgtccg ctgccattga agctgctggt    1860
tgtggtgctc aagttgtttt gatggaaaag gaagccaagt ggggtggtaa ctctgccaag    1920
gctacctctg gtatcaacgg ttggggtact agagcccaag ctaaggcttc cattgtcgat    1980
ggtggtaagt acttcgaaag agatacctac aagtctggta tcggtggtaa caccgatcca    2040
gctttggtta agactttgtc catgaaatct gctgacgcta tcggttggtt gacttctcta    2100
ggtgttccat tgactgtttt gtcccaatta ggtggtcact ccagaaagag aactcacaga    2160
gccccagaca agaaggatgg tactccattg ccaattggtt tcaccatcat gaaaactta    2220 gaagatcatg ttagaggtaa cttgtccggt agaatcacca tcatgaaaa ctgttccgtt    2280 acctctttgt tgtctgaaac caaggaaaga ccagacggta ctaagcaaat cagagttacc    2340
ggtgtcgaat tcactcaagc tggttctggt aagaccacca ttttggctga tgctgttatc    2400
ttggccaccg gtggtttctc caacgacaag actgctgatt cttgttgag agaacatgcc    2460 ccacacttgg ttaacttccc aaccaccaac ggtccatggg ctactggtga tggtgtcaag    2520
ttggctcaaa gattaggtgc tcaattggtc gatatggaca aggttcaatt gcacccaact    2580
ggtttgatca acccaaagga cccagccaac ccaaccaaat tcttgggtcc agaagctcta    2640
agaggttctg gtggtgtttt gttgaacaaa caaggtaaga gatttgtcaa cgaattggat    2700
ttgagatctg ttgtttccaa ggccatcatg gaacaaggtg ctgaataccc aggttctggt    2760
ggttccatgt ttgcttactg tgtcttgaac gctgctgctc aaaaaattgtt tggtgtttcc    2820 tctcacgaat tctactggaa gaagatgggt ttgttcgtca aggctgacac catgagagac    2880
ttggctgctt tgattggttg tccagttgaa tccgttcaac aaactttaga agaatacgaa    2940
agattatcca tctctcaaag atcttgtcca attaccagaa atctgtttta cccatgtgtt    3000
ttgggtacta aaggtccata ctatgtcgcc tttgtcactc catctatcca ctacaccatg    3060
ggtggttgtt tgatttctcc atctgctgaa atccaaatga gaacacttc ttccagagcc    3120 ccattgtccc actccaaccc aatcttgggt ttattcggtg ctggtgaagt caccggtggt    3180
gtccacggtg gtaacagatt aggtggtaac tctttgttgg aatgtgttgt tttcggtaga    3240
attgccggtg acagagcttc taccattttg caaagaaagt cctctgcttt gtctttcaag    3300
gtctggacca ctgttgtttt gagagaagtc agagaaggtg tgtctacgg tgctggttcc    3360 cgtgtcttga gattcaactt accaggtgct ctacaaagat ctggtctatc cttgggtcaa    3420
ttcattgcca tcagaggtga ctgggacggt caacaattga ttggttacta ctctccaatc    3480
actttgccag acgatttggg tatgattgac atttttggcca gatctgacaa gggtactta    3540
```

```
cgtgaatgga tctctgcttt ggaaccaggt gacgctgtcg aaatgaaggc ttgtggtggt    3600
ttggtcatcg aaagaagatt atctgacaag cacttcgttt tcatgggtca cattatcaac    3660
aagctatgtt tgattgctgg tggtactggt gttgctccaa tgttgcaaat catcaaggcc    3720
gctttcatga agccattcat cgacactttg aatccgtcc acttgatcta cgctgctgaa     3780
gatgtcactg aattgactta cagagaagtt ttggaagaac gtcgtcgtga atccagaggt    3840
aaattcaaga aaactttcgt tttgaacaga cctcctccat tatggactga cggtgtcggt    3900
ttcatcgacc gtggtatctt gaccaaccac gttcaaccac catctgacaa cttattggtt    3960
gccatctgtg tccaccagt tatgcaaaga attgtcaagg ccactttaaa gactttaggt     4020
tacaacatga acttggtcag aaccgttgac gaaactgaac catctggaag ttaaaggaag    4080
tatctcggaa atattaattt aggccatgtc cttatgcacg tttctttga tacttacggg     4140 tacatgtaca caagtatatc tatatatata aattaatgaa aatcccctat ttatatatat    4200
gactttaacg agacagaaca gttttttatt ttttatccta tttgatgaat gatacagttt    4260
cttattcacg tgttataccc acaccaaatc caatagcaat accggccatc acaatcactg    4320
tttcggcagc ccctaagatc agacaaaaca tccggaacca ccttaaatca acgtccctca    4380
gaaagcctgt atgcgaagcc acaatccttt ccaacagacc atactaagt                4429
```

<210> SEQ ID NO 63
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 124 (Figure 7)

<400> SEQUENCE: 63

```
gaaaccttcg aatccagcca gcatgtcgac acccacaaga tgtagtgcac acaggtgatt     60
gtatgtgggc ttatg                                                      75
```

<210> SEQ ID NO 64
<211> LENGTH: 2032
<212> TYPE: DNA
<213> ORGANISM: Artificial Sequence
<220> FEATURE:
<223> OTHER INFORMATION: nucleotide sequence of fragment 121 (Figure 7)
      which includes coding sequence for S. cerevisiae MDH3 mutant
      MUT_014 codon pair optimized for expression in S. cerevisiae

<400> SEQUENCE: 64

```
aaataaccac aaacatcctt cccatatgct cggtcgtgct tgttgtacct gtgcttagtc     60
aaaaaattag cctttaatt ctgctgtaac ccgtacatgc ccaaaatagg gggcgggtta     120
cacagaatat ataacatcgt aggtgtctgg gtgaacagtt tattcctggc atccactaaa    180
tataatggag cccgcttttt aagctggcat ccagaaaaaa aaagaatccc agcaccaaaa    240
tattgttttc ttcaccaacc atcagttcat aggtccattc tcttagcgca actacagaga    300 acagggcac aaacaggcaa aaaacgggca caacctcaat ggagtgatgc aacctgcctg     360
gagtaaatga tgcacaagg caattgaccc acgcatgtat ctatctcatt ttcttacacc     420
ttctattacc ttctgctctc tctgatttgg aaaaagctga aaaaaaaggt tgaaaccagt    480
tccctgaaat tattccccta cttgactaat aagtatataa agacggtagg tattgattgt    540
aattctgtaa atctatttct taaacttctt aaattctact tttatagtta gtcttttttt    600
tagttttaaa acaccaagaa cttagtttcg aataaacaca cataaacaaa caaaatggtt   660
```

```
aaggttgcca tcttaggtgc ttctggtggt gtcggtcaac cattatctct attattgaaa    720
ttgtctccat acgtttctga attggctttg tacggtatct ctgctgctga aggtattggt    780
aaggatttgt cccacatcaa caccaactcc tcttgtgttg gttacgacaa ggattccatc    840
gaaaacactt tgtccaatgc tcaagttgtc ttgattccag ctggtgttcc aagaaagcca    900
ggtttgacca gagatgattt gttcaagatg aacgctggta tcgttaagtc tttggttact    960
gctgtcggta aatttgcccc aaacgctcgt atcttagtca tctccaaccc tgttaactct   1020
ttggttccaa ttgccgttga aactttgaag aagatgggta agttcaagcc aggtaacgtt   1080
atgggtgtca ccaacttgga tttggtcaga gctgaaactt tcttggttga ctacttgatg   1140
ttgaagaacc caaagatcgg tcaagaacaa gacaagacca ccatgcacag aaaggtcacc   1200
gtcatcggtg tcactctggt gaaaccatc attccaatca tcactgacaa atccttggtt   1260
ttccaattgg acaagcaata cgaacatttc atccacagag tccaattcgg tggtgacgaa   1320
attgtcaagg ccaagcaagg tgccggttct gctaccttgt ccatggcttt cgctggtgcc   1380
aaatttgctg aagaagtctt acgttctttc cacaacgaaa agccagaaac tgaatctttg   1440
tctgctttcg tctacttgcc aggtttgaag aacggtaaga aggctcaaca attagtcggt   1500
gacaactcca ttgaatactt ctctttgcca attgttttga gaaacggttc cgttgtttcc   1560
attgacactt ctgttttgga aaaattgtct ccaagagaag aacaattggt caacactgct   1620
gtcaaggaat tgagaaagaa cattgaaaag ggtaagtctt tcatcttgga cagttaaagt   1680
ctgaagaatg aatgatttga tgatttcttt ttccctccat ttttcttact gaatatatca   1740
atgatataga cttgtatagt ttattatttc aaattaagta gctatatata gtcaagataa   1800
cgtttgtttg acacgattac attattcgtc gacatctttt ttcagcctgt cgtggtagca   1860
atttgaggag tattattaat tgaataggtt cattttgcgc tcgcataaac agttttcgtc   1920
agggacagta tgttggaatg agtggtaatt aatggtgaca tgacatgtta tagcaatacc   1980
tcgaaacctt cgaatccagc cagcatgtcg acacccacaa gatgtagtgc ac           2032
```

<210> SEQ ID NO 65
<211> LENGTH: 2032
<212> TYPE: DNA
<213> ORGANISM: Artificial Sequence
<220> FEATURE:
<223> OTHER INFORMATION: nucleotide sequence of fragment 122 (Figure 7) which includes coding sequence for S. cerevisiae MDH3 mutant MUT_015 codon pair optimized for expression in S. cerevisiae

<400> SEQUENCE: 65

```
aaataaccac aaacatccct cccatatgct cggtcgtgct tgttgtacct gtgcttagtc     60
aaaaaattag cctttttaatt ctgctgtaac ccgtacatgc ccaaaatagg gggcgggtta    120
cacagaatat ataacatcgt aggtgtctgg gtgaacagtt tattcctggc atccactaaa    180
tataatggag cccgcttttt aagctggcat ccagaaaaaa aaagaatccc agcaccaaaa    240
tattgttttc ttcaccaacc atcagttcat aggtccattc tcttagcgca actacagaga    300 acagggcac aaacaggcaa aaaacgggca caacctcaat ggagtgatgc aacctgcctg     360
gagtaaatga tgacacaagg caattgaccc acgcatgtat ctatctcatt ttcttacacc    420
ttctattacc ttctgctctc tctgatttgg aaaaagctga aaaaaaaggt tgaaaccagt    480
tccctgaaat tattcccctaa cttgactaat aagtatataa agacggtagg tattgattgt   540
aattctgtaa atctatttct taaacttctt aaattctact tttatagtta gtctttttt     600
```

```
tagttttaaa acaccaagaa cttagtttcg aataaacaca cataaacaaa caaaatggtt      660
aaggttgcca tcttaggtgc ttctggtggt gtcggtcaac cattatctct attattgaaa      720
ttgtctccat acgtttctga attggctttg tacggttcca gagctgctga aggtattggt      780
aaggatttgt cccacatcaa caccaactcc tcttgtgttg gttacgacaa ggattccatc      840
gaaaacactt tgtccaatgc tcaagttgtc ttgattccag ctggtgttcc aagaaagcca      900
ggtttgacca gagatgattt gttcaagatg aacgctggta tcgttaagtc tttggttact      960
gctgtcggta aatttgcccc aaacgctcgt atcttagtca tctccaaccc tgttaactct     1020
ttggttccaa ttgccgttga aacttttgaag aagatgggaa agttcaagcc aggtaacgtt     1080
atgggtgtca ccaacttgga tttggtcaga gctgaaactt tcttggttga ctacttgatg     1140
ttgaagaacc caaagatcgg tcaagaacaa gacaagacca ccatgcacag aaaggtcacc     1200
gtcatcggtg gtcactctgg tgaaaccatc attccaatca tcactgacaa atccttggtt     1260
ttccaattgg acaagcaata cgaacatttc atccacagag tccaattcgg tggtgacgaa     1320
attgtcaagg ccagcaagg tgccggttct gctaccttgt ccatggcttt cgctggtgcc     1380
aaatttgctg aagaagtctt acgttctttc cacaacgaaa agccagaaac tgaatctttg     1440
tctgctttcg tctacttgcc aggtttgaag aacggtaaga aggctcaaca attagtcggt     1500
gacaactcca ttgaatactt ctctttgcca attgttttga aaacggttc cgttgtttcc     1560 attgacactt ctgttttgga aaaattgtct ccaagagaaa acaattggt caacactgct     1620 gtcaaggaat tgagaaagaa cattgaaaag ggtaagtctt tcatcttgga cagttaaagt     1680
ctgaagaatg aatgatttga tgatttcttt ttccctccat ttttcttact gaatatatca     1740
atgatataga cttgtatagt ttattatttc aaattaagta gctatatata gtcaagataa     1800
cgtttgtttg acacgattac attattcgtc gacatctttt ttcagcctgt cgtggtagca     1860
atttgaggag tattattaat tgaataggtt cattttgcgc tcgcataaac agttttcgtc     1920
agggacagta tgttggaatg agtggtaatt aatggtgaca tgacatgtta tagcaatacc     1980
tcgaaacctt cgaatccagc cagcatgtcg acacccacaa gatgtagtgc ac             2032
```

<210> SEQ ID NO 66
<211> LENGTH: 2032
<212> TYPE: DNA
<213> ORGANISM: Artificial Sequence
<220> FEATURE:
<223> OTHER INFORMATION: nucleotide sequence of fragment 123 (Figure 7)
      which includes coding sequence for S. cerevisiae MDH3 mutant
      MUT_034 codon pair optimized for expression in S. cerevisiae

<400> SEQUENCE: 66

```
aaataaccac aaacatcctt cccatatgct cggtcgtgct tgttgtacct gtgcttagtc       60
aaaaaattag cctttaatt ctgctgtaac ccgtacatgc ccaaaatagg gggcgggtta      120
cacagaatat ataacatcgt aggtgtctgg gtgaacagtt tattcctggc atccactaaa      180
tataatggag cccgcttttt aagctggcat ccagaaaaaa aagaatccc agcaccaaaa      240 tattgttttc ttcaccaacc atcagttcat aggtccattc tcttagcgca actacagaga      300 acagggcac aaacaggcaa aaacgggca caacctcaat ggagtgatgc aacctgcctg      360
gagtaaatga tgcacaagg caattgaccc acgcatgtat ctatctcatt ttcttacacc      420
ttctattacc ttctgctctc tctgatttgg aaaagctga aaaaaaaggt tgaaccagt      480 tccctgaaat tattccccta cttgactaat aagtatataa agacggtagg tattgattgt      540
aattctgtaa atctatttct taaacttctt aaattctact tttatagtta gtcttttttt     600
```

-continued

```
tagttttaaa acaccaagaa cttagtttcg aataaacaca cataaacaaa caaaatggtt    660
aaggttgcca tcttaggtgc ttctggtggt gtcggtcaac cattatctct attattgaaa    720
ttgtctccat acgtttctga attggctttg tactcttctt ccaacgtcaa gggtattggt    780
aaggatttgt cccacatcaa caccaactcc tcttgtgttg gttacgacaa ggattccatc    840
gaaaacactt tgtccaatgc tcaagttgtc ttgattccag ctggtgttcc aagaaagcca    900
ggtttgacca gagatgattt gttcaagatg aacgctggta tcgttaagtc tttggttact    960
gctgtcggta aatttgcccc aaacgctcgt atcttagtca tctccaaccc tgttaactct   1020
ttggttccaa ttgccgttga aactttgaag aagatgggta agttcaagcc aggtaacgtt   1080
atgggtgtca ccaacttgga tttggtcaga gctgaaactt tcttggttga ctacttgatg   1140
ttgaagaacc caaagatcgg tcaagaacaa gacaagacca ccatgcacag aaaggtcacc   1200
gtcatcggtg gtcactctgg tgaaaccatc attccaatca tcactgacaa atccttggtt   1260
ttccaattgg acaagcaata cgaacatttc atccacagag tccaattcgg tggtgacgaa   1320
attgtcaagg ccaagcaagg tgccggttct gctaccttgt ccatggcttt cgctggtgcc   1380
aaatttgctg aagaagtctt acgttctttc cacaacgaaa agccagaaac tgaatctttg   1440
tctgctttcg tctacttgcc aggtttgaag aacggtaaga aggctcaaca attagtcggt   1500
gacaactcca ttgaatactt ctcttttgcca attgttttga aaacggttc cgttgtttcc   1560
attgacactt ctgttttgga aaaattgtct ccaagagaag aacaattggt caacactgct   1620
gtcaaggaat tgagaaagaa cattgaaaag ggtaagtctt tcatcttgga cagttaaagt   1680
ctgaagaatg aatgatttga tgatttcttt ttccctccat ttttcttact gaatatatca   1740
atgatataga cttgtatagt ttattatttc aaattaagta gctatatata gtcaagataa   1800
cgtttgtttg acacgattac attattcgtc gacatctttt ttcagcctgt cgtggtagca   1860
atttgaggag tattattaat tgaataggtt catttttgcgc tcgcataaac agttttcgtc   1920
agggacagta tgttggaatg agtggtaatt aatggtgaca tgacatgtta tagcaatacc   1980
tcgaaacctt cgaatccagc cagcatgtcg acacccacaa gatgtagtgc ac           2032
```

<210> SEQ ID NO 67
<211> LENGTH: 499
<212> TYPE: PRT
<213> ORGANISM: Arabidopsis thaliana

<400> SEQUENCE: 67

```
Met Ala Ala Leu Thr Met Gln Phe Glu Gly Glu Lys Lys Asn Val Ser
1               5                  10                  15

Glu Val Ala Asp Val Thr Leu Lys Gln Glu Asp Glu Gln Gln Glu Arg
            20                  25                  30

Arg Ser Tyr Ser Thr Pro Phe Arg Glu Glu Arg Asp Thr Phe Gly Pro
        35                  40                  45

Ile Gln Val Pro Ser Asp Lys Leu Trp Gly Ala Gln Thr Gln Arg Ser
    50                  55                  60

Leu Gln Asn Phe Glu Ile Gly Gly Asp Arg Glu Arg Met Pro Glu Pro
65                  70                  75                  80

Ile Val Arg Ala Phe Gly Val Leu Lys Lys Cys Ala Ala Lys Val Asn
                85                  90                  95

Met Glu Tyr Gly Leu Asp Pro Met Ile Gly Glu Ala Ile Met Glu Ala
            100                 105                 110

Ala Gln Glu Val Ala Glu Gly Lys Leu Asn Asp His Phe Pro Leu Val
```

-continued

```
            115                 120                 125
Val Trp Gln Thr Gly Ser Gly Thr Gln Ser Asn Met Asn Ala Asn Glu
        130                 135                 140

Val Ile Ala Asn Arg Ala Ala Glu Ile Leu Gly His Lys Arg Gly Glu
145                 150                 155                 160

Lys Ile Val His Pro Asn Asp His Val Asn Arg Ser Gln Ser Ser Asn
                165                 170                 175

Asp Thr Phe Pro Thr Val Met His Ile Ala Ala Thr Glu Ile Thr
                180                 185                 190

Ser Arg Leu Ile Pro Ser Leu Lys Asn Leu His Ser Ser Leu Glu Ser
        195                 200                 205

Lys Ser Phe Glu Phe Lys Asp Ile Val Lys Ile Gly Arg Thr His Thr
        210                 215                 220

Gln Asp Ala Thr Pro Leu Thr Leu Gly Gln Glu Phe Gly Gly Tyr Ala
225                 230                 235                 240

Thr Gln Val Glu Tyr Gly Leu Asn Arg Val Ala Cys Thr Leu Pro Arg
                245                 250                 255

Ile Tyr Gln Leu Ala Gln Gly Gly Thr Ala Val Gly Thr Gly Leu Asn
                260                 265                 270

Thr Lys Lys Gly Phe Asp Val Lys Ile Ala Ala Ala Val Ala Glu Glu
        275                 280                 285

Thr Asn Leu Pro Phe Val Thr Ala Glu Asn Lys Phe Glu Ala Leu Ala
        290                 295                 300

Ala His Asp Ala Cys Val Glu Thr Ser Gly Ser Leu Asn Thr Ile Ala
305                 310                 315                 320

Thr Ser Leu Met Lys Ile Ala Asn Asp Ile Arg Phe Leu Gly Ser Gly
                325                 330                 335

Pro Arg Cys Gly Leu Gly Glu Leu Ser Leu Pro Glu Asn Glu Pro Gly
                340                 345                 350

Ser Ser Ile Met Pro Gly Lys Val Asn Pro Thr Gln Cys Glu Ala Leu
                355                 360                 365

Thr Met Val Cys Ala Gln Val Met Gly Asn His Val Ala Val Thr Ile
        370                 375                 380

Gly Gly Ser Asn Gly His Phe Glu Leu Asn Val Phe Lys Pro Val Ile
385                 390                 395                 400

Ala Ser Ala Leu Leu His Ser Ile Arg Leu Ile Ala Asp Ala Ser Ala
                405                 410                 415

Ser Phe Glu Lys Asn Cys Val Arg Gly Ile Glu Ala Asn Arg Glu Arg
                420                 425                 430

Ile Ser Lys Leu Leu His Glu Ser Leu Met Leu Val Thr Ser Leu Asn
        435                 440                 445

Pro Lys Ile Gly Tyr Asp Asn Ala Ala Ala Val Ala Lys Arg Ala His
        450                 455                 460

Lys Glu Gly Cys Thr Leu Lys His Ala Ala Met Lys Leu Gly Val Leu
465                 470                 475                 480

Thr Ser Glu Glu Phe Asp Thr Leu Val Val Pro Glu Lys Met Ile Gly
                485                 490                 495

Pro Ser Asp
```

MALATE DEHYDROGENASES

CROSS-REFERENCE TO RELATED APPLICATIONS

This application is a National Stage entry of International Application No. PCT/EP2017/067318, filed 11 Jul. 2017, which claims priority to European Patent Application No. 16179315.3, filed 13 Jul. 2016.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-497000_ST25.txt" created on 8 Jan. 2019, and 143,312 bytes in size) is submitted concurrently with the instant application, and the entire contents of the Sequence Listing are incorporated herein by reference.

FIELD OF THE INVENTION

The present invention relates to a recombinant host cell capable of producing a dicarboxylic acid, and a method for producing a dicarboxylic acid using said recombinant host cell.

BACKGROUND OF THE INVENTION

The 4-carbon dicarboxylic acids malic acid, fumaric acid and succinic acid are potential precursors for numerous chemicals. For example, succinic acid can be converted into 1,4-butanediol (BDO), tetrahydrofuran, and gamma-butyrolactone. Another product derived from succinic acid is a polyester polymer which is made by linking succinic acid and BDO.

Succinic acid for industrial use is predominantly petrochemically produced from butane through catalytic hydrogenation of maleic acid or maleic anhydride. These processes are considered harmful for the environment and costly. The fermentative production of succinic acid is considered an attractive alternative process for the production of succinic acid, wherein renewable feedstock as a carbon source may be used.

Several studies have been carried out on the fermentative production of C4-dicarboxylic acid in (recombinant) yeast. EP2495304, for example, discloses a recombinant yeast suitable for succinic acid production, genetically modified with genes encoding a pyruvate carboxylase, a phosphoenolpyruvate carboxykinase, a malate dehydrogenase, a fumarase, a fumarate reductase and a succinate transporter.

Despite the improvements that have been made in the fermentative production of dicarboxylic acid in host cells, such as yeast, there nevertheless remains a need for further improved host cells for the fermentative production of dicarboxylic acids.

SUMMARY OF THE INVENTION

The present invention relates to a recombinant host cell which is capable of producing a dicarboxylic acid and which comprises a mutant polypeptide having malate dehydrogenase (MDH) activity. Surprisingly, it was found that the host cell according to the present invention produces an increased amount of a dicarboxylic acid as compared to the amount of dicarboxylic acid produced by a host cell comprising a reference MDH polypeptide, the reference MDH polypeptide being typically a NAD(H)-dependent malate dehydrogenase (EC 1.1.1.37).

According to the present invention, there is thus provided a recombinant host cell which is capable of producing a dicarboxylic acid and which comprises a nucleic acid sequence encoding a mutant polypeptide having malate dehydrogenase activity, wherein the mutant polypeptide comprises an amino acid sequence which, when aligned with the malate dehydrogenase comprising the sequence set out in SEQ ID NO: 39, comprises one mutation (e.g. one substitution) of an amino acid residue corresponding to amino acid 34 in SEQ ID NO: 39. Said mutant polypeptide having malate dehydrogenase activity may further comprise one or more additional mutations (e.g. substitutions). In particular, the mutant polypeptide having malate dehydrogenase activity may further comprise one or more additional mutations (e.g. substitutions) corresponding to any of amino acids 35, 36, 37, 38, 39 and/or 40 in SEQ ID NO: 39.

According to the present invention, there is also provided a recombinant host cell which is capable of producing a dicarboxylic acid and which comprises a nucleic acid sequence encoding a mutant polypeptide having malate dehydrogenase activity, wherein the mutant polypeptide has an increase in the NADP(H)- relative to NAD(H)-dependent activity as compared to that of a reference MDH polypeptide, the reference MDH polypeptide being typically a NAD(H)-dependent malate dehydrogenase (EC 1.1.1.37). In said embodiment, said mutant polypeptide may be a mutant polypeptide comprising an amino acid sequence which, when aligned with the malate dehydrogenase comprising the sequence set out in SEQ ID NO: 39, comprises one mutation (e.g. one substitution) of an amino acid residue corresponding to amino acid 34 in SEQ ID NO: 39

The invention also provides:
- a recombinant host cell according to the present invention, wherein the nucleic sequence encoding the mutant polypeptide having malate dehydrogenase activity is expressed in the cytosol and the mutant polypeptide having malate dehydrogenase activity is active in the cytosol.
- a recombinant host cell according to the present invention, wherein the recombinant host cell has an active reductive tricarboxylic acid (TCA) pathway from phosphoenol or pyruvate to succinate.
- a method for the production of a dicarboxylic acid, wherein the method comprises fermenting the recombinant host cell of the present invention under conditions suitable for production of the dicarboxylic acid. The dicarboxylic acid may be succinic acid, malic acid and/or fumaric acid. The method may further comprise recovering the dicarboxylic acid from the fermentation medium.

BRIEF DESCRIPTION OF THE DRAWINGS

FIG. 5B: NADH-specific malate dehydrogenase (MDH) activity of MDH mutants expressed in strain SUC-1112 (see Table 1 for specific mutations). Shown is activity, depicted as Δ A340/min/mg total protein. The value is negative as MDH-dependent NADH oxidation results in a decrease in absorbance at 340 nm. A more negative value indicates more activity. The activity was measured as described in Example 5.

FIG. 5C: NADPH-specific malate dehydrogenase (MDH) activity of MDH mutants expressed in strain SUC-1112 (see Table 1 for specific mutations). Shown is activity, depicted as Δ A340/min/mg total protein. The value is negative as MDH-dependent NADPH oxidation results in a decrease in absorbance at 340 nm. A more negative value indicates more activity. The activity was measured as described in Example 5.

DESCRIPTION OF THE SEQUENCE LISTING

Figure 1:
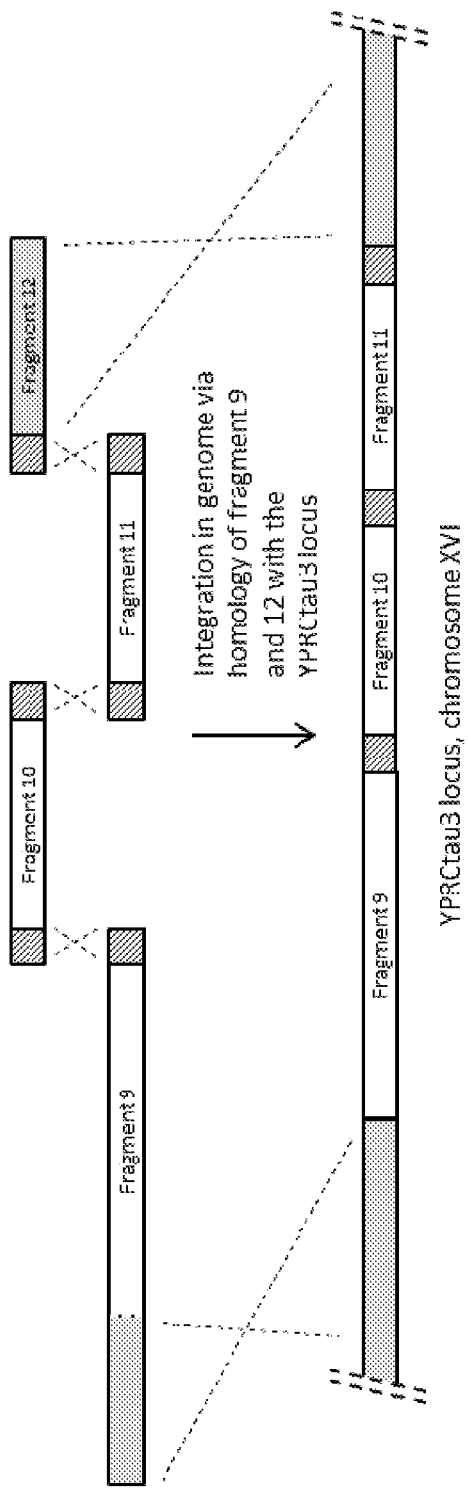
FIG. 1 sets out a schematic depiction of integration of fragments 9 to 12. The hatched parts indicated in fragments 9 to 12 denote the unique homologous overlap regions leading to the recombination events as indicated by the dashed crosses between the homologous regions. The 5' end of fragment 9 and the 3' end of fragment 12 (indicated by the grey regions in fragments 9 and 12) are homologous to the YPRCtau3 locus on chromosome 16. Homologous recombination results in integration of fragment 10 and 11 into the YPRCtau3 locus.

SEQ ID NO: 1 sets out the nucleotide sequence of fragment 2 (FIG. 2), which includes PEP carboxykinase from *Actinobacillus succinogenes* codon pair optimized for expression in *Saccharomyces cerevisiae*.

SEQ ID NO: 2 sets out the nucleotide sequence of fragment 3 (FIG. 2), which includes pyruvate carboxylase (PYC2) from *S. cerevisiae* codon pair optimized for expression in *S. cerevisiae*.

SEQ ID NO: 3 sets out the nucleotide sequence of the PCR template for fragment 4 (FIG. 2), which includes a KanMX selection marker functional in *S. cerevisiae*.

SEQ ID NO: 4 sets out the nucleotide sequence of fragment 5 (FIG. 2), which includes a putative dicarboxylic acid transporter from *Aspergillus niger* codon pair optimized for expression in *S. cerevisiae*.

SEQ ID NO: 5 sets out the nucleotide sequence of fragment 6 (FIG. 2), which includes malate dehydrogenase (MDH3) from *S. cerevisiae* codon pair optimized for expression in *S. cerevisiae*.

SEQ ID NO: 6 sets out the nucleotide sequence of fragment 7 (FIG. 2), which includes fumarase (fumB) from *Escherichia coli* codon pair optimized for expression in *S. cerevisiae*.

SEQ ID NO: 7 sets out the nucleotide sequence of fragment 8 (FIG. 2), which includes fumarate reductase from *Trypanosoma brucei* (FRDg) codon pair optimized for expression in *S. cerevisiae*.

SEQ ID NO: 8 sets out the amino acid sequence of fumarate reductase from *Trypanosoma brucei* (FRDg).

Figure 2:
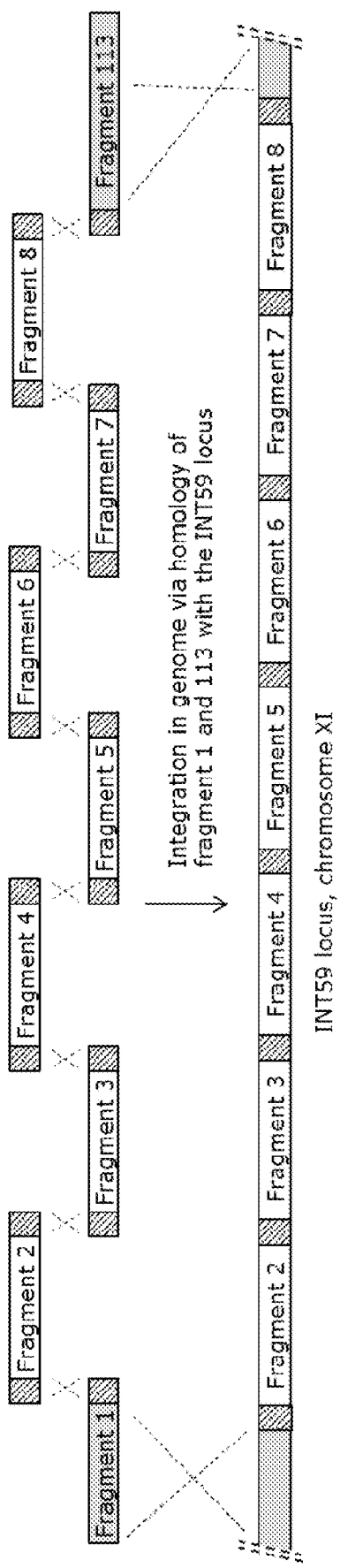
FIG. 2 sets out a schematic depiction of integration of fragments 1-8 and fragment 113. The hatched parts indicated in fragments 1-8 and 113 denote the unique homologous overlap regions leading to the recombination events as indicated by the dashed crosses between the homologous regions. Fragment 1 and fragment 113 are homologous to the INT59 locus on chromosome XI, homologous recombination results in integration of fragment 2-8 into the INT59 locus.

SEQ ID NO: 9 sets out the nucleotide sequence of the primer used to generate fragment 1 (FIG. 2).

SEQ ID NO: 10 sets out the nucleotide sequence of the primer used to generate fragment 1 (FIG. 2).

SEQ ID NO: 11 sets out the nucleotide sequence of the primer used to generate fragment 2 (FIG. 2).

SEQ ID NO: 12 sets out the nucleotide sequence of the primer used to generate fragment 2 (FIG. 2).

SEQ ID NO: 13 sets out the nucleotide sequence of the primer used to generate fragment 3 (FIG. 2).

SEQ ID NO: 14 sets out the nucleotide sequence of the primer used to generate fragment 3 (FIG. 2).

SEQ ID NO: 15 sets out the nucleotide sequence of the primer used to generate fragment 4 (FIG. 2).

SEQ ID NO: 16 sets out the nucleotide sequence of the primer used to generate fragment 4 (FIG. 2).

SEQ ID NO: 17 sets out the nucleotide sequence of the primer used to generate fragment 5 (FIG. 2).

SEQ ID NO: 18 sets out the nucleotide sequence of the primer used to generate fragment 5 (FIG. 2).

Figure 7:
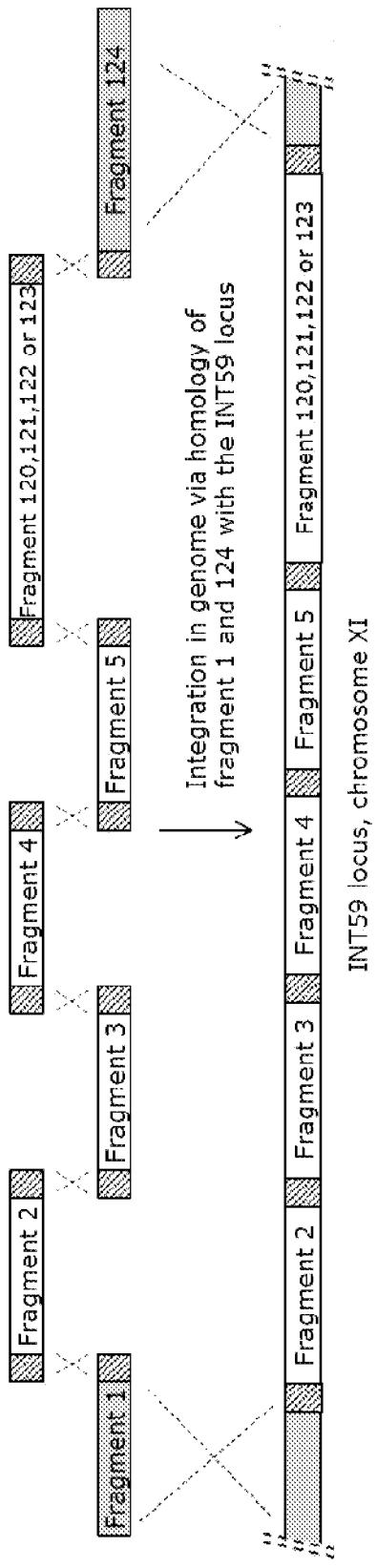
FIG. 7 sets out a schematic depiction of integration of fragments 1-5, 124 and fragment 120, 121, 122 or 123. The hatched parts indicated in the fragments denote the unique homologous overlap regions leading to the recombination events as indicated by the dashed crosses between the homologous regions. Fragment 1 and fragment 124 are homologous to the INT59 locus on chromosome XI, homologous recombination results in integration of fragment 2-5 and 120, 121, 122 or 123 into the INT59 locus.

SEQ ID NO: 19 sets out the nucleotide sequence of the primer used to generate fragment 6 (FIG. 2) and fragments 120, 121, 122 and 123 (FIG. 7).

SEQ ID NO: 20 sets out the nucleotide sequence of the primer used to generate fragment 6 (FIG. 2) and fragments 120, 121, 122 and 123 (FIG. 7).

SEQ ID NO: 21 sets out the nucleotide sequence of the primer used to generate fragment 7 (FIG. 2).

SEQ ID NO: 22 sets out the nucleotide sequence of the primer used to generate fragment 7 (FIG. 2).

SEQ ID NO: 23 sets out the nucleotide sequence of the primer used to generate fragment 8 (FIG. 2).

SEQ ID NO: 24 sets out the nucleotide sequence of the primer used to generate fragment 8 (FIG. 2).

Figure 3:
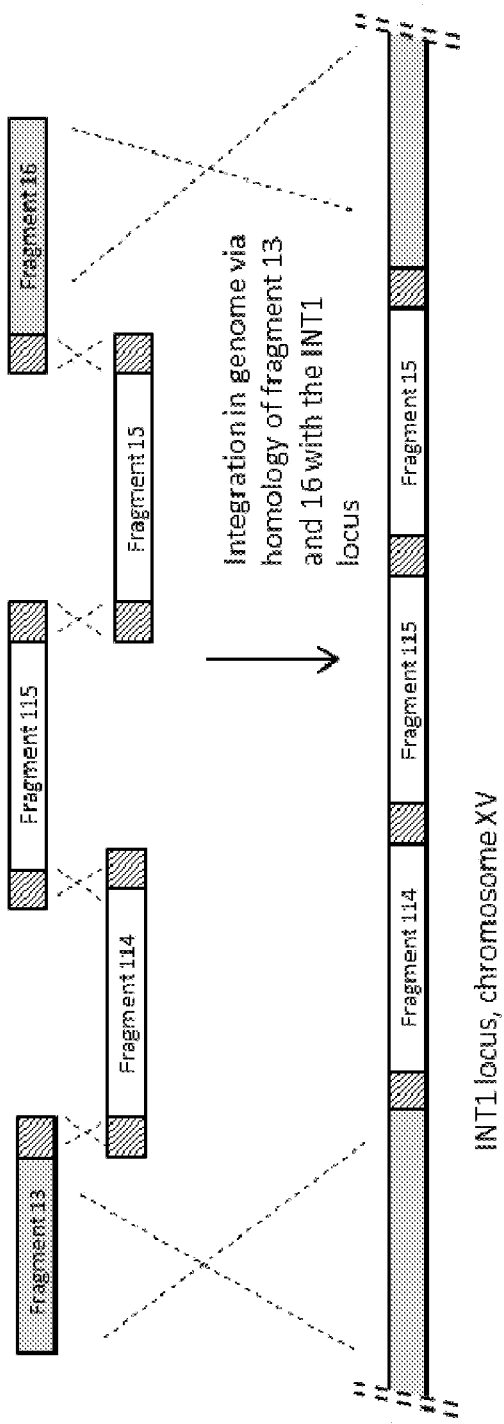
FIG. 3 sets out a schematic depiction of integration of fragments 13, 114, 115, 15 and 16. The hatched parts indicated in fragments 13, 114, 115, 15 and 16 denote the unique homologous overlap regions leading to the recombination events as indicated by the dashed crosses between the homologous regions. Fragment 13 and fragment 16 are homologous to the INT1 locus on chromosome XV, homologous recombination results in integration of fragment 114, 115 and 15 into the INT1 locus.

SEQ ID NO: 25 sets out the nucleotide sequence of the primer used to generate fragment 13 (FIG. 3).

SEQ ID NO: 26 sets out the nucleotide sequence of the primer used to generate fragment 13 (FIG. 3).

Figure 4:
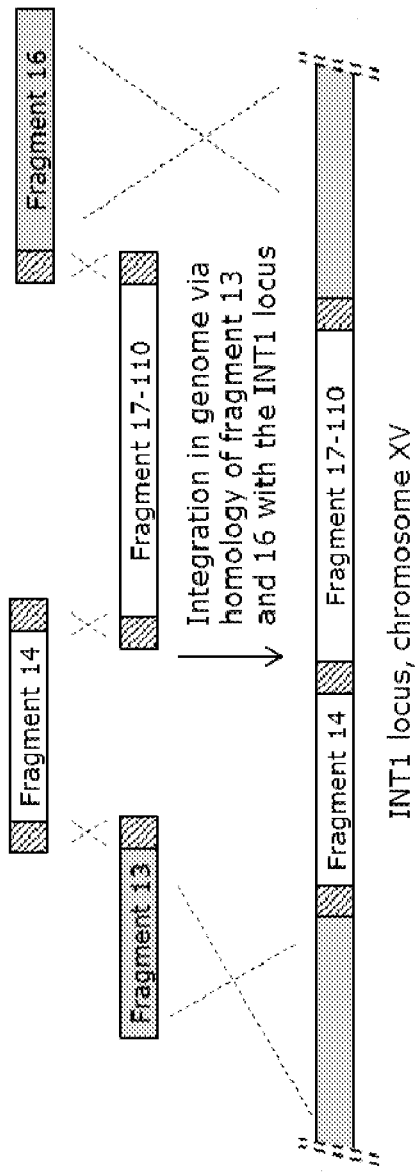
FIG. 4 sets out a schematic depiction of integration of fragments 13, 14, 16 and one of the fragments 17-110. The hatched parts indicated in fragments 13, 14, 16 and fragment 17-110 denote the unique homologous overlap regions leading to the recombination events as indicated by the dashed crosses between the homologous regions. Fragment 13 and fragment 16 are homologous to the INT1 locus on chromosome XV, homologous recombination results in integration of fragment 14 and one of the fragments 17-112 into the INT1 locus.

SEQ ID NO: 27 sets out the nucleotide sequence of the primer used to generate fragment 14 (FIG. 4).

SEQ ID NO: 28 sets out the nucleotide sequence of the primer used to generate fragment 115 (FIG. 3) and fragment 14 (FIG. 4).

SEQ ID NO: 29 sets out the nucleotide sequence of the primer used to generate fragment 15 (FIG. 3) and fragments 17 to 110 (FIG. 4).

SEQ ID NO: 30 sets out the nucleotide sequence of the primer used to generate fragment 15 (FIG. 3) and fragments 17 to 110 (FIG. 4).

SEQ ID NO: 31 sets out the nucleotide sequence of fragment 15 (FIG. 3) and fragment 120 (FIG. 7), which includes the nucleotide sequence encoding SEQ ID NO: 39 codon pair optimized for expression in *S. cerevisiae*.

SEQ ID NO: 32 sets out the nucleotide sequence of the primer used to generate fragment 16 (FIG. 3).

SEQ ID NO: 33 sets out the nucleotide sequence of the primer used to generate fragment 16 (FIG. 3).

SEQ ID NO: 34 sets out the nucleotide sequence of fragment 9 (FIG. 1), which includes fumarase from *Rhizopus oryzae* codon pair optimized for expression in *Saccharomyces cerevisiae*.

SEQ ID NO: 35 sets out the nucleotide sequence of fragment 10 (FIG. 1), which includes the 5' part of the Cre-recombinase.

SEQ ID NO: 36 sets out the nucleotide sequence of fragment 11 (FIG. 1), which includes the 3' part of the Cre-recombinase.

SEQ ID NO: 37 sets out the nucleotide sequence of fragment 12 (FIG. 1), which includes a region homologous to the YPRCtau3 locus.

SEQ ID NO: 38 sets out the nucleotide sequence of the PCR template for fragment 115 (FIG. 3), fragment 14 (FIG. 4) and fragment 117 (FIG. 6), which includes the nourseothricin selection marker.

SEQ ID NO: 39 sets out the amino acid sequence of the malate dehydrogenase (MDH3) protein from *S. cerevisiae*, lacking the 3 C-terminal peroxisomal targeting sequence.

SEQ ID NO: 40 sets out the nucleotide sequence of the primer used to generate fragment 113 (FIG. 2).

SEQ ID NO: 41 sets out the nucleotide sequence of the primer used to generate fragment 113 (FIG. 2).

SEQ ID NO: 42 sets out the nucleotide sequence of fragment 114 (FIG. 3), which includes the expression cassette of ZWF1 from *S. cerevisiae* codon pair optimized for expression in *S. cerevisiae*.

SEQ ID NO: 43 sets out the nucleotide sequence of the primer used to generate fragment 114 (FIG. 3).

SEQ ID NO: 44 sets out the nucleotide sequence of the primer used to generate fragment 114 (FIG. 3).

SEQ ID NO: 45 sets out the nucleotide sequence of the primer used to generate fragment 115 (FIG. 3).

SEQ ID NO: 46 sets out the amino acid sequence of the pyruvate carboxylase protein from *S. cerevisiae*.

SEQ ID NO: 47 sets out the amino acid sequence of phosphoenolpyruvate carboxykinase from *Actinobacillus succinogenes*, with EGY to DAF modification at position 120-122.

SEQ ID NO: 48 sets out the amino acid sequence of fumarase (fumB) from *Escherichia coli*.

SEQ ID NO: 49 sets out the amino acid sequence of fumarase from *Rhizopus oryzae*, lacking the first 23 N-terminal amino acids.

SEQ ID NO: 50 sets out the amino acid sequence of a putative dicarboxylic acid transporter from *Aspergillus niger*.

SEQ ID NO: 51 sets out the amino acid sequence of isocitrate lyase from *Kluyveromyces lactis*.

SEQ ID NO: 52 sets out the amino acid sequence of *Saccharomyces cerevisiae* peroxisomal malate synthase (Mls1) amino acid sequence, lacking the 3 C-terminal peroxisomal targeting sequence.

SEQ ID NO: 53 sets out the amino acid sequence of the malate dehydrogenase (MDH3) protein from *S. cerevisiae*, including the peroxisomal targeting sequence SKL.

Figure 6:
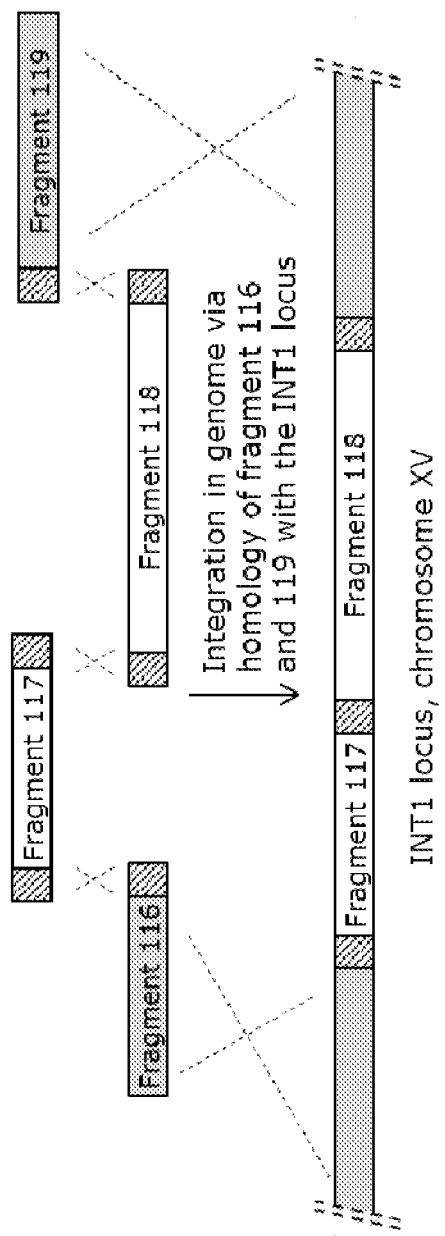
FIG. 6 sets out a schematic depiction of integration of fragments 116, 117, 118 and fragment 119. The hatched parts indicated in fragments 116, 117, 118 and fragment 119 denote the unique homologous overlap regions leading to the recombination events as indicated by the dashed crosses between the homologous regions. Fragment 116 and fragment 119 are homologous to the INT1 locus on chromosome XV, homologous recombination results in integration of fragment 117 and fragment 118 into the INT1 locus.

SEQ ID NO: 54 sets out the nucleotide sequence of the primer used to generate fragment 116 (FIG. 6).

SEQ ID NO: 55 sets out the nucleotide sequence of the primer used to generate fragment 116 (FIG. 6).

SEQ ID NO: 56 sets out the nucleotide sequence of the primer used to generate fragment 117 (FIG. 6).

SEQ ID NO: 57 sets out the nucleotide sequence of the primer used to generate fragment 117 (FIG. 6).

SEQ ID NO: 58 sets out the nucleotide sequence of the primer used to generate fragment 119 (FIG. 6).

SEQ ID NO: 59 sets out the nucleotide sequence of the primer used to generate fragment 119 (FIG. 6).

SEQ ID NO: 60 sets out the nucleotide sequence of the primer used to generate fragment 118 (FIG. 6).

SEQ ID NO: 61 sets out the nucleotide sequence of the primer used to generate fragment 118 (FIG. 6).

SEQ ID NO: 62 sets out the nucleotide sequence of fragment 118 (FIG. 6) which includes coding sequence for fumarate reductase from *Trypanosoma brucei* (FRDg) codon pair optimized for expression in *S. cerevisiae*.

SEQ ID NO: 63 sets out the nucleotide sequence of the primer used to generate fragment 124 (FIG. 7).

SEQ ID NO: 64 sets out the nucleotide sequence of fragment 121 (FIG. 7) which includes coding sequence for *S. cerevisiae* MDH3 mutant MUT_014 codon pair optimized for expression in *S. cerevisiae*.

SEQ ID NO: 65 sets out the nucleotide sequence of fragment 122 (FIG. 7) which includes coding sequence for *S. cerevisiae* MDH3 mutant MUT_015 codon pair optimized for expression in *S. cerevisiae*.

SEQ ID NO: 66 sets out the nucleotide sequence of fragment 123 (FIG. 7) which includes coding sequence for *S. cerevisiae* MDH3 mutant MUT_034 codon pair optimized for expression in *S. cerevisiae*.

SEQ ID NO: 67 sets out the amino acid sequence of fumarase from *Arabidopsis thaliana*.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The reductive TCA pathway is one of the primary pathways by which a microorganism can produce dicarboxylic acids. In recent years, it has proven to be the best economic option for the microbial production of dicarboxylic acids, e.g. succinic acid. The reductive TCA pathway includes two reactions which require the consumption of reducing power; i.e. the malate dehydrogenase reaction (reduction of oxaloacetate to malate) and the fumarate reductase reaction (reduction of fumarate to succinate).

Malate dehydrogenase (MDH) catalyzes the reversible conversion of malate to oxaloacetate using NAD or NADP as the cofactor (also collectively referred as NAD(P)). MDH is a rather ubiquitous enzyme and plays crucial roles in many metabolic pathways, including the tricarboxylic acid cycle, amino acid synthesis, gluconeogenesis, maintenance of the oxidation/reduction balance and metabolic stress.

MDHs can be divided into NAD(H)-dependent MDHs (NAD-MDH) (EC 1.1.1.37) and NADP(H)-dependent MDHs (NADP-MDH) (EC 1.1.1.82), according to their preference for cofactors. Most bacterial and archaeal MDHs are NAD-MDHs. Eukaryotic MDH isoforms are all NAD-MDHs, including mitochondrial MDHs, cytosolic MDHs, glyoxysomal MDHs, and peroxisomal MDHs, except for chloroplastic NADP-MDHs, which are required for the transfer of reducing equivalents from chloroplast stroma to cytosol. In the yeast *Saccharomyces cerevisiae*, three endogenous isoenzymes of malate dehydrogeneases have been identified, namely MDH1, MDH2 and MDH3. They were located in the mitochondria (MDH1), the cytosol (MDH2) and the peroxisome (MDH3) and were all characterized to be NAD(H)-dependent MDHs (EC 1.1.1.37).

The study of NAD(P)-binding domains in the malate dehydrogenase enzyme family revealed a conserved βB-αC motif of the Rossmann fold. The ability of the dehydrogenases to discriminate against NADP(H) lies in the amino acid sequence of this βB-αC motif, which has been predicted to be a principal determinant for cofactor specificity. For example, in the *S. cerevisiae* peroxisomal NAD-MDH (MDH3), the NAD-binding motif includes amino acid residues 34 to 40 which were found important for cofactor binding and specificity.

In the context of the present invention, it has been surprisingly found that a set of specific mutations in the conserved NAD-binding motif of a polypeptide having MDH activity confers an increased production of a dicarboxylic acid when (over)expressed in a recombinant host cell capable of the production of said dicarboxylic acid. That is to say, (over)expression of said mutant polypeptide having MDH activity in a recombinant host cell typically leads to increased production of a dicarboxylic acid as compared to a recombinant host cell which (over)expresses a reference MDH polypeptide; the "reference MDH polypeptide" being typically a NAD-MDH (EC 1.1.1.37). Concomitantly, it has been shown that said mutant polypeptide having at least one mutation in the conserved NAD-binding motif has an increase in the NADP(H)- relative to NAD(H)-dependent activity as compared to that of said reference MDH polypeptide. Surprisingly, the inventors of the present invention have further shown that the NADP(H)-dependent activity does not have to be higher than the NAD(H)-dependent activity to obtain an increase in dicarboxylic acid production.

It is therefore an object of the present invention to provide a recombinant host cell which is capable of producing a dicarboxylic acid and which comprises a mutant polypeptide having malate dehydrogenase (MDH) activity.

In one embodiment, the mutant polypeptide having malate dehydrogenase activity comprises an amino acid sequence which, when aligned with the malate dehydrogenase comprising the sequence set out in SEQ ID NO: 39, comprises one mutation of an amino acid residue corresponding to amino acid 34 in SEQ ID NO: 39. In other words, said mutant polypeptide comprises one mutation of an amino acid residue occurring at a position corresponding to 34 in SEQ ID NO: 39.

In a preferred embodiment of the invention, the mutation of the amino acid corresponding to amino acid 34 (as defined with reference to SEQ ID NO: 39) will be a substitution.

More preferably, the substitution of the amino acid corresponding to amino acid 34 (as defined with reference to SEQ ID NO: 39) will typically be to a small amino acid. Suitable small amino acids include threonine (T), serine (S), glycine (G), alanine (A) and proline (P). Preferred small amino acids are glycine (G) and serine (S).

In the context of the present invention, a "recombinant host cell" or a "genetically modified host cell" is a host cell into which has been introduced, by means of recombinant DNA techniques, a nucleic acid, a nucleic acid construct or a vector comprising a nucleic acid sequence encoding a mutant polypeptide having malate dehydrogenase activity.

Herein, a "mutant polypeptide having malate dehydrogenase (MDH) activity" may be referred to as a "mutant malate dehydrogenase", "MDH mutant", "MDH mutant polypeptide", "mutant", "mutant polypeptide" or the like.

Herein, the "malate dehydrogenase activity" is the activity converting oxaloacetic acid to malic acid:

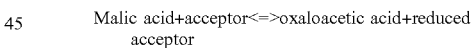

Malic acid+acceptor<=>oxaloacetic acid+reduced acceptor

The term "polypeptide" is used herein for chains containing more than about seven amino acid residues. All polypeptide sequences herein are written from left to right and in the direction from amino terminus to carboxy terminus. The one-letter code of amino acids used herein is commonly known in the art and can be found in Sambrook et al. (Molecular Cloning: A Laboratory Manual, 3rd edition, *Cold Spring Harbor Laboratory Press*, Cold Spring Harbor Laboratory, NY, 2001).

In the context of the present invention, a "mutant" polypeptide is defined as a polypeptide which was obtained by introduction of one or more mutations. Said mutations may be selected from the group of substitutions, additions and deletions. The term "substitution" herein means the replacement of an amino acid residue in the polypeptide sequence with another one. A "mutant" polypeptide, a "mutated" polypeptide and a "genetically engineered" polypeptide have the same meaning and are used interchangeably.

Herein, a "corresponding position" refers to the vertical column in an amino acid sequence alignment between SEQ ID NO: 39 and sequences homologous to SEQ ID NO: 39 corresponding to a specific position in SEQ ID NO:39 and showing the amino acids that occur at this position in the other aligned homologues.

In the context of the invention, a "corresponding mutation" refers to a mutation of an amino acid residue occurring at a "corresponding position" in SEQ ID NO: 39. For example, a "corresponding substitution" refers to a substitution of an amino acid residue occurring at a "corresponding position" in SEQ ID NO: 39 with another amino acid residue.

In some further embodiments, the mutant polypeptide having malate dehydrogenase activity may further comprise one or more additional mutations corresponding to any of amino acids 35, 36, 37, 38, 39 and/or 40 in SEQ ID NO: 39. Said mutations will typically be selected from the group of substitutions, additions and deletions. More preferably, the one or more additional mutations will be a substitution.

The substitution of the amino acid corresponding to amino acid 35 (as defined with reference to SEQ ID NO: 39) will typically be to a small amino acid. Suitable small amino acids include threonine (T), serine (S), glycine (G), alanine (A) and proline (P). Alternatively, the substitution of the amino acid corresponding to amino acid 35 (as defined with reference to SEQ ID NO: 39) will be to a hydrophobic amino acid, such as isoleucine (I). A preferred substitution of the amino acid corresponding to amino acid 35 (as defined with reference to SEQ ID NO: 39) will be to serine (S) or isoleucine (I).

The substitution of the amino acid corresponding to amino acid 36 (as defined with reference to SEQ ID NO: 39) will typically be to a polar amino acid. Suitable polar amino acids include arginine (R), glutamine (Q), Glutamic acid (E) and serine (S). Alternatively, the substitution of the amino acid corresponding to amino acid 36 (as defined with reference to SEQ ID NO: 39) will be to a small amino acid, such as alanine (A) or proline (P). A preferred substitution of the amino acid corresponding to amino acid 36 (as defined with reference to SEQ ID NO: 39) will be to arginine (R), glutamine (Q), glutamic acid (E), serine (S), alanine (A) or proline (P).

The substitution of the amino acid corresponding to amino acid 37 (as defined with reference to SEQ ID NO: 39) will typically be to a small amino acid. Suitable small amino acids include glycine (G), asparagine (N), and alanine (A). Alternatively, the substitution of the amino acid corresponding to amino acid 37 (as defined with reference to SEQ ID NO: 39) will be to a polar amino acid, such as arginine (R) or glutamine (Q). A preferred substitution of the amino acid corresponding to amino acid 37 (as defined with reference to SEQ ID NO: 39) will be to (G), asparagine (N), alanine (A), alanine arginine (R) or glutamine (Q).

The substitution of the amino acid corresponding to amino acid 38 (as defined with reference to SEQ ID NO: 39) will typically be to a small amino acid. Suitable small amino acids include valine (V), threonine (T), serine (S), glycine (G), alanine (A) and proline (P). A preferred substitution of the amino acid corresponding to amino acid 38 (as defined with reference to SEQ ID NO: 39) will be to alanine (A), valine (V), threonine (T) or serine (S).

The substitution of the amino acid corresponding to amino acid 39 (as defined with reference to SEQ ID NO: 39) will typically be to a small amino acid. A suitable small amino acid includes proline (P). Alternatively, the substitution of the amino acid corresponding to amino acid 39 (as defined with reference to SEQ ID NO: 39) will be to a hydrophobic amino acid, such as lysine (K), phenylalanine (F) or leucine (L). Alternatively, the substitution of the amino acid corresponding to amino acid 39 (as defined with reference to SEQ ID NO: 39) will be to a polar amino acid, such as glutamic acid (E). A preferred substitution of the amino acid corresponding to amino acid 39 (as defined with reference to SEQ ID NO: 39) will be to glutamic acid (E), lysine (K), phenylalanine (F), leucine (L) or proline (P).

The substitution of the amino acid corresponding to amino acid 40 (as defined with reference to SEQ ID NO: 39) will typically be to a small amino acid. Suitable small amino acids include glycine (G). Alternatively, the substitution of the amino acid corresponding to amino acid 40 (as defined with reference to SEQ ID NO: 39) will be to a polar amino acid, such as glutamine (Q). A preferred substitution of the amino acid corresponding to amino acid 40 (as defined with reference to SEQ ID NO: 39) will be to glycine (G) or glutamine (Q).

The various types of amino acids above are classified with reference to, for example, Betts and Russell, In Bioinformatics for Geneticists, Barnes and Gray eds, Wiley 2003.

In more detail, in the context of the invention, a mutant polypeptide having malate dehydrogenase activity will comprise G or S at position 34 as defined with reference to SEQ ID NO: 39;

and, optionally

I or S at position 35 as defined with reference to SEQ ID NO: 39; and/or

R, Q, A, E, P or S at position 36 as defined with reference to SEQ ID NO: 39; and/or A, N, G, R or Q at position 37 as defined with reference to SEQ ID NO: 39; and/or A, V, T or S at position 38 as defined with reference to SEQ ID NO: 39; and/or E, K, P, F or L at position 39 as defined with reference to SEQ ID NO: 39; and/or G or Q at position 40 as defined with reference to SEQ ID NO: 39.

In one specific embodiment, a mutant polypeptide having malate dehydrogenase activity will comprise a small amino acid at position 34 (as defined with reference to SEQ ID NO: 39) and a small or polar amino acid at position 36 (as defined with reference to SEQ ID NO: 39). In said embodiment, a preferred small amino acid at position 34 may be selected from G or S. In said embodiment, a preferred small or polar amino acid at position 36 may be selected from R, Q, A, E, P or S. Optionally, in said embodiment, the mutant polypeptide will comprise I or S at position 35 as defined with reference to SEQ ID NO: 39; and/or A, N, G, R or Q at position 37 as defined with reference to SEQ ID NO: 39; and/or A, V, T or S at position 38 as defined with reference to SEQ ID NO: 39; and/or E, K, P, F or L at position 39 as defined with reference to SEQ ID NO: 39; and/or G or Q at position 40 as defined with reference to SEQ ID NO: 39.

The mutant polypeptide having MDH activity may furthermore comprises additional mutations other than the seven positions defined above, for example, one or more additional substitutions, additions or deletions.

The mutant polypeptide having MDH activity may comprise a combination of different types of modification of this sort. The mutant polypeptide having MDH activity may comprise one, two, three, four, least 5, at least 10, at least 15, at least 20, at least 25, at least 30 or more such modifications (which may all be of the same type or may be different types of modification). Typically, the additional modifications may be substitutions.

In yet further embodiments, the mutant polypeptide having malate dehydrogenase activity is as defined with reference to Table 1 (Example 4) and wherein the amino acid residue corresponding to amino acid 34 in SEQ ID NO: 39 is selected from glycine (G) or serine (S). That is to say, the mutant polypeptide may comprise any combination of substitutions as set out in Table 1 as compared to a suitable reference sequence such as that set out in SEQ ID NO: 39, and wherein the amino acid residue corresponding to amino acid 34 in SEQ ID NO: 39 is selected from glycine (G) or serine (S).

Typically, then the mutant polypeptide may comprise the sequence of SEQ ID NO: 39 with one substitution at position 34, and optionally one or more substitutions at 35, 36, 37, 38, 39 and/or 40. That is to say, the mutant polypeptide will have an amino acid other than aspartate at position 34 and optionally an amino acid other than isoleucine at position 35 and/or an amino acid other than arginine at position 36 and/or an amino acid other than alanine at position 37, and/or an amino acid other than alanine at position 38, and/or an amino acid other than glutamate at position 39, and/or an amino acid other than glycine at position 40.

Also, typically, the mutant polypeptide may comprise the sequence of SEQ ID NO: 39 with one substitution at position 34, one substitution at position 36, and optionally one or more substitutions at 35, 37, 38, 39 and/or 40. That is to say, the mutant polypeptide will have an amino acid other than aspartate at position 34, an amino acid other than arginine at position 36, and optionally an amino acid other than isoleucine at position 35 and/or an amino acid other than alanine at position 37, and/or an amino acid other than alanine at position 38, and/or an amino acid other than glutamate at position 39, and/or an amino acid other than glycine at position 40.

In a separate embodiment of the present invention, the mutant polypeptide having malate dehydrogenase activity has an increase in the NADP(H)- relative to NAD(H)-dependent activity as compared to that of a reference MDH polypeptide. In said embodiment, said mutant polypeptide may be a mutant polypeptide comprising an amino acid sequence which, when aligned with the malate dehydrogenase comprising the sequence set out in SEQ ID NO: 39, comprises one mutation (e.g. one substitution) of an amino acid residue corresponding to amino acid 34 in SEQ ID NO: 39. Further embodiments with regard to the amino acid sequence of said mutant polypeptide are as described herein above.

In the context of the invention, a reference polypeptide having malate dehydrogenase activity, also called a "reference MDH polypeptide", may be NAD-MDH (EC 1.1.1.37). A reference polypeptide having malate dehydrogenase activity may be a malate dehydrogenase from a microbial source, such as a yeast (e.g. *Saccharomyces cerevisiae*). A malate dehydrogenase having the amino acid sequence set out in SEQ ID NO: 39 may be a suitable reference polypeptide having MDH activity.

The expression "increase in NADP(H)- relative to NAD(H)-dependent activity" herein typically refers to the property of a mutant polypeptide to show an increase in NADP(H)- relative to NAD(H)-dependent activity in comparison to that of a reference MDH polypeptide, for example in comparison to SEQ ID NO: 39. That is to say a mutant polypeptide may show an increase in the ratio of NADP(H)- to NAD(H)-dependent activity in comparison to that of a reference polypeptide. In Example 5, the ratio is also referred as the "NADPH:NADH specificity ratio".

In the context of the present invention, the terms "NADP(H)-dependent activity" and "NADP(H)-specific activity" have the same meaning herein and are used interchangeably. Same applies for the terms "NAD(H)-dependent activity" and "NAD(H)-specific activity".

The term "NADP(H)-dependent activity" herein refers to the property of an enzyme to use NADP(H) as the redox cofactor. The NADP(H)-dependent activity of the enzyme may be determined by an enzyme activity assay such as described in Example 5.

The term "NAD(H)-dependent activity" herein refers to the property of an enzyme to use NAD(H) as the redox cofactor. The NAD(H)-dependent activity of the enzyme may be determined by an enzyme activity assay such described in Example 5.

An increased value of the average NADPH:NADH specificity ratio may indicate, for example, a reduced NAD(H)-dependent activity, an increased NADP(H)-dependent activity or a combination of the two. In some cases, an increased value of said ratio may be obtained with a MDH mutant having a similar or increased NAD(H)-dependent activity in comparison to a reference MDH. In the latter cases, it may be that the MDH mutant displays both increased NAD(H)- and NADP(H)-dependent activities.

The mutant MDH polypeptide will typically have modified MDH activity in terms of modified cofactor dependence. This NAD(H)- or NADP(H)-dependent activity may be modified independent from each other, for example decreased, by at least 10%, at least 20%, at least 30%, at least 40%, at least 50%, at least 60%, at least 70%, at least 80%, at least 90%, at least 95% or at least 99%. Alternatively, the property may be increased by at least 10%, at least 25%, at least 50%, at least 70%, at least 100%, at least, 200%, at least 500%, at least 700%, at least 1000%, at least 3000%, at least 5000%, or at least 6000%.

In one specific embodiment, the NAD(H)- and NADP(H)-dependent activities of the mutant MDH polypeptide are both increased. The NAD(H)-dependent activity of said mutant MDH polypeptide is increased by at least 10%, at least 25%, at least 50%, at least 70%, at least 100%, at least, 200%, or at least 300%. The NADP(H)-dependent activity of said mutant MDH polypeptide is increased by at least 10%, at least 25%, at least 50%, at least 70%, at least 100%, at least, 200%, at least 500%, at least 700%, at least 1000%, at least 3000%, at least 5000%, or at least 6000%.

In another embodiment, the NAD(H)-dependent activity of the mutant MDH polypeptide is about the same or decreased by at most 5%, at most 10%, at most 20%, at most 30%, at most 40%, at most 50%, at most 60%, at most 70%, at most 80% and the NADP(H)-dependent activity of said mutant MDH polypeptide is increased by at least 10%, at least 25%, at least 50%, at least 70%, at least 100%, at least, 200%, at least 500%, at least 700%, at least 1000%, at least 3000%, at least 5000%, or at least 6000%.

In another embodiment, the NADPH:NADH specificity ratio of the mutant MDH polypeptide is increased by at least 10%, at least 50%, at least 100%, at least, 200%, at least 500%, at least 1000%, at least 3000%, at least 5000%, at least 7000%, or at least 8000%.

The percentage decrease or increase in this context represents the percentage decrease or increase in comparison to the reference MDH polypeptide, for example that of SEQ ID NO: 39. It is well known to the skilled person how such percentage changes may be measured—it is a comparison of the activity, for example NAD(H)- or NADP(H)-dependent activity, of the reference MDH and the mutant MDH measured as set out in the Examples.

In the context of the present invention, the MDH mutant polypeptide as described herein above may be a mutant NAD(P)-malate dehydrogenase, such as a mutant mitochondrial NAD-MDH, a mutant cytosolic NAD-MDH, a mutant glyoxysomal NAD-MDH, a mutant peroxisomal NAD-MDH, or a mutant chloroplastic NADP-MDH. That is to say, the mutant polypeptide having malate dehydrogenase activity may be obtained by introduction of one or more mutations in a NAD(P)-malate dehydrogenase, such as a mitochondrial NAD-MDH, cytosolic NAD-MDH, glyoxysomal NAD-MDH, peroxisomal NAD-MDH, or a chloroplastic NADP-MDH (the latter being referred as template MDH polypeptides for introducing said one or more mutations). Preferably, the mutant polypeptide having malate dehydrogenase activity is a mutant NAD(H)-malate dehydrogenase (EC 1.1.1.37). More preferably, the mutant polypeptide having malate dehydrogenase activity is a mutant peroxisomal NAD(H)-malate dehydrogenase. Even more preferably, the mutant polypeptide having malate dehydrogenase activity is a mutant NAD(H)-malate dehydrogenase from a yeast or a fungus. Even more preferably, the mutant polypeptide having malate dehydrogenase activity is a mutant NAD(H)-malate dehydrogenase from a yeast or fungus, such as S. cerevisiae, Torulaspora delbrueckii, Zygosaccharomyces bailiff, Naumovozyma castellii, Naumovozyma dairenensis, Lachancea lanzarotensis, Zygosaccharomyces rouxii, Kazachstania Africana, Candida tropicalis, Kluyveromyces marxianus, Scheffersomyces stipites, Talaromyces marneffei, Rasamsonia emersonii, Aspergillus niger, or Trametes versicolor. The following Uniprot database codes refer to suitable yeast and fungal template MDH polypeptides (http://www.uniprot.org): E7NGH7, G8ZXS3, G0V668, W0VUI8, G0WB63, A0A0W0D4X6, A0A0C7MME9, C5DQ42, C5DI45, H2AWW6, A0A090C493, J7R0C8, Q6CJP3, Q759M4, I2H037, C5M546, A7TL95, A0A0L0P3G3, Q6BM17, S8AW17, V5FMV2, A3LW84, A0A109UZS1, G8BVW8, G8BJ12, M3HPK4, A0A093UW53, B8MTP0, A0A0F4YPR0, C8V0H6, W6QNU3, A5DZ33, U1GAT6, G3B7S5, C4JPI7, A0A0F8UZY9, Q4WDM0, A0A093UPX3, B8ND04, A0A0M9VRI4, G7XZ98, Q5A5S6, M7S9E4, E4UYX5, A5DE02, A0A0J7BIJ5, A0A017SKI1, G8Y7A1, A0A0G2EFQ2, R7S165, I1RFM4, R1EVC8, U4L6K9, A0A0L0P507, W7HM94, A5DGY9, F2QY33, A0A0G2JA24, UPI000462180C, C7Z9W6, E5AAQ2, B2VVR8, A0A0H2RCV1, A8Q524, A0A0E9N879, N1JA02, A0A0D1ZEE3, J5T1X5, W6MY07, C4Y826, G3AJA2, G9N6G5, A0A0K8L6L9, A3GH28, A8P7W6, K5W0T4, G1XT67, A0A0B7K175, B8MTP5, A0A0D1ZAS7, A0A0C3BQC4, K5Y2Q9, A0A0C3DSW4, A0A068S518, W2RPL2, A0A0H5C453, A0A074WKG5, G8JRX4, A0A0U1M134, H6C0V9, A0A0H5BZ30, M2UXR7, A0A0C9YJV6, A0A0C3S6T1, W1QK02, A0A0C2YFC4, A0A061AJ54, A0A086T183, W2RVT1, UPI0004623914, A0A0C9X7U1, UPI0001 F26169, G7E054, A0A0C2S9T3, A0A067NIX1, L8FPM0, G3ALW4, A0A0D0AYX2, G0VJG3, A0A0D2NGY0, C1GLB8, W9X415, A0A0D0CDE8, S7Q8G0, A0A0C9TB51, R7YP89, A0A0C2W4H8, UPI000455FA04, A0A067NL73, A0A067STP4, W9WWP5, A0A0D7A9T7, A0A0D6R2E1, M2YLX9, G0W7D4, N1QJ61, G4TRY5, F0XJ10, A0A063BQQ6, A0A061HBX5, A0A0A1PCT2, M1WIC4, A8QAQ2, A0A0C3N631, F2QTL7, A0A060S7U3, A0A0L0HTQ9, Q0CKY1, A0A0C2ZJ90, K5W527, I4Y5C3, R7YXZ2, F9XI12, A0A061J968, F9XL74, A0A0D0BEW9, A0A0C9WB72, F7WA21, A8NJ67, M2P8M6, W4KHW3, A0A0L1I2T4, UPI0004449A9D, P83778, C4Y9Q7, A0A0D7BHV7, A0A068RWX9, M2YWQ3, A0A137QV51, A0A0D0B6C2, I1BQQ7, S3DA07, Q4DXL5, G8Y022, A0A0C9W9B3, A0A0L6WJ49, A0A0L9SL52, D5GA85, A0A0N1J4Z6, J7S1G2, A0A0F4X5C6, Q6CIK3, A0A067QNN0, Q0UGT7, F8ND69, U5HIM0, J3NKC7, A0A061ATZ7, A5DSY0, Q9Y750, UPI0004F4119A, A0A086TL69, A0A0J0XSS4, UPI0003F496E1, UPI000455F0EA, S7RXX1, A0A067NAG9, A0A0B7N3M5, E6ZKH0, C8V1V3, A7UFI6, T5AEM1, A0A072PGA9, A0A094EKH6, S8ADX4, G8C073, Q6BXI8, G2R916 and U9TUL6. Even more preferably, the mutant polypeptide having malate dehydrogenase activity is a mutant S. cerevisiae peroxisomal NAD-MDH (MDH3).

Additionally, in the recombinant host cell of the invention, the mutant polypeptide having malate dehydrogenase activity may be a mutant of a homologous or heterologous NAD(P)-malate dehydrogenase. In a preferred embodiment, the MDH mutant is a mutant of a homologous NAD(P)-malate dehydrogenase. More preferably, the MDH mutant is a mutant of a homologous NAD(H)-malate dehydrogenase (EC 1.1.1.37). More preferably, the mutant polypeptide having malate dehydrogenase activity is a mutant of a homologous peroxisomal NAD(H)-malate dehydrogenase.

In this context, the term "homologous" or "endogenous" when used to indicate the relation between a given (recombinant) nucleic acid or polypeptide molecule and a given host organism or host cell, is understood to mean that in nature the nucleic acid or polypeptide molecule is produced by a host cell or organism of the same species, preferably of the same variety or strain.

The term "heterologous" as used herein refers to nucleic acid or amino acid sequences not naturally occurring in a host cell. In other words, the nucleic acid or amino acid sequence is not identical to that naturally found in the host cell.

Preferably, in a recombinant host cell of the present invention, the nucleic sequence encoding said mutant polypeptide having malate dehydrogenase activity is expressed in the cytosol and the mutant polypeptide having malate dehydrogenase activity is active in the cytosol. In some instances, cytosolic expression may be obtained by deletion of a peroxisomal or mitochondrial targeting signal. The presence of a peroxisomal or mitochondrial targeting signal may for instance be determined by the method disclosed by Schlüter et al., Nucleid Acid Research 2007, 35, D815-D822. When the MDH mutant is a mutant S. cerevisiae peroxisomal NAD-MDH (e.g. a mutant MDH3), its C-terminal SKL is preferably deleted such that it is active in the cytosol.

Typically, the mutant polypeptide having malate dehydrogenase activity may have at least about 40%, 50%, 60%, 70%, 80% sequence identity with a reference MDH polypeptide, such as the MDH of SEQ ID NO: 53 or SEQ ID NO: 39, for example at least 85% sequence identity with a reference MDH polypeptide, such as at least about 90% sequence identity with a reference MDH polypeptide, at least 95% sequence identity with a reference MDH polypeptide, at least 98% sequence identity with a reference MDH polypeptide or at least 99% sequence identity with a reference MDH polypeptide.

It has been surprisingly found that said mutant MDH polypeptide as described herein above confers an increase in the production of a dicarboxylic acid in a recombinant host cell when said mutant is (over)expressed in said recombinant host cell as compared to the production level of an equivalent recombinant host cell which (over)expresses a reference polypeptide having MDH activity; the "reference MDH polypeptide" being typically a NAD-MDH (EC 1.1.1.37), for example a malate dehydrogenase having an amino acid sequence set out in SEQ ID NO: 39.

Accordingly, there is thus provided a recombinant host cell which is capable of producing or produces a dicarboxylic acid and which comprises a nucleic acid sequence encoding a mutant polypeptide having malate dehydrogenase activity as described herein above.

A recombinant host cell of the invention is capable of producing or produces a dicarboxylic acid, such as malic acid, fumaric acid and/or succinic acid.

The terms "dicarboxylic acid" and "dicarboxylate", such as "succinic acid" and "succinate", have the same meaning herein and are used interchangeably, the first being the hydrogenated form of the latter.

Typically, the recombinant host cell of the invention will produce an increased amount of a dicarboxylic acid in comparison to a recombinant host cell expressing a reference MDH polypeptide, for example that of SEQ ID NO: 39. The production of a dicarboxylic acid may be increased, by at least 5%, 10%, at least 20%, at least 30%, at least 40% at least 50%, at least 60%, at least 70%, at least 80%, at least 90%, at least 95%, or at least 100% or more. Production level may be expressed in terms of g/L, so an increase in the production level of a dicarboxylic acid will be evident by higher level of production in terms of g/L.

The recombinant host cell of the invention or a parent of said host cell may be any type of host cell. Accordingly, both prokaryotic and eukaryotic cells are included. Host cells may also include, but are not limited to, mammalian cell lines such as CHO, VERO, BHK, HeLa, COS, MDCK, 293, 3T3, WI38, and choroid plexus cell lines.

A suitable host cell of the invention may be a prokaryotic cell. Preferably, the prokaryotic cell is a bacterial cell. The term "bacterial cell" includes both Gram-negative and Gram-positive microorganisms.

Suitable bacteria may be selected from e.g. *Escherichia, Actinobacillus, Anabaena, Caulobactert, Gluconobacter, Mannheimia, Basfia, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or Actinomycetes such as *Streptomyces* and *Actinoplanes* species. Preferably, the bacterial cell is selected from the group consisting of *Bacillus subtilis, B. amyloliquefaciens, B. licheniformis, B. puntis, B. megaterium, B. halodurans, B. pumilus, Actinobacillus succinogenes, Gluconobacter oxydans, Caulobacter crescentus* CB 15, *Methylobacterium extorquens, Rhodobacter sphaeroides, Pseudomonas zeaxanthinifaciens, Pseudomonas putida, Pseudomonas fluorescens, Paracoccus denitrificans, Escherichia coli, Corynebacterium glutamicum, Mannheimia succinoproducens, Basfia succinoproducens, Staphylococcus carnosus, Streptomyces lividans, Streptomyces clavuligerus, Sinorhizobium melioti* and *Rhizobium radiobacter.*

A host cell according to the invention may be a eukaryotic host cell. Preferably, the eukaryotic cell is a mammalian, insect, plant, fungal, or algal cell. More preferably, the eukaryotic cell is a fungal cell. A suitable fungal cell may for instance belong to genera *Saccharomyces, Schizosaccharomyces, Aspergillus, Penicillium, Pichia, Kluyveromyces, Yarrowia, Candida, Hansenula, Humicola, Pichia, Issatchenkia, Kloeckera, Schwanniomyces, Torulaspora, Trichosporon, Brettanomyces, Rhizopus, Zygosaccharomyces, Pachysolen* or *Yamadazyma*. A fungal cell may for instance belong to a species of *Saccharomyces cerevisiae, S. uvarum, S. bayanus S. pastorianus, S. carlsbergensis, Aspergillus niger, Penicillium chrysogenum, Pichia stipidis, P. pastoris, Kluyveromyces marxianus, K. lactis, K. thermotolerans, Yarrowia lipolytica, Candida sonorensis, C. revkaufi, C. pulcherrima, C. tropicalis, C. utilis, C. kruisei, C. glabrata, Hansenula polymorpha, Issatchenkia orientalis, Torulaspora delbrueckii, Brettanomyces bruxellensis, Rhizopus oryzae* or *Zygosaccharomyces bailii*. In one embodiment, a fungal cell of the present invention is a yeast, for instance belonging to a *Saccharomyces* sp., such as a *Saccharomyces cerevisiae*.

Examples of specific host yeast cells include *C. sonorensis, K. marxianus, K. thermotolerans, C. methanesorbosa, Saccharomyces bulderi (S. bulden), P. kudriavzevii, I. orientalis, C. lambica, C. sorboxylosa, C. zemplinina, C. geochares, P. membranifaciens, Z. kombuchaensis, C. sorbosivorans, C. vanderwaltii, C. sorbophila, Z bisporus, Z. lentus, Saccharomyces bayanus (S. bayanus), D. castellii, C, boidinii, C. etchellsii, K. lactis, P. jadinii, P. anomala, Saccharomyces cerevisiae (S. cerevisiae), Pichia galeiformis, Pichia* sp. YB-4149 (NRRL designation), *Candida ethanolica, P. deserticola, P. membranifaciens, P. fermentans* and *Saccharomycopsis crataegensis (S. crataegensis)*. Suitable strains of *K. marxianus* and *C. sonorensis* include those described in WO 00/71738 AI, WO 02/42471 A2, WO 03/049525 A2, WO 03/102152 A2 and WO 03/102201A2. Suitable strains of *I. orientalis* are ATCC strain 32196 and ATCC strain PTA-6648. In the invention, the host cell may be a Crabtree negative as a wild-type strain. The Crabtree effect is defined as the occurrence of fermentative metabolism under aerobic conditions due to the inhibition of oxygen consumption by a microorganism when cultured at high specific growth rates (long-term effect) or in the presence of high concentrations of glucose (short-term effect). Crabtree negative phenotypes do not exhibit this effect, and are thus able to consume oxygen even in the presence of high concentrations of glucose or at high growth rates.

The eukaryotic cell may be a filamentous fungal cell. Filamentous fungi include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocaffimastix, Neurospora, Paecilomyces, Penicillium, Piromyces, Phanerochaete Podospora, Pycnoporus, Rhizopus, Schizophyllum, Sordaria, Talaromyces, Rasamsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii), Aspergillus sojae, Chrysosporium lucknowense, Myceliophtora thermophyla*. Reference host cells for the comparison of fermentation characteristics of transformed and untransformed cells, include e.g.

*Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Thielavia terrestris* NRRL8126, *Talaromyces emersonii* CBS 124.902, *Rasamsonia emersonii* CBS393.64, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains.

A more preferred host cell belongs to the genus *Aspergillus*, more preferably the host cell belongs to the species *Aspergillus niger*. When the host cell according to the invention is an *Aspergillus niger* host cell, the host cell preferably is CBS 513.88, CBS124.903 or a derivative thereof.

In a preferred embodiment, a host cell according to the invention is a yeast cell selected from the group consisting of *Candida, Hansenula, Issatchenkia, Kluyveromyces, Pichia, Saccharomyces, Schizosaccharomyces*, or *Yarrowia* strains, or a filamentous fungal cell selected from the group consisting of filamentous fungal cells belong to a species of *Acremonium, Aspergillus, Chrysosporium, Myceliophthora, Penicillium, Talaromyces, Rasamsonia, Thielavia, Fusarium* or *Trichoderma*.

A host cell of the invention may be any wild type strain producing a dicarboxylic acid. Furthermore, a suitable host cell may be a cell which has been obtained and/or improved by subjecting a parental or wild type cell of interest to a classical mutagenic treatment or to recombinant nucleic acid transformation. Thus, a suitable host cell may already be capable of producing the dicarboxylic acid. However, the cell may also be provided with a homologous or heterologous expression construct that encodes one or more polypeptides involved in the production of the dicarboxylic acid.

Accordingly, in some embodiments, a recombinant host cell of the invention may comprise a MDH mutant polypeptide and an active reductive tricarboxylic acid (TCA) pathway from phosphoenolpyruvate or pyruvate to succinate.

Accordingly, in addition to a nucleic acid encoding a MDH mutant polypeptide, a host cell of the invention may comprise a nucleotide sequence comprising sequence encoding one or more of a pyruvate carboxylase, a phosphoenolpyruvate carboxykinase, a phosphoenolpyruvate carboxylase, a malate dehydrogenase, a fumarase, an isocitrate lyase, a malate synthase, a fumarate reductase and/or a dicarboxylic acid transporter. Preferably, one or more such enzymes are (over)expressed and active in the cytosol.

Thus, a recombinant host cell of the invention may overexpress a suitable homologous or heterologous nucleotide sequence that encodes a endogenous and/or heterologous enzyme that catalyzes a reaction in the cell resulting in an increased flux towards a dicarboxylic acid such malic acid, fumaric acid and/or succinic acid.

A recombinant host cell of the invention may overexpress an endogenous or heterologous nucleic acid sequence as described herein below.

A recombinant host cell of the invention may comprise a genetic modification with a pyruvate carboxylase (PYC), that catalyses the reaction from pyruvate to oxaloacetate (EC 6.4.1.1). The pyruvate carboxylase may for instance be active in the cytosol upon expression of the gene. For instance, the host cell overexpresses a pyruvate carboxylase, for instance an endogenous or homologous pyruvate carboxylase is overexpressed. The recombinant fungal host cell according to the present invention may be genetically modified with a pyruvate carboxylase which has at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 46.

Preferably, the recombinant host cell expresses a nucleotide sequence encoding a phosphoenolpyruvate (PEP) carboxykinase in the cytosol. Preferably a nucleotide sequence encoding a PEP carboxykinase is overexpressed. The PEP carboxykinase (EC 4.1.1.49) preferably is a heterologous enzyme, preferably derived from bacteria, more preferably the enzyme having PEP carboxykinase activity is derived from *Escherichia coil, Mannheimia* sp., *Actinobacillus* sp., or *Anaerobiospirillum* sp., more preferably *Mannheimia succiniciproducens*. A gene encoding a PEP carboxykinase may be overexpressed and active in the cytosol of a fungal cell. Preferably, a recombinant fungal cell according to the present invention is genetically modified with a PEP carboxykinase which has at at least 70%, preferably at least 75%, 80%, 85%, 90%, 91%, 92%, 93%, 94%, 95%, 96%, 97%, 98%, 99% or 100% sequence identity with amino acid sequence of SEQ ID NO: 47.

Preferably, the recombinant host cell expresses a nucleotide sequence encoding a phosphoenolpyruvate (PEP) carboxylase in the cytosol. Preferably a nucleotide sequence encoding a PEP carboxylase is overexpressed. The PEP carboxylase (EC 4.1.1.31) preferably is a heterologous enzyme, preferably derived from bacteria.

In one embodiment, the recombinant host cell is further genetically modified with a gene encoding a malate dehydrogenase (MDH) active in the cytosol upon expression of the gene. Cytosolic expression may be obtained by deletion of a peroxisomal targeting signal. The malate dehydrogenase may be overexpressed. A cytosolic MDH may be any suitable homologous or heterologous malate dehydrogenase, catalyzing the reaction from oxaloacetate to malate (EC 1.1.1.37), for instance derived from *S. cerevisiae*.

Preferably, the MDH is *S. cerevisiae* MDH3, more preferably one which has a C-terminal SKL deletion such that it is active in the cytosol. Preferably, the recombinant fungal cell according to the present invention comprises a nucleotide sequence encoding a malate dehydrogenase that has at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 39.

In another embodiment, the recombinant host cell of the present disclosure is further genetically modified with a gene encoding a fumarase, that catalyses the reaction from malic acid to fumaric acid (EC 4.2.1.2). A gene encoding fumarase may be derived from any suitable origin, preferably from microbial origin, for instance a yeast such as *Saccharomyces* or a filamentous fungus, such *Rhizopus oryzae*, or a bacterium such a *Escherichia coli*. The host cell of the present disclosure may overexpress a nucleotide sequence encoding a fumarase. The fumarase may be active in the cytosol upon expression of the nucleotide sequence, for instance by deleting a peroxisomal targeting signal. It was found that cytosolic activity of a fumarase resulted in a high productivity of a dicarboxylic acid by a fungal cell.

Preferably, the recombinant host cell of the present invention overexpresses a nucleotide sequence encoding a fumarase that has at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 48, SEQ ID NO: 49 or SEQ ID NO: 67.

In another embodiment, the recombinant host cell is genetically modified with any suitable heterologous or homologous gene encoding a NAD(H)-dependent fumarate reductase, catalyzing the reaction from fumarate to succinate (EC 1.3.1.6). The NAD(H)-dependent fumarate reductase may be a heterologous enzyme, which may be derived from any suitable origin, for instance bacteria, fungi, protozoa or plants. A fungal cell of the present disclosure comprises a heterologous NAD(H)-dependent fumarate reductase, preferably derived from a *Trypanosoma* sp, for instance a *Trypanosoma brucei*. In one embodiment, the NAD(H)-dependent fumarate reductase is expressed and active in the cytosol, for instance by deleting a peroxisomal targeting signal. The host cell may overexpress a gene encoding a NAD(H)-dependent fumarate reductase.

Preferably, the recombinant host cell according to the present invention is genetically modified with a NAD(H)-dependent fumarate reductase, which has at least at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 8. Also preferably, the host cell according to the present invention is genetically modified with a variant polypeptide having fumarate reductase activity as disclosed in WO2015/086839.

In another embodiment, the recombinant host cell of the invention expresses a nucleotide sequence encoding a dicarboxylic acid transporter protein. Preferably the dicarboxylic acid transporter protein is overexpressed. A dicarboxylic acid transporter protein may be any suitable homologous or heterologous protein. Preferably the dicarboxylic acid transporter protein is a heterologous protein. A dicarboxylic acid transporter protein may be derived from any suitable organism, preferably from yeast or fungi such as *Schizosaccharomyces pombe* or *Aspergillus niger*. Preferably, a dicarboxylic acid transporter protein is a dicarboxylic acid transporter/malic acid transporter protein, eg. from *Aspergillus niger* which at least 70%, preferably at least 75%, 80%, 85%, 90%, 91%, 92%, 93%, 94%, 95%, 96%, 97%, 90%, 91%, 92%, 93%, 94%, 95%, 96%, 97%, 98%, 99% or 100% sequence identity with the amino acid sequence of SEQ ID NO: 50.

The recombinant host cell may further comprise a genetic modification with a gene encoding an isocitrate lyase (EC 4.1.3.1), which may be any suitable heterologous or homologous enzyme. The isocitrate lyase may for instance be obtained from *Kluyveromyces lactis* or *Escherichia coli*.

The recombinant host according to the present invention is genetically modified with a isocitrate lyase which has at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 51.

The recombinant host cell may further comprise a genetic modification with a malate synthase (EC 2.3.3.9). The malate synthase may be overexpressed and/or active in the cytosol, for instance by deletion of a peroxisomal targeting signal. In the event the malate synthase is a *S. cerevisiae* malate synthase, for instance the native malate synthase is altered by the deletion of the SKL carboxy-terminal sequence.

The recombinant host cell of the present invention is genetically modified with a malate synthase which at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 52.

In another embodiment, the recombinant host cell of the invention disclosed herein comprises a disruption of a gene a pyruvate decarboxylase (EC 4.1.1.1), catalyzing the reaction from pyruvate to acetaldehyde.

In another embodiment, the recombinant host cell of the invention may comprise a disruption of a gene encoding an enzyme of the ethanol fermentation pathway. A gene encoding an enzyme of an ethanol fermentation pathway, may be pyruvate decarboxylase (EC 4.1.1.1), catalyzing the reaction from pyruvate to acetaldehyde, or alcohol dehydrogenase (EC 1.1.1.1), catalyzing the reaction from acetaldehyde to ethanol. Preferably, a host cell of the invention comprises a disruption of one, two or more genes encoding an alcohol dehydrogenase. In the event the fungal cell is a yeast, e.g. *S. cerevisiae*, the yeast preferably comprises a disruption of one or more alcohol dehydrogenase genes (adh1 adh2, adh3, adh4, adh5, adh6).

Alternatively or in addition, the recombinant host cell of the invention may comprise at least one gene encoding glycerol-3-phosphate dehydrogenase which is not functional. A glycerol-3-phosphate dehydrogenase gene that is not functional is used herein to describe a eukaryotic cell, which comprises a reduced glycerol-3-phosphate dehydrogenase activity, for instance by mutation, disruption, or deletion of the gene encoding glycerol-3-phosphate dehydrogenase, resulting in a decreased formation of glycerol as compared to a wild-type cell. In the event the fungal cell is a yeast, e.g. *S. cerevisiae*, the yeast preferably comprises a disruption of one or more glycerol-3-phosphate dehydrogenase genes (gpd1, gpd2, gut2).

Alternatively or in addition to the above, the recombinant host cell of the invention may comprise at least one gene encoding a mitochondrial external NADH dehydrogenase which is not functional. A mitochondrial external NADH dehydrogenase gene that is not functional is used herein to describe a eukaryotic cell, which comprises a reduced NADH dehydrogenase activity, for instance by mutation, disruption, or deletion of the gene encoding the mitochondrial external NADH dehydrogenase. In the event the fungal cell is a yeast, e.g. *S. cerevisiae*, the yeast preferably comprises a disruption of one or more mitochondrial external NADH dehydrogenase genes (nde1, nde2).

Alternatively or in addition to the above, the recombinant host cell of the invention may comprise at least one gene encoding an aldehyde dehydrogenase which is not functional. An aldehyde dehydrogenase gene that is not functional is used herein to describe a eukaryotic cell, which comprises a reduced aldehyde dehydrogenase activity, for instance by mutation, disruption, or deletion of the gene encoding the aldehyde dehydrogenase. In the event the fungal cell is a yeast, e.g. *S. cerevisiae*, the yeast preferably comprises a disruption of one or more aldehyde dehydrogenase genes (ald2, ald3, ald4, ald5, ald6).

Preferably, the recombinant host cell of the present invention is a recombinant fungal cell. More preferably, the host cell of the present invention is a recombinant yeast cell. Preferred embodiments of the recombinant fungal cell or recombinant yeast cell are as described herein above for the recombinant host cell.

In some embodiments of the invention, the recombinant host cell is a recombinant yeast cell which is capable of producing a dicarboxylic acid as described herein above and which comprises a nucleic acid sequence encoding a mutant polypeptide having malate dehydrogenase activity as detailed herein above. Said MDH mutant may be a mutant of a homologous or heterologous wild-type MDH polypeptide. In a preferred embodiment, said MDH mutant is a mutant of a homologous MDH polypeptide. In an even more preferred embodiment, the recombinant yeast cell is a recombinant *Saccharomyces*, for example *S. cerevisiae*, and the MDH mutant is a mutant of a homologous MDH, for example MDH2 or MDH3. In a more specific embodiment, said recombinant yeast cell comprises a nucleic sequence encoding a mutant polypeptide having malate dehydrogenase activity as defined in Table 1 and wherein the amino acid residue corresponding to amino acid 34 in SEQ ID NO: 39 is selected from glycine (G) or serine (S).

Standard genetic techniques, such as overexpression of enzymes in the host cells, genetic modification of host cells, or hybridisation techniques, are known methods in the art, such as described in Sambrook et al. (Molecular Cloning: A Laboratory Manual, 3$^{rd}$ edition, *Cold Spring Harbor Laboratory Press*, Cold Spring Harbor Laboratory, NY, 2001) or Ausubel et al. (Current protocols in molecular biology, *Green Publishing and Wiley Interscience*, NY, 1987). Methods for transformation, genetic modification of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

As used herein, the terms "nucleic acid", "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "nucleic acid construct" is herein referred to as a nucleic acid molecule, either single- or double-stranded, which is isolated from a naturally-occurring gene or, more typically, which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence in a host cell, wherein said control sequences are operably linked to said coding sequence.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve the expression of a nucleotide sequence coding for an enzyme such a malate dehydrogenase or any other enzyme introduced in the host cell of the invention, may be not native to a nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in this context include both constitutive and inducible natural promoters as well as engineered promoters, which are well known to the person skilled in the art. Suitable promoters in eukaryotic host cells may be GAL7, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleotide sequence encoding an enzyme comprises a "terminator". Any terminator, which is functional in the eukaryotic cell, may be used in the present invention. Preferred terminators are obtained from natural genes of the host cell. Suitable terminator sequences are well known in the art. Preferably, such terminators are combined with mutations that prevent nonsense mediated mRNA decay in the host cell of the invention (see for example: Shirley et al., 2002, *Genetics* 161:1465-1482).

The nucleic acid construct may be incorporated into a "vector", such as an expression vector and/or into a host cell in order to effect expression of the polypeptide to be expressed.

The expression vector may be any vector (e.g., a plasmid or virus), which can be conveniently subjected to recombinant DNA procedures and can bring about the expression of the polynucleotide encoding the polypeptide having malate dehydrogenase activity. The choice of the vector will typically depend on the compatibility of the vector with the host cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. If intended for use in a host cell of fungal origin, a suitable episomal nucleic acid construct may e.g. be based on the yeast 2μ or pKD1 plasmids (Gleer et al., 1991, *Biotechnology* 9: 968-975), or the AMA plasmids (Fierro et al., 1995, *Curr Genet.* 29:482-489).

Alternatively, the expression vector may be one which, when introduced into the host cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 20 bp, at least 30 bp, at least 50 bp, at least 0.1 kb, at least 0.2 kb, at least 0.5 kb, at least 1 kb, at least 2 kb or longer. The efficiency of targeted integration into the genome of the host cell, i.e. integration in a predetermined target locus, is increased by augmented homologous recombination abilities of the host cell.

The homologous flanking DNA sequences in the cloning vector, which are homologous to the target locus, are derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l.

A nucleic acid construct or expression vector may be assembled in vivo in a host cell of the invention and, optionally, integrated into the genome of the cell in a single step (see, for example, WO2013/076280)

More than one copy of a nucleic acid construct or expression vector of the invention may be inserted into the host cell to increase production of the polypeptide having malate dehydrogenase activity (over-expression) encoded by the nucleic acid sequence comprised within the nucleic acid construct. This can be done, preferably by integrating into its genome two or more copies of the nucleic acid, more preferably by targeting the integration of the nucleic acid at a highly expressed locus defined as defined above.

It will be appreciated by those skilled in the art that the design of the expression vector can depend on such factors as the choice of the host cell to be transformed, the level of expression of protein desired, etc.

A nucleic acid construct and/or expression vector of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell well known to those skilled in the art. Suitable methods for transforming or transfecting host cells can be found in Sambrook et al. (Molecular Cloning: A Laboratory Manual, 3rd edition, *Cold Spring Harbor Laboratory Press*, Cold Spring Harbor Laboratory, NY, 2001), Davis et al. (Basic Methods in Molecular Biology, 1st edition, *Elsevier*, 1986) and other laboratory manuals.

Cytosolic expression of the enzymes described above may be obtained by deletion of a peroxisomal or mitochondrial targeting signal. The presence of a peroxisomal or mitochondrial targeting signal may for instance be determined by the method disclosed by Schlüter et al. (Schlüter et al., 2007, *Nucleic Acid Research* 35: D815-D822).

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) *J. Mol. Biol.* 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. *Trends in Genetics* 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the blastn and blastx programs (version 2.2.31 or above) of Altschul, et al. (1990) *J. Mol. Biol.* 215:403-10. BLAST nucleotide searches can be performed with the blastn program, score=100, word-size=11 to obtain nucleotide sequences homologous to nucleic acid molecules of the invention. BLAST protein searches can be performed with the blastx program, score=50, word-size=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., blastx and blastn) can be used. See the homepage of the National Center for Biotechnology Information at http://www.ncbi.nlm.nih.gov/.

According to the present invention, there is also provided a process for the production of a dicarboxylic acid, such as succinic acid, which process comprises fermenting the recombinant host cell of the invention as described herein above, under conditions suitable for production of the dicarboxylic acid, and optionally, recovering the dicarboxylic acid from the fermentation medium.

In the process, the recombinant host cell of the invention is fermented in a vessel comprising a suitable fermentation medium. The term fermenting, fermentation or fermented and the like as used herein refers to the microbial production of compounds, here dicarboxylic acids from carbohydrates.

Preferably, the fermentation product is a dicarboxylic acid, preferably malic acid, fumaric acid and/or succinic acid, preferably succinic acid.

A batch fermentation is defined herein as a fermentation wherein all nutrients are added at the start of a fermentation.

A fed-batch fermentation is a batch fermentation wherein the nutrients are added during the fermentation. Products in a batch and fed-batch fermentation may be harvested at a suitable moment, for instance when one or more nutrients are exhausted.

A continuous fermentation is a fermentation wherein nutrients are continuously added to the fermentation and wherein products are continuously removed from the fermentation.

In one embodiment fermenting the host cell in the process of the invention is carried out under carbohydrate limiting conditions. As used herein, carbohydrate limiting conditions are defined as maintaining the carbohydrate concentration below 10 g/l, for example about 5 g/l.

The process for the production of dicarboxylic acid according to the present invention may be carried out in any suitable volume and scale, preferably on an industrial scale. Industrial scale is defined herein as a volume of at least 10, or 100 litres, preferably at least 1 cubic metre, preferably at least 10, or 100 cubic metres, preferably at least 1000 cubic metres, usually below 10,000 cubic metres.

Fermenting the recombinant host cell in the process of the invention may be carried out in any suitable fermentation medium comprising a suitable nitrogen source, carbohydrate and other nutrients required for growth and production of a dicarboxylic acid in the process of the invention. A suitable carbohydrate in the fermentation process according to the invention may be glucose, galactose, xylose, arabinose, sucrose, or maltose.

In one embodiment, the fermentation process is carried out under a partial $CO_2$ pressure of between 5% and 60%, preferably about 50%.

The pH during the process for the production of dicarboxylic acid usually lowers during the production of the dicarboxylic acid. Preferably, the pH in the process for the production of dicarboxylic acid ranges between 1 and 5, preferably between 1.5 and 4.5, more preferably between 2 and 4.

In another preferred embodiment, the process according to the present invention comprises a step of preculturing the host cell under aerobic conditions in the presence of a carbohydrate. Preferably, the fermentation of the host cell during preculturing is carried out at a pH of between 4 and 6. Preferably, the carbohydrate during preculturing is a non-repressing carbohydrate, preferably galactose. It has been found advantageous to preculture host cells on a non-repressing carbohydrate, since this prevents glucose repression occurring, which may negatively influence the amount of biomass produced. In addition, it has been found that a step of preculturing host cells under aerobic conditions results in a higher biomass yield and a faster growth. Preferably, the preculturing is carried out in batch mode.

A propagation step for producing increased biomass is typically carried out, preferably under carbohydrate limiting conditions.

The process for producing a dicarboxylic acid may be carried out at any suitable temperature. A suitable temperature may for instance be between about 10 and about 40 degrees Celsius, for instance between about 15 and about 30 degrees Celsius.

In an embodiment, the process of the invention is carried out in such a way that at least a portion of the host cells is reused, i.e. recycled. The cells may be recycled back into the original vessel or into a second vessel. Preferably, the medium into which the recycled host cells are introduced is supplemented with a vitamin and/or a trace element.

In a preferred embodiment, the fermentation medium comprises an amount of succinic acid of between 1 and 150 g/l, preferably between 5 and 100 g/l, more preferably between 10 and 80 g/l or between 15 and 60 g/l of succinic acid. In any event, the recombinant host cell of the invention will typically be capable of accumulating more succinic acid in the fermentation medium as compared to a host cell that has been modified with a reference MDH polypeptide, for example that of SEQ ID NO: 39.

The process for the production of a dicarboxylic acid may further comprise recovering the dicarboxylic acid. Recovery of the dicarboxylic acid may be carried out by any suitable method known in the art, for instance by crystallization, ammonium precipitation, ion exchange technology, centrifugation or filtration or any suitable combination of these methods.

In a preferred embodiment, the recovery of the dicarboxylic acid comprises crystallizing the dicarboxylic acid and forming dicarboxylic acid crystals. Preferably, the crystallizing of the dicarboxylic acid comprises removing part of the fermentation medium, preferably by evaporation, to obtain a concentrated medium.

According to the present invention, the dicarboxylic acid, such as succinic acid may be recovered by crystallizing the dicarboxylic acid, such as succinic acid, from an aqueous solution having a pH of between 1 and 5 and comprising succinic acid, comprising evaporating part of the aqueous solution to obtain a concentrated solution, lowering the temperature of the concentrated solution to a value of between 5 and 35 degrees Celsius, wherein succinic acid crystals are formed. Preferably, the crystallizing comprises bringing the temperature of the concentrated medium to a temperature of between 10 and 30 degrees Celsius, preferably between 15 and 25 degrees Celsius. Preferably, the fermentation medium has a pH of between 1.5 and 4.5, preferably between 2 and 4.

It has been found that crystallizing the dicarboxylic acid, such as succinic acid, at higher temperatures such as between 10 and 30 degrees Celsius results in crystals of a dicarboxylic acid, such as succinic acid, with a lower amount of impurities such as organic acid, protein, color and/or odor, than crystals of a dicarboxylic acid, such as succinic acid, that were crystallized at a low temperature of below 10 degrees.

Another advantage of crystallizing succinic acid at a higher temperature is that it requires a lower amount of energy for cooling the aqueous solution as compared to a process wherein crystallizing the dicarboxylic acid is carried out below 10 or 5 degrees Celsius, resulting in a more economical and sustainable process.

Preferably, the crystallizing of the dicarboxylic acid, such as succinic acid, comprises a step of washing the dicarboxylic acid crystals. Dicarboxylic acid, such as succinic acid, may be crystallized directly from the fermentation medium having a pH of between 1 and 5 to a purity of at least 90% w/w, preferably at least 95, 96, 97, or at least 98%, or 99 to 100% w/w.

In a preferred embodiment, the process for the production of a dicarboxylic acid further comprises using the dicarboxylic acid in an industrial process.

Preferably, the dicarboxylic acid, such as succinic acid, that is prepared in the process according to the present invention is further converted into a desirable product. A desirable product may for instance be a polymer, such as polybutylene succinic acid (PBS), a deicing agent, a food additive, a cosmetic additive or a surfactant. That is to say, the invention provides a method for the production of a product, for example, a polymer, such as polybutylene succinic acid (PBS), a deicing agent, a food additive, a cosmetic additive or a surfactant, which method comprises: producing a dicarboxylic acid as described herein; and using said dicarboxylic acid in the production of said product.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General Materials and Methods

DNA Procedures

Standard DNA procedures were carried out as described elsewhere (Sambrook et al., 1989, *Molecular cloning: a laboratory manual*, $2^{nd}$ Ed., Cold Spring Harbor Laboratory Press, Cold Spring Harbor, N.Y.) unless otherwise stated. DNA was amplified using the proofreading enzyme Phusion polymerase (New England Biolabs, USA) according to manufacturer's instructions. Restriction enzymes were from Invitrogen or New England Biolabs.

Microtiter Plate (MTP) Fermentation of Dicarboxylic Acid Production Strains

To determine dicarboxylic acid production, strains were grown in triplicate in micro titer plates in humidity shakers (Infors) for 3 days at 30 degrees at 550 rpm and 80% humidity. The medium was based on Verduyn medium (Verduyn C, Postma E, Scheffers W A, Van Dijken J P. Yeast, 1992 July; 8(7):501-517), but modifications in carbon and nitrogen source were made as described herein below.

| MTP pre-culture medium composition | | |
|---|---|---|
| Raw material | | Concentration (g/l) |
| Galactose | $C_6H_{12}O_6 \cdot H_2O$ | 40.0 |
| Urea | $(NH_2)_2CO$ | 2.3 |
| Potassium dihydrogen phosphate | $KH_2PO_4$ | 3.0 |
| Magnesium sulphate | $MgSO_4 \cdot 7H_2O$ | 0.5 |
| Trace element solution[a] | | 1 |
| Vitamin solution[b] | | 1 |
| Component | Formula | Concentration (g/kg) |
| [a]Trace elements solution | | |
| EDTA | $C_{10}H_{14}N_2Na_2O_8 \cdot 2H_2O$ | 15.00 |
| Zincsulphate·7H₂O | $ZnSO_4 \cdot 7H_2O$ | 4.50 |
| Manganesechloride·2H₂O | $MnCl_2 \cdot 2H_2O$ | 0.84 |
| Cobalt (II) chloride·6H₂O | $CoCl_2 \cdot 6H_2O$ | 0.30 |
| Copper (II) sulphate·5H₂O | $CuSO_4 \cdot 5H_2O$ | 0.30 |
| Sodium molybdenum·2H₂O | $Na_2MoO_4 \cdot 2H_2O$ | 0.40 |
| Calciumchloride·2H₂O | $CaCl_2 \cdot 2H_2O$ | 4.50 |
| Ironsulphate·7H₂O | $FeSO_4 \cdot 7H_2O$ | 3.00 |
| Boric acid | $H_3BO_3$ | 1.00 |
| Potassium iodide | $KI$ | 0.10 |
| [b]Vitamin solution | | |
| Biotin (D−) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

80 microliters of pre-culture was used to inoculate 2.5 ml of medium with 1.5% galactose as carbon source in 24-well plates. The cultures were grown for 72 hours in humidity shakers (Infors) at 30° C., 550 rpm, 80% humidity. After generating biomass, a production experiment was started by re-suspending cells into 2.5 ml of mineral medium with glucose as carbon source. The main cultures were incubated in humidity shakers (Infors) at 30 degrees at 550 rpm and 80% humidity and samples were taken after 48 hours of cultivation.

Metabolite Analysis of MTP Samples by NMR

For metabolite analysis of MTP samples, 90 microliter of supernatant of fermentation samples is mixed with 10 microliter of NMR standard (20 g/l maleic acid) and 100 microliter of 10% $D_2O$ solution. The samples are lyophilized and subsequently dissolved in 1 mL $D_2O$.

1D 1H NMR spectra are recorded on a BEST Bruker Avance III spectrometer, operating at a proton frequency of 500 MHz, equipped with a He-cooled cryo probe, using a pulse program without water suppression (ZG) at a temperature of 300 K, with a 90 degree excitation pulse, acquisition time of 2.0 seconds and a relaxation delay of 40 seconds. The number of scans was set at 8.

The malic acid concentration [in g/l] is calculated based on the following signals ($\delta$ relative to 4,4-dimethyl-4-silapentane-1-sulfonic acid):

Malic acid: Depending on the pH and overlap of the $\alpha$-CH2 and the CH(OH) signals with other compounds, one of the three malic acid signals is chosen for quantification, $\alpha$-CH (A) (2.92 ppm, n=1H, double doublet or dd), $\alpha$-CH(X) (2.85 ppm, n=1H, dd) or CH(OH) (4.6 ppm, n=1H, dd).

The succinic acid concentration [in g/L] is calculated based on the following signals ($\delta$ relative to 4,4-dimethyl-4-silapentane-1-sulfonic acid):

Succinic acid: succinic acid signal at 2.67 ppm (s, 4 H)

The signal used for the standard: maleic acid peak around 6.3 ppm (S, 2 H).

Quantification by NMR is described by Bharti et al., 2012, TrAC Trends in Analytical Chemistry 35:5-26.

Example 1: Construction of Strain SUC-1029

Strain CEN.PK 113-7D (MATa HIS3 LEU2 TRP1 MAL2-8 SUC2) was used as a starting point to construct strain SUC-1029. A fumarase gene of *Rhyzopus oryzae* (FUMR) was transformed to strain CEN.PK113-7D as described below.

Generation of PCR Fragments

PCR fragment 9 was obtained by PCR amplification of SEQ ID NO: 34 using primers amplifying the entire nucleotide sequence of SEQ ID NO: 34. SEQ ID NO: 34 describes a synthetic polynucleotide containing the fumarase (FUMR) nucleotide sequence from *Rhyzopus oryzae* as disclosed in patent application WO2009/065779. The gene sequence was codon pair optimized for expression in *S. cerevisiae* as disclosed in patent application WO2008/000632. Expression of the FUMR gene is controlled by the TDH1 promoter (600 bp directly before the start codon of the TDH1 gene)

and the TDH1 terminator (300 bp directly after the stop codon of the TDH1 gene). The TDH1 promoter and TDH1 terminator sequences controlling expression of FUMR are native sequences derived from *Saccharomyces cerevisiae* S288C. The 599 bp region at the 5' end of SEQ ID NO: 34, upstream of the TDH1 promoter, is a region homologous to the YPRCtau3 locus.

PCR fragment 10 was obtained by PCR amplification of SEQ ID NO: 35 using primers amplifying the entire nucleotide sequence of SEQ ID NO: 35. SEQ ID NO: 35 describes a synthetic polynucleotide containing part of the pSUC227 plasmid sequence, described in PCT/EP2013/055047 The 5' end of SEQ ID NO: 35 contains overlap with the 3' end of SEQ ID NO: 34. The 3' end of SEQ ID NO: 35 contains overlap with the 5' end of SEQ ID NO: 36.

PCR fragment 11 was obtained by PCR amplification of SEQ ID NO: 36 using primers amplifying the entire nucleotide sequence of SEQ ID NO: 36. SEQ ID NO: 36 describes a synthetic polynucleotide containing part of the pSUC225 plasmid sequence, described in PCT/EP2013/055047. The 3' end of SEQ ID NO: 36 contains overlap with the 5' end of SEQ ID NO: 37.

PCR fragment 12 was obtained by PCR amplification of SEQ ID NO: 37 using primers amplifying the entire nucleotide sequence of SEQ ID NO: 37. SEQ ID NO: 37 describes a synthetic polynucleotide homologous to the YPRCtau3 locus.

PCR fragments 9 to 12 were purified using the DNA Clean & Concentrator™-25 kit (Zymo Research, Irvine, Calif., USA) according to manufacturer's instructions.
Transformation to CEN.PK113-7D in Order to Construct Strain SUC-1029

Yeast transformation was done by a method known by persons skilled in the art. *S. cerevisiae* strain CEN.PK113-7D was transformed with purified PCR fragments 9 to 12 PCR fragments 10 and 11 contained overlaps at their 5' and 3' ends and PCR fragments 9 and 12 at their 3' and 5' end respectively, such that this allowed homologous recombination of all four PCR fragments (FIG. 1). The 5' end of PCR fragment 9 and the 3' end of PCR fragment 12 were homologous to the YPRCtau3 locus and enabled integration of all four PCR fragments in the YPRCtau3 locus (FIG. 1). This resulted in one linear fragment consisting of PCR fragments 9 to 12 integrated in the YPRCtau3 locus, which is located on chromosome XVI.

Transformation mixtures were plated on YEPhD-agar (per liter: 10 grams yeast extract, 20 grams PhytonePeptone, 20 grams glucose, 20 grams agar) containing 200 µg G418 (Sigma Aldrich, Zwijndrecht, The Netherlands) per ml. After three days of growth at 30° C., individual transformants were re-streaked on YEPh—agar plates containing 20 grams glucose per liter and 200 µg G418 per ml.

Subsequently, the marker cassette and Cre-recombinase gene present on the integrated PCR fragments 10 and 11 were removed by recombination between the lox66 and lox71 sites that flank the KanMX marker and the CRE gene encoding the CRE recombinase by CRE recombinase, using the method described in PCT/EP2013/055047, resulting in removal of the KanMX marker and the CRE gene and leaving a lox72 site as a result of recombination between the lox66 and lox71 sites. The resulting markerfree strain was named SUC-1029.

Presence of the introduced FUMR gene was confirmed by using PCR using primer sequences that can anneal to the coding sequences of the ORF's encoded by SEQ ID NO: 34. Correct integration and removal of the KanMX marker was confirmed by PCR using primers 5' and 3' from the YPRCtau3 locus, not hybridizing on the YPRCtau3 homologous regions present on PCR fragments 9 and 12.

Example 2: Construction of Strain SUC-1112

Generation of PCR Fragments
Primer sequences described in SEQ ID NO: 9 and SEQ ID NO: 10 were used to generate PCR fragment 1 consisting of the 5' INT59 integration site, using genomic DNA of strain *Saccharomyces cerevisiae* strain CEN.PK 113-7D (MATa HIS3 LEU2 TRP1 MAL2-8 SUC2) as template.

PCR fragment 2 was generated by using the primer sequences described in SEQ ID NO: 11 and SEQ ID NO: 12, using SEQ ID NO: 1 as template. SEQ ID NO: 1 encodes phosphoenolpyruvate carboxykinase (PCKa) from *Actinobacillus succinogenes*, as disclosed in patent application WO2009/065780. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the TPI1-promoter controls the expression of the PCKa-gene. Proper termination is controlled by a terminator sequence from *S. cerevisiae*, i.e. the GND2-terminator.

PCR fragment 3 was generated by using the primer sequences described in SEQ ID NO: 13 and SEQ ID NO: 14, using SEQ ID NO: 2 as template. SEQ ID NO: 2 encodes pyruvate carboxylase (PYC2) from *Saccharomyces cerevisiae*, as disclosed in patent application WO2009/065780. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the PGK1-promoter controls the expression of the PYC2-gene. Proper termination is controlled by a terminator sequence from *S. cerevisiae*, i.e. the ADH1-terminator.

PCR fragment 4 was generated by using the primer sequences described in SEQ ID NO: 15 and SEQ ID NO: 16, using SEQ ID NO: 3 as template. SEQ ID NO: 3 encodes a KanMX selection marker functional in *Saccharomyces cerevisiae* which was amplified from plasmid pUG7-EcoRV. pUG7-EcoRV is a variant of plasmid pUG6 described by Gueldener et al., (Nucleic Acids Res. 1996 Jul. 1; 24(13): 2519-24), in which the loxP sites present in pUG6 were changed into lox66 and lox71 sites (Lambert et al., Appl. Environ. Microbiol. 2007 February; 73(4):1126-35. Epub 2006 Dec. 1.)

PCR fragment 5 was generated by using the primer sequences described in SEQ ID NO: 17 and SEQ ID NO: 18, using SEQ ID NO: 4 as template. SEQ ID NO: 4 encodes a putative dicarboxylic acid transporter from *Aspergillus niger*, as disclosed in EP2495304. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the ENO1-promoter controls the expression of the DCT_02-gene. Proper termination is controlled by a terminator sequence from *S. cerevisiae*, i.e. the TEF2-terminator.

PCR fragment 6 was generated by using the primer sequences described in SEQ ID NO: 19 and SEQ ID NO: 20, using SEQ ID NO: 5 as template. SEQ ID NO: 5 encodes malate dehydrogenase (MDH3) from *Saccharomyces cerevisiae*, as disclosed in patent application WO2009/065778. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *Kluyveromyces lactis*, i.e. the promoter of ORF KLLA0_F20031g (uniprot accession number Q6CJA9) controls the expression of the MDH3-gene. Proper termination is controlled by a terminator sequence from *S. cerevisiae*, i.e. the GPM1-terminator.

PCR fragment 7 was generated by using the primer sequences described in SEQ ID NO: 21 and SEQ ID NO: 22, using SEQ ID NO: 6 as template. SEQ ID NO: 6 encodes fumarase (fumB) from *Escherichia coli* (E.C. 4.2.1.2, UniProt accession number P14407). The gene sequence was codon pair optimized for expression in *S. cerevisiae* as disclosed in patent application WO2008/000632. The synthetic sequence, which includes promoter-gene-terminator sequence, including appropriate restriction sites, was synthesized by DNA 2.0 (Menlo Park, Calif., USA). The synthetic gene is under control of (or operable linked to) a promoter from *S. cerevisiae*, i.e. the TDH3-promoter controls the expression of the controls the expression of the fumB-gene. Proper termination is controlled by a terminator sequence from *S. cerevisiae*, i.e. the TDH1-terminator.

PCR fragment 8 was generated by using the primer sequences described in SEQ ID NO: 23 and SEQ ID NO: 24, using SEQ ID NO: 7 as template. SEQ ID NO: 7 encodes encodes fumarate reductase (FRDg) from *Trypanosoma brucei*, as disclosed in patent application WO2009/065778. The gene sequence was codon pair optimized for expression in *S. cerevisiae* as disclosed in patent application WO2008/000632. The synthetic sequence, which includes promoter-gene-terminator sequence, including appropriate restriction sites, was synthesized by DNA 2.0 (Menlo Park, Calif., USA). The synthetic gene is under control of (or operable linked to) a promoter from *S. cerevisiae*, i.e. the TEF1-promoter controls the expression of the controls the expression of the fumB-gene. Proper termination is controlled by a terminator sequence from *S. cerevisiae*, i.e. the TAD1-terminator.

Primer sequences described in SEQ ID NO: 40 and SEQ ID NO: 41 were used to generate PCR fragment 113 consisting of the 3' INT59 integration site, using genomic DNA of strain CEN.PK 113-7D as template.

PCR fragments 1 to 8 and PCR fragment 113 were purified using the DNA Clean & Concentrator™-25 kit (Zymo Research, Irvine, Calif., USA) according to manufacturer's instructions.

Transformation to SUC-1029 in Order to Construct Strain SUC-1112

Yeast transformation was done by a method known by persons skilled in the art. *S. cerevisiae* strain SUC-1029 was transformed with purified PCR fragments 1 to 8 and PCR fragment 113. PCR fragments 2 to 8 contained overlaps at their 5' and 3' ends and PCR fragments 1 and 113 at their 3' and 5' end respectively, such that this allowed homologous recombination of all eight PCR fragments. The 5' end of PCR fragment 1 and the 3' end of PCR fragment 113 were homologous to the INT59 locus and enabled integration of all nine PCR fragments in the INT59 locus (see FIG. 2). This resulted in one linear fragment consisting of PCR fragments 2 to 8 integrated in the INT59 locus. This method of integration is described in patent application WO2013076280. The INT59 locus is located at chromosome XI, 923 bp downstream of YKR092C and 922 bp upstream of YKR093W.

Transformation mixtures were plated on YEPh-agar (per liter: 10 grams yeast extract, 20 grams PhytonePeptone, 20 grams agar) containing 20 grams galactose per liter and 200 µg G418 (Sigma Aldrich, Zwijndrecht, The Netherlands) per ml. After three days of growth at 30° C., individual transformants were re-streaked on YEPh—agar plates containing 20 grams galactose per liter and 200 µg G418 per ml. Presence of all introduced genes was confirmed by using PCR using primer sequences that can anneal to the coding sequences of the ORF's encoded by SEQ ID NO: 1 to SEQ ID NO: 7. The resulting strain was named SUC-1112. The KanMX marker, present in strain SUC-1112, can be removed if required.

Example 3: Transformation of a Malate Dehydrogenase Gene to Strain SUC-1112 and Production of Malic Acid in Resulting Transformants Generation of PCR Fragments Primer sequences described in SEQ ID NO: 25 and SEQ ID NO: 26 were used to generate PCR fragment 13 consisting of the 5' INT1 integration site, using genomic DNA of strain CEN.PK 113-7D as template.

PCR fragment 114 was generated by using the primer sequences described in SEQ ID NO: 43 and SEQ ID NO: 44, using SEQ ID NO: 42 as template. SEQ ID NO: 42 contains the ZWF1 gene, encoding Glucose-6-phosphate dehydrogenase (G6PD). This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *Kluyveromyces lactis*, i.e. the promoter of ORF KLLA0C05566g (uniprot accession number Q6CUE2) controls the expression of the ZWF1-gene. Proper termination is controlled by a terminator sequence from *S. cerevisiae*, i.e. the TEF1-terminator.

PCR fragment 115 was generated by using the primer sequences described in SEQ ID NO: 45 and SEQ ID NO: 28, using SEQ ID NO: 38 as template. SEQ ID NO: 38 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 February; 73(4):1126-35. Epub 2006 Dec. 1) and in which the KanMX marker was replaced by a nourseothricin marker (Goldstein and McCusker, Yeast. 1999 October; 15(14):1541-53).

PCR fragment 15 was generated by using the primer sequences described in SEQ ID NO: 29 and SEQ ID NO: 30, using SEQ ID NO: 31 as template. SEQ ID NO: 31 encodes malate dehydrogenase (MDH3) from *S. cerevisiae*. MDH3 is altered by the deletion of the SKL carboxy-terminal sequence as disclosed in patent application WO2013/004670 A1. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the TDH3-promoter controls the expression of the MDH3-gene. Proper termination is controlled by a terminator sequence from *S. cerevisiae*, i.e. the GPM1-terminator.

Primer sequences described in SEQ ID NO: 32 and SEQ ID NO: 33 were used to generate PCR fragment 16 consisting of the 3' INT1 integration site, using genomic DNA of strain CEN.PK 113-7D as template.

PCR fragments 13 to 16 were purified using the DNA Clean & Concentrator™-25 kit (Zymo Research, Irvine, Calif., USA) according to manufacturer's instructions.
Transformation to SUC-1112

Yeast transformation was done by a method known by persons skilled in the art. *S. cerevisiae* strain SUC-1112 was transformed with purified PCR fragments 13, 114, 115, 15 and 16. PCR fragments 114 and 115 and 15 contained overlaps at their 5' and 3' ends and PCR fragments 13 and 16 contained overlaps at their 3' and 5' end respectively, such that this allowed homologous recombination of all five PCR fragments. The 5' end of PCR fragment 13 and the 3' end of PCR fragment 16 were homologous to the INT1 locus and enabled integration of all four PCR fragments in the INT1 locus (see FIG. 3). This resulted in one linear fragment consisting of PCR fragments 13 to 16 integrated in the INT1 locus. This method of integration is described in patent application WO2013/076280. The INT1 locus is located at chromosome XV, 659 bp downstream of YOR071c and 998 bp upstream of YOR070c. This approach resulted in expression of the malate dehydrogenase protein of 340 amino acids as indicated in SEQ ID NO: 39 which lacks the C-terminal amino acid SKL as compared to the native sequence from *S. cerevisiae*.

Transformation mixtures were plated on YEPh-agar (per liter: 10 grams yeast extract, 20 grams PhytonePeptone, 20 grams agar)) containing 20 grams galactose per liter and 200 μg nourseothricin (Jena Bioscience, Germany) per ml. After three days of growth at 30° C., individual transformants were re-streaked on YEPh-agar plates containing 20 grams galactose per liter and 200 μg nourseothricin per ml. Presence of the introduced genes was confirmed by using PCR using primer sequences that can anneal to the coding sequences of the ORF's encoded present on PCR fragment 114, 115 and 15. To confirm integration of PCR fragments 13, 114, 115, 15 and 16 on the correct locus, primers annealing to the region 5' and 3' of the INT1 locus, not binding to the INT1 regions on PCR fragments 13 and 16 were used in combination with primers annealing to the ORF's on PCR fragments 114 and 15 such that only PCR product can be formed if PCR fragments 114 and 15 are integrated in the INT1 locus. Three resulting individual colonies SUC-1112+MDH3#1, SUC-1112+MDH3#2, SUC-1112+MDH3#3. The KanMX and nourseothricin markers, present in strains SUC-1112+MDH3#1, SUC-1112+MDH3#2, SUC-1112+MDH3# can be removed if required.
Dicarboxylic Acid Production To determine dicarboxylic acid production MTP fermentations and NMR measurements were performed as described in General Materials and Methods.
In the supernatant of the SUC-1112+MDH3 strains, SUC-1112+MDH3#1, SUC-1112+MDH3#2, SUC-1112+MDH3#3, which contain an additional copy of the MDH3 gene, present on PCR fragment 15, an average titer of 8.7 g/L malic acid was measured. Succinic acid levels were lower than expected; the strains appeared to have lost the FRDg gene resulting in limited conversion of malate to succinate.

Example 4: Transformation of Genes Encoding Malate Dehydrogenase Mutants to Strain SUC-1112 and Production of Malic Acid in Resulting Transformants Generation of PCR Fragments PCR fragments 13 and 16 were generated as described in Example 3.

PCR fragment 14 was generated by using the primer sequences described in SEQ ID NO: 27 and SEQ ID NO: 28, using SEQ ID NO: 38 as template. SEQ ID NO: 38 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 February; 73(4):1126-35. Epub 2006 Dec. 1) and in which the KanMX marker was replaced by a nourseothricin marker (Goldstein and McCusker, Yeast. 1999 October; 15(14):1541-53).

Synthetic nucleotide sequences encoding different protein mutants of the reference malate dehydrogenase sequence that is described in SEQ ID NO: 39 were synthesized by DNA 2.0 (Menlo Park, Calif., USA). The synthetic nucleotide sequences encode a mutant amino acid sequence at positions 34 to 40 relative to the reference MDH3 sequence (SEQ ID NO: 39) as indicated in Table 1. Apart from encoding the indicated mutant amino acids in Table 1 the synthetic nucleotide sequence mutants are identical to SEQ ID NO: 31 The synthetic gene is under control of (or operable linked to) a promoter from *S. cerevisiae*, i.e. the TDH3-promoter controls the expression of the mutant MDH-gene. Proper termination is controlled by a terminator sequence from *S. cerevisiae*, i.e. the GPM1-terminator.

The synthetic gene sequences containing amongst others a TDH3 promoter—mutant MDH—GPM1 terminator and were amplified by PCR using the primer sequences described in SEQ ID NO: 29 and SEQ ID NO: 30, to generate PCR fragments 17 to 108 (see Table 1).

PCR fragments 13, 14, 16 and 17 to 108 were purified using the DNA Clean & Concentrator™-25 kit (Zymo Research, Irvine, Calif., USA) according to manufacturer's instructions.
Transformation to SUC-1112

Strain SUC-1112 was transformed with purified PCR fragments 13, 14 and 16 in combination with PCR fragments 17 to 108 individually. PCR fragment 14 and PCR fragments 17 to 108 contained overlaps at their 5' and 3' ends and PCR fragments 13 and 16 contained overlaps at their 3' and 5' end respectively, such that this allowed homologous recombination of all four PCR fragments. The 5' end of PCR fragment 13 and the 3' end of PCR fragment 16 were homologous to the INT1 locus and enabled integration of all four PCR fragments in the INT1 locus (FIG. 4). Transformation and selection of transformants is described in Example 2.
Dicarboxylic Acid Production To determine dicarboxylic acid production, four independent SUC-1112 transformants expressing mutant malate dehydrogenase sequences were grown in micro titer plates as described in General Materials and Methods. Low amounts of succinic acid were produced due to the loss of FRDg (see Example 3), but MDH3 activity could still be determined by measuring malate levels. Average malic acid titers are depicted in Table 1. The average production of malic acid of several SUC-1112 transformants expressing mutant malate dehydrogenase sequences exceeded 10 g/L malic acid. Interestingly, mutants with a substitution of aspartic acid by a glycine or serine residue at position 34 show increased malate production. This is significantly more than the average malic acid titer of SUC-1112 transformed with the reference MDH3 sequence described in Example 3. By significantly more it is meant that the 95% confidence intervals of malic titers for strains with reference and improved mutant malate dehydrogenase sequences do not overlap. The upper limit of the 95% confidence interval for the malic acid titer of SUC-1112 transformed with the reference MDH3 sequence lies below 10 g/L.

TABLE 1

Average malic acid titers measured in the supernatant of production medium after 4 days cultivation of transformants of strain SUC-1112, expressing phosphoenolpyruvate carboxykinase (PCKa), pyruvate carboxylase (PYC2), malate dehydrogenase (MDH3), fumarase (FUMR and fumB), dicarboxylic acid transporter (DCT 02), and transformed with the nucleotide sequence encoding the reference malate dehydrogenase (SEQ ID NO: 39) or a malate dehydrogenase mutant (MUT 001-MUT 94), which contains mutations as compared to the reference sequence in the amino acid positions indicated below.

| PCR frag-ment | Clone | Loop sequence (amino acid position) | | | | | | | Average malic acid titer (g/L) |
|---|---|---|---|---|---|---|---|---|---|
| | | 34 | 35 | 36 | 37 | 38 | 39 | 40 | |
| 15 | SUC-1112 + MDH3 reference | D | I | R | A | A | E | G | 8.7 g/L |
| 17 | MUT_001 | D | I | Q | A | A | E | G | 9.0 |
| 18 | MUT_002 | D | I | S | A | A | E | G | 9.1 |
| 19 | MUT_003 | D | S | R | A | A | E | G | 9.0 |
| 20 | MUT_004 | D | S | Q | A | A | E | G | 9.7 |
| 21 | MUT_005 | D | S | S | A | A | E | G | 9.8 |
| 22 | MUT_006 | S | I | R | A | A | E | G | 10.1 |
| 23 | MUT_007 | S | I | Q | A | A | E | G | 11.7 |
| 24 | MUT_008 | S | I | S | A | A | E | G | 17.1 |
| 25 | MUT_009 | S | S | R | A | A | E | G | 16.1 |
| 26 | MUT_010 | S | S | Q | A | A | E | G | 16.4 |
| 27 | MUT_011 | S | S | S | A | A | E | G | 16.5 |
| 28 | MUT_012 | G | I | R | A | A | E | G | 16.6 |
| 29 | MUT_013 | G | I | Q | A | A | E | G | 16.2 |
| 30 | MUT_014 | G | I | S | A | A | E | G | 16.5 |
| 31 | MUT_015 | G | S | R | A | A | E | G | 15.8 |
| 32 | MUT_016 | G | S | Q | A | A | E | G | 16.5 |
| 33 | MUT_017 | G | S | S | A | A | E | G | 15.9 |
| 34 | MUT_018 | D | I | A | V | T | P | G | 9.1 |
| 35 | MUT_019 | D | I | A | N | V | K | G | 9.0 |
| 36 | MUT_020 | D | I | R | N | V | K | G | 9.2 |
| 37 | MUT_021 | D | I | Q | N | V | K | G | 9.2 |
| 38 | MUT_022 | D | I | S | N | V | K | G | 8.8 |
| 39 | MUT_023 | D | S | A | N | V | K | G | 9.3 |
| 40 | MUT_024 | D | S | R | N | V | K | G | 9.3 |
| 41 | MUT_025 | D | S | Q | N | V | K | G | 8.4 |
| 42 | MUT_026 | D | S | S | N | V | K | G | 9.3 |
| 43 | MUT_027 | S | I | A | N | V | K | G | 15.4 |
| 44 | MUT_028 | S | I | R | N | V | K | G | 14.4 |
| 45 | MUT_029 | S | I | Q | N | V | K | G | 11.7 |
| 46 | MUT_030 | S | I | S | N | V | K | G | 16.1 |
| 47 | MUT_031 | S | S | A | N | V | K | G | 15.8 |
| 48 | MUT_032 | S | S | R | N | V | K | G | 15.8 |
| 49 | MUT_033 | S | S | Q | N | V | K | G | 15.7 |
| 50 | MUT_034 | S | S | S | N | V | K | G | 16.1 |
| 51 | MUT_035 | G | I | A | N | V | K | G | 15.7 |
| 52 | MUT_036 | G | I | R | N | V | K | G | 14.2 |
| 53 | MUT_037 | G | I | Q | N | V | K | G | 9.5 |
| 54 | MUT_038 | G | I | S | N | V | K | G | 16.6 |
| 55 | MUT_039 | G | S | A | N | V | K | G | 11.8 |
| 56 | MUT_040 | G | S | R | N | V | K | G | 14.4 |
| 57 | MUT_041 | G | S | Q | N | V | K | G | 15.4 |
| 58 | MUT_042 | G | S | S | N | V | K | G | 15.9 |
| 59 | MUT_043 | D | I | A | G | T | P | G | 8.3 |
| 60 | MUT_044 | D | I | R | G | T | P | G | 7.6 |
| 61 | MUT_045 | D | I | Q | G | T | P | G | 7.9 |
| 62 | MUT_046 | D | I | S | G | T | P | G | 8.5 |
| 63 | MUT_047 | D | S | A | G | T | P | G | 8.4 |
| 64 | MUT_048 | D | S | R | G | T | P | G | 8.4 |
| 65 | MUT_049 | D | S | Q | G | T | P | G | 8.7 |
| 66 | MUT_050 | D | S | S | G | T | P | G | 7.4 |
| 67 | MUT_051 | S | I | A | G | T | P | G | 9.7 |
| 68 | MUT_052 | S | I | R | G | T | P | G | 11.3 |
| 69 | MUT_053 | S | I | Q | G | T | P | G | 13.8 |
| 70 | MUT_054 | S | I | S | G | T | P | G | 13.4 |
| 71 | MUT_055 | S | S | A | G | T | P | G | 14.4 |
| 72 | MUT_056 | S | S | R | G | T | P | G | 13.9 |
| 73 | MUT_057 | S | S | Q | G | T | P | G | 14.2 |
| 74 | MUT_058 | S | S | S | G | T | P | G | 14.2 |
| 75 | MUT_059 | G | I | A | G | T | P | G | 13.9 |
| 76 | MUT_060 | G | I | R | G | T | P | G | 13.5 |
| 77 | MUT_061 | G | I | Q | G | T | P | G | 13.7 |
| 78 | MUT_062 | G | I | S | G | T | P | G | 14.2 |
| 79 | MUT_063 | G | S | A | G | T | P | G | 14.7 |
| 80 | MUT_064 | G | S | R | G | T | P | G | 11.8 |
| 81 | MUT_065 | G | S | Q | G | T | P | G | 14.4 |
| 82 | MUT_066 | G | S | S | G | T | P | G | 14.4 |
| 83 | MUT_067 | D | I | E | R | S | F | Q | 6.5 |
| 84 | MUT_068 | D | I | E | R | S | F | G | 6.4 |
| 85 | MUT_069 | D | I | E | A | S | F | Q | 8.6 |
| 86 | MUT_070 | D | I | E | A | S | F | G | 8.3 |
| 87 | MUT_071 | D | S | E | R | S | F | Q | 7.6 |
| 88 | MUT_072 | D | S | E | R | S | F | G | 8.5 |
| 89 | MUT_073 | D | S | E | A | S | F | Q | 6.9 |
| 90 | MUT_074 | D | S | E | A | S | F | G | 8.0 |
| 91 | MUT_075 | S | I | E | R | S | F | Q | 9.7 |
| 92 | MUT_076 | S | I | E | R | S | F | G | 15.1 |
| 93 | MUT_077 | S | I | E | A | S | F | Q | 7.8 |
| 94 | MUT_078 | S | I | E | A | S | F | G | 13.7 |
| 95 | MUT_079 | S | S | E | R | S | F | Q | 14.1 |
| 96 | MUT_080 | S | S | E | R | S | F | G | 14.1 |
| 97 | MUT_081 | S | S | E | A | S | F | Q | 12.2 |
| 98 | MUT_082 | S | S | E | A | S | F | G | 13.9 |
| 99 | MUT_083 | G | I | E | R | S | F | Q | 9.3 |
| 100 | MUT_084 | G | I | E | R | S | F | G | 14.0 |
| 101 | MUT_085 | G | I | E | A | S | F | Q | 6.3 |
| 102 | MUT_086 | G | I | E | A | S | F | G | 12.2 |
| 103 | MUT_087 | G | S | E | R | S | F | Q | 14.0 |
| 104 | MUT_088 | G | S | E | R | S | F | G | 15.9 |
| 105 | MUT_089 | G | S | E | A | S | F | Q | 14.0 |
| 106 | MUT_090 | G | S | E | A | S | F | G | 14.5 |
| 107 | MUT_091 | D | I | P | Q | A | L | G | 7.6 |
| 108 | MUT_092 | D | S | P | Q | A | L | G | 7.3 |
| 109 | MUT_093 | S | S | P | Q | A | L | G | 14.2 |
| 110 | MUT_094 | G | S | P | Q | A | L | G | 16.0 |

Example 5: Measuring NADH and NADPH Specific Activity of Malate Dehydrogenase Mutants A total of 19 mutants were selected from Table 1 and re-cultured as described in General materials and methods. The biomass was harvested by centrifugation (4000 rpm, 10 min, 4° C.) and washed twice with PBS (phosphate buffered saline, Sigma Aldrich) after which the cell pellets were frozen at −20° C. Cell disruption was achieved in square welled 96-deepwell micro titer plates (MTP) using 0.5 mm acid washed glass beads in combination with the TissueLyser II from Qiagen (3000 rpm for 2×10 sec, cool on ice for 1 min between cycles). Glass beads taking up a volume of 600 µl were added to the cell pellet before addition of 1 ml in vivo like-assay medium (described in van Eunen et al. FEBS *Journal* 1277: 749-760 adapted to contain 0.5 mM DTT (dithiothreitol, Sigma-Aldrich) and 0.1 mM PMSF (phenylmethanesulfonyl fluoride, Amresco). Glass beads were added by inverting the deep well MTP containing the frozen pellets over a standard MTP where each well is filled completely with glass beads (=a volume of 300 µl) and then inverting both plates, so that the glass beads fall onto the cell pellets. This process was repeated to obtain 600 µl glass beads in the cell pellets. Next 1 ml of in vivo like-assay medium described above was added. After cell disruption, cell debris was pelleted by centrifugation (4000 rpm, 30 min, 4° C.). The supernatant (soluble cell extracts) were collected and stored on ice. Protein concentration of the extracts was determined by Bradford, using bovine serum albumin (BSA) as standard.

Malate dehydrogenase (MDH) activity was assayed spectrophotometrically by following the decrease in absorbance at 340 nm caused by the oxidation of NADH or NADPH to NAD+ or NADP+, respectively. Assays contained 400 µM NADH or 400 µM NADPH, 2 mM oxaloacetic acid (Sigma Aldrich) and approximately 0.0625 mg protein ml$^{-1}$ soluble cell extracts in in vivo-like assay medium. Assays were performed in a final volume of 200 µl. Equal volume of soluble cell extracts were added in both the NADH and NADPH dependent assays. Reactions were started by the addition of 100 µl oxaloacetic acid stock solution (4 mM) and were followed for 9 minutes at 30 degrees Celsius and the slope was used as a measure of NADH or NADPH dependent MDH activity. The slope (in Δ A340/min) was determined with the 'slope' function in Microsoft Excel where the absorbance values were taken as 'y' values and the time in minutes as 'x' values. The 'RSQ' function in Microsoft Excel was used to check the quality of the slope fitting (criteria>0.9). The slope was corrected for the slope of blank reaction containing in vivo-like assay medium instead of substrate. Absorbance was measured using a Tecan Infinite M1000 plate reader. NADH dependent activity of each mutant was compared to the NADPH activity. The ratio of NADPH:NADH dependent activity or NADPH:NADH specificity ratio, was determined by:

1) Determining the slope (in Δ A340/min) of the NADPH-dependent MDH activity
2) Determining the slope (in Δ A340/min) NADH-dependent MDH activity
3) Dividing the slope of the NADPH-dependent MDH activity by the slope of the NADH-dependent MDH activity.
To determine the ratio, slopes were used without normalization for amount of total protein as equal volumes of each mutant were used in the NADH and NADPH dependent MDH activity assays, The ratio was calculated for 19 mutants (FIG. 5D). An increased value for the ratio compared to the reference indicated that the cofactor specificity has been changed.

Supernatants of the 19 cultured mutants and the reference strain were analysed for malic acid titers as described in general materials and methods. The NADPH-specific and NADH-specific activities were measured as described above and normalized for total protein by dividing by the total protein concentration in the assay. The results are shown in FIGS. 5B-5C. Clearly, the 19 selected mutants have an enhanced NADPH-specific malate dehydrogenase activity. For most of the 19 mutants the NADH-specific malate dehydrogenase activity is decreased compared to the reference (FIG. 5B). Interestingly, in 6 mutants, the NADH-specific activity is increased (FIG. 5B), indicating that in these mutants both the NADH-specific activity and NADPH-specific activity is increased. In all mutants, the NADPH:NADH specificity ratio was increased (FIG. 5D).

Figure 5A:
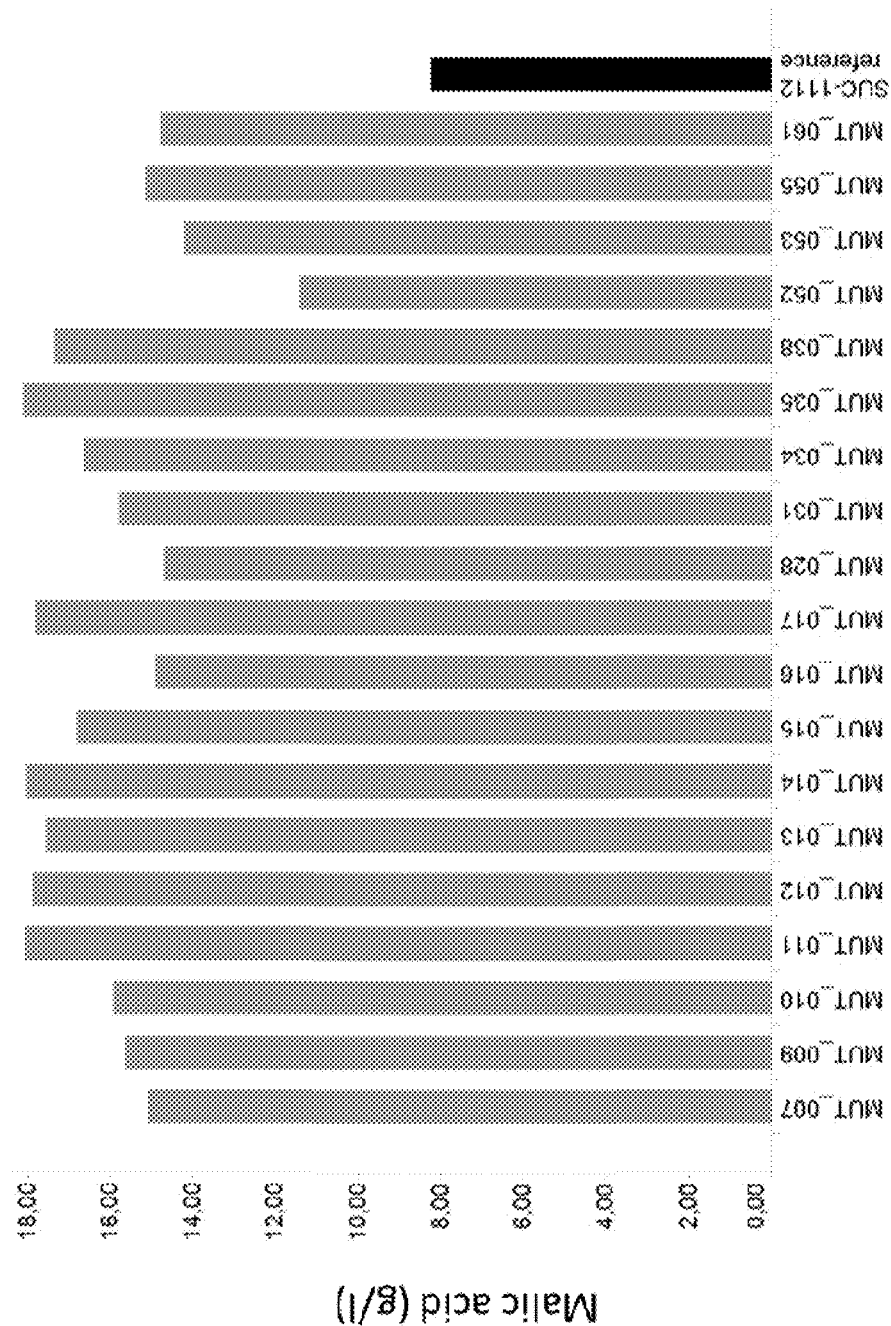
FIG. 5A: Average malic acid titers measured in the supernatant of production medium after cultivation of SUC-1112 transformants, expressing phosphoenolpyruvate carboxykinase (PCKa), pyruvate carboxylase (PYC2), malate dehydrogenase (MDH3), fumarase (FUMR and fumB), dicarboxylic acid transporter (DCT_02) and transformed with reference malate dehydrogenase (SEQ ID NO: 39) or mutant malate dehydrogenase, which contains mutations as compared to the reference sequence in the amino acid positions as indicated in Table 1. The malic acid titer was measured as described in General Materials and Methods and represents an average value obtained from three independent clones.
Figure 5D:
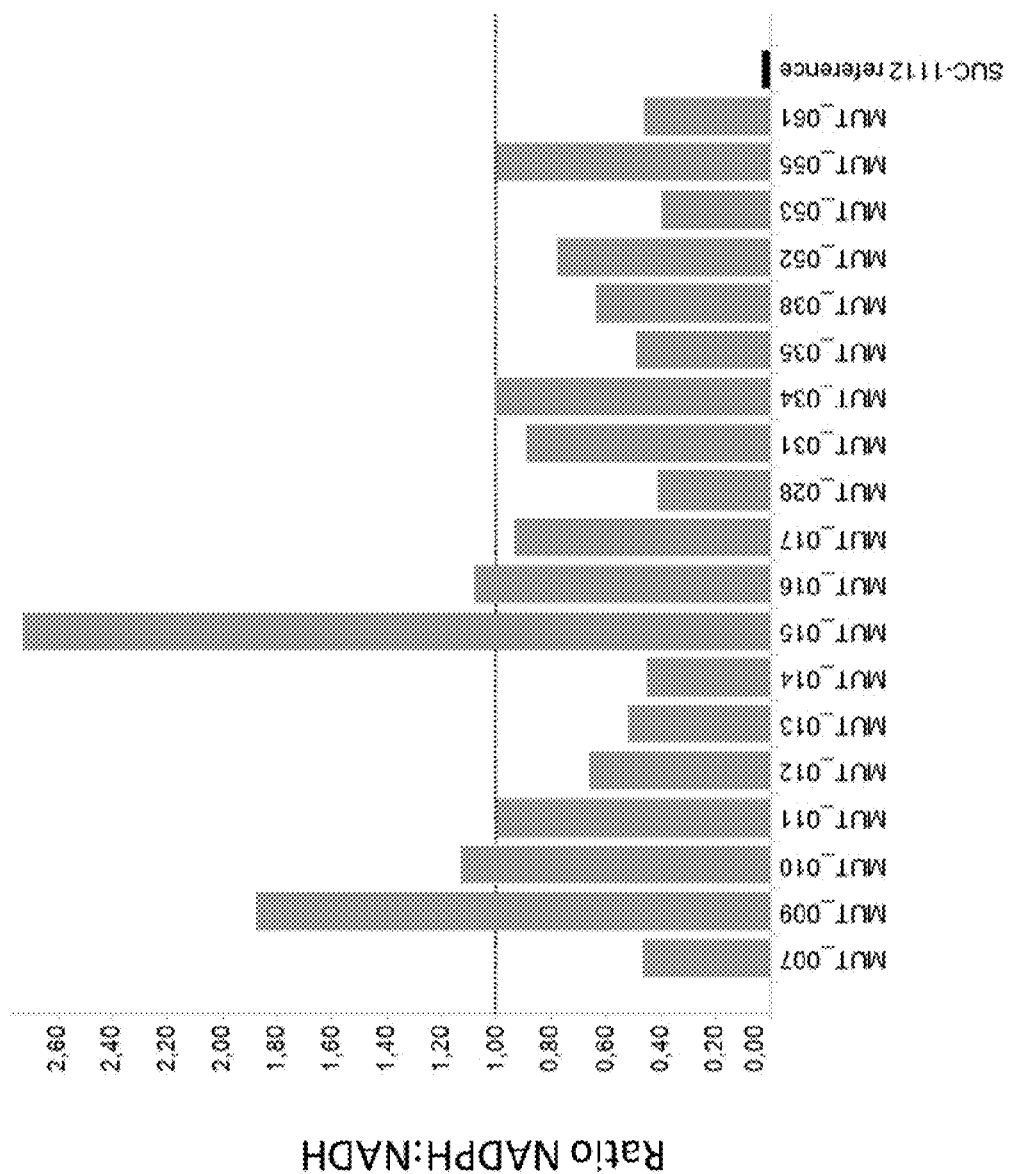
FIG. 5D: Ratio of NADPH:NADH dependent activity of MDH mutants expressed in strain SUC-1112 (see Table 1 for specific mutations). The activity was measured and the ratio was determined as described in Example 5. The dashed line indicates a NADPH:NADH ratio of 1.0.

Surprisingly, a substitution of aspartic acid by a glycine or serine residue at position 34 has a positive effect on the malic acid titer of SUC-1112 strains transformed with these malate dehydrogenase mutants (FIG. 5A).

Example 6: Construction of Strain REV-0001

Generation of PCR Fragments

Primer sequences described in SEQ ID NO: 54 and SEQ ID NO: 55 are used to generate PCR fragment 116 consisting of the 5' INT1 integration site, using genomic DNA of strain CEN.PK 113-7D as template.

PCR fragment 117 is generated by using the primer sequences described in SEQ ID NO: 56 and SEQ ID NO: 57, using SEQ ID NO: 38 as template. SEQ ID NO: 38 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 February; 73(4):1126-35. Epub 2006 Dec. 1) and in which the KanMX marker was replaced by a nourseothricin marker (Goldstein and McCusker, Yeast. 1999 October; 15(14):1541-53).

PCR fragment 118 is generated by using the primer sequences described in SEQ ID NO: 60 and SEQ ID NO: 61, using SEQ ID NO: 62 as template. SEQ ID NO: 62 encodes fumarate reductase (FRDg) from *Trypanosoma brucei*, as disclosed in patent application WO2009/065778. This synthetic sequence, which includes promoter-gene-terminator sequence, including appropriate restriction sites, is synthesized by DNA 2.0 (Menlo Park, Calif., USA). The gene sequence is codon pair optimized for expression in *S. cerevisiae* as disclosed in patent application WO2008/000632. The synthetic gene is under control of (or operable linked to) a promoter from *S. cerevisiae*, i.e. the TDH3-promoter controls the expression of the FRDg-gene. Proper termination is controlled by a terminator sequence from *S. cerevisiae*, i.e. the TAL1-terminator. Primer sequences described in SEQ ID NO: 58 and SEQ ID NO: 59 are used to generate PCR fragment 119 consisting of the 3' INT1 integration site, using genomic DNA of strain CEN.PK 113-7D as template.

PCR fragments 116 to 119 are purified using the DNA Clean & Concentrator™-25 kit (Zymo Research, Irvine, Calif., USA) according to manufacturer's instructions.

Transformation of SUC-1029

Yeast transformation is performed by a method known by persons skilled in the art. *S. cerevisiae* strain SUC-1029 (Example 1) is transformed with purified PCR fragments 116 to 119. PCR fragments 117 and 118 contain overlaps at their 5' and 3' ends and PCR fragments 116 and 119 contain overlaps at their 3' and 5' end respectively, such that this allows homologous recombination of all four PCR fragments. The 5' end of PCR fragment 116 and the 3' end of PCR fragment 119 are homologous to the INT1 locus and enables integration of all four PCR fragments in the INT1 locus (see FIG. 6). This results in one linear fragment consisting of PCR fragments 116 to 119 integrated in the INT1 locus. This method of integration is described in patent application WO2013076280. The INT1 locus is located at chromosome XV, 659 bp downstream of YOR071c and 998 bp upstream of YOR070c. This approach results in expression of the fumarate reductase protein of 1139 amino acids as indicated in SEQ ID NO: 8, which lacks the C-terminal amino acid SKI as compared to the native sequence from *T. brucei*.

Transformation mixtures are plated on YEPh-agar (per liter: 10 grams yeast extract, 20 grams PhytonePeptone, 20 grams galactose, 20 grams agar)) containing 100 µg nourseothricin (Jena Bioscience, Germany) per ml. After three days of growth at 30° C., individual transformants are re-streaked on YEPh-agar plates containing 20 grams galactose per liter and 100 µg nourseothricin per ml. Presence of the introduced genes is confirmed by using PCR using primer sequences that can anneal to the coding sequences of the ORF's encoded by SEQ ID NO: 38 and SEQ ID NO: 62.

Example 7: Transformation of Genes Encoding Malate Dehydrogenase Mutants to Strain REV-0001 and Production of Succinic Acid in Resulting Transformants In order to determine if succinate levels are increased in strains expressing MDH mutants, MDH mutants are introduced in strain REV-0001 in which FRDg is expressed (Example 6). Based on the malic acid production results (Example 4) and the in vitro activity assay results (Example 5), 3 MDH mutants are selected: MUT_014, MUT_015 and MUT_034.

Generation of PCR Fragments

The amplification of PCR fragment 1, 2, 3, 4 and 5 is described in Example 2. In order to introduce the wild-type and diverse MDH mutants, PCR fragment 120 (wild-type MDH3, SEQ ID NO: 31), fragment 121 (MUT_014, SEQ ID NO: 64), fragment 122 (MUT_015, SEQ ID NO: 65) or fragment 123 (MUT_034, SEQ ID NO: 66) are used. The wild-type and mutant MDH3 genes are driven by the *S. cerevisiae* TDH3 terminator and termination is controlled by the *S. cerevisiae* GPM1 terminator. The cassettes are amplified by PCR using the primer sequences described in SEQ ID NO: 19 and SEQ ID NO: 20, to generate PCR fragments 120 to 123.

Primer sequences described in SEQ ID NO: 63 and SEQ ID NO: 41 are used to generate PCR fragment 124 consisting of the 3' INT59 integration site, using genomic DNA of strain CEN.PK 113-7D as template.

PCR fragments 1 to 5/120-123 and PCR fragment 124 are purified using the DNA Clean & Concentrator™-25 kit (Zymo Research, Irvine, Calif., USA) according to manufacturer's instructions.

Transformation to REV-0001

Yeast transformation is performed by a method known by persons skilled in the art. *S. cerevisiae* strain REV-0001 is transformed with purified PCR fragments 1 to 5 and 124 in combination with PCR fragments 120, 121, 122 or 123. PCR fragments 2 to 5/120-123 contain overlaps at their 5' and 3' ends and PCR fragments 1 and 124 at their 3' and 5' end respectively, such that this allows homologous recombination of all seven PCR fragments. The 5' end of PCR fragment 1 and the 3' end of PCR fragment 124 are homologous to the INT59 locus and enable integration of all seven PCR fragments in the INT59 locus (see FIG. 7). This results in one linear fragment consisting of PCR fragments 2 to 5/120-123 integrated in the INT59 locus. This method of integration is described in patent application WO2013076280. The INT59 locus is located at chromosome XI, 923 bp downstream of YKR092C and 922 bp upstream of YKR093W. Transformation mixtures are plated on YEPh-agar (per liter: 10 grams yeast extract, 20 grams PhytonePeptone, 20 grams agar) containing 20 grams galactose per liter and 200 µg G418 (Sigma Aldrich, Zwijndrecht, The Netherlands) per ml. After three days of growth at 30° C., individual transformants are re-streaked on YEPh—agar plates containing 20 grams galactose per liter and 200 µg G418 per ml. Presence of all introduced genes is confirmed by PCR.

Dicarboxylic Acid Production

To determine dicarboxylic acid production, REV-0001-derived transformants expressing the succinic acid production pathway with either wild-type MDH3 or individual MDH mutants are grown in micro titer plates and dicarboxylic acid concentrations are determined as described in General Materials and Methods.

Succinic acid titers of strains expressing MUT_014, MUT_015 and MUT_34 are respectively 1.3-, 1.2 and 1.4-fold higher than strains expressing MDH3, indicating that succinic acid production is also improved in strains expressing MDH mutants.

The invention claimed is:

1. A recombinant fungal host cell comprising a nucleic acid sequence encoding a mutant polypeptide having malate dehydrogenase activity, wherein the mutant polypeptide comprises an amino acid sequence which, when aligned with the malate dehydrogenase comprising the sequence set out in SEQ ID NO: 39, comprises a mutation of an amino acid residue corresponding to amino acid 34 in SEQ ID NO: 39, wherein the mutant polypeptide has at least 70% identity with SEQ ID NO: 39 or SEQ ID NO: 53, wherein the mutant polypeptide is expressed in the cytosol of the host cell, and wherein the host cell produces increased dicarboxylic acid compared to a recombinant host cell that expresses SEQ ID NO: 39 cultured under the same conditions.

2. A recombinant host cell according to claim 1, wherein the mutation of the amino acid residue corresponding to amino acid 34 in SEQ ID NO: 39 is a substitution to a small amino acid.

3. A recombinant host cell according to claim 1, wherein the mutation of the amino acid residue corresponding to amino acid 34 in SEQ ID NO: 39 is selected from the group of substitutions corresponding to 34G and 34S.

4. A recombinant host cell according to claim 1, wherein the mutant polypeptide having malate dehydrogenase activity further comprises a mutation of an amino acid residue corresponding to amino acid 36 in SEQ ID NO: 39.

5. A recombinant host cell according to claim 4, wherein the mutation of the amino acid residue corresponding to amino acid 36 in SEQ ID NO: 39 is selected from the group of substitutions corresponding to 36R, 36Q, 36A, 36E, 36P and 36S.

6. A recombinant host cell according to claim 3, wherein the recombinant host cell produces from between about 9.3 and 17 g/L of malic acid.

7. The recombinant host cell according to claim 1 wherein the mutant polypeptide has an increase in the NADP(H)- relative to NAD(H)-dependent activity as compared to that of SEQ ID NO: 39.

8. A recombinant host cell according to claim 7, wherein the NAD(H)- and NADP(H)-dependent activities of the mutant polypeptide having malate dehydrogenase activity are both increased.

9. A recombinant host cell according to claim 1, wherein the mutant polypeptide having malate dehydrogenase activity is a mutant NAD(H)-dependent malate dehydrogenase (EC 1.1.1.37).

10. A recombinant host cell according to claim 1, wherein the mutant polypeptide having malate dehydrogenase activity is a mutant peroxisomal NAD(H)-dependent malate dehydrogenase.

11. A recombinant host cell according to claim 1, wherein the mutant polypeptide having malate dehydrogenase activity is a mutant of a homologous polypeptide having malate dehydrogenase activity.

12. A recombinant host cell according to claim 1, wherein the mutant polypeptide having malate dehydrogenase activity is a mutant NAD(H)-dependent malate dehydrogenase from a yeast.

13. A recombinant host cell according to claim 1, wherein the recombinant host cell is a yeast cell selected from the group consisting of *Candida, Hansenula, Kluyveromyces, Pichia, Issatchenkia, Saccharomyces, Schizosaccharomyces,* or *Yarrowia* strains, or a filamentous fungal cell selected from the group consisting of filamentous fungal cells belong to a genus of *Acremonium, Aspergillus, Chrysosporium, Myceliophthora, Penicillium, Talaromyces, Rasamsonia, Thielavia, Fusarium* or *Trichoderma*.

14. A recombinant host cell according to claim 13, wherein the yeast cell is *Saccharomyces cerevisiae*.

15. A recombinant host cell according to claim 1, wherein the nucleic sequence encoding the mutant polypeptide having malate dehydrogenase activity is expressed in the cytosol and the mutant polypeptide having malate dehydrogenase activity is active in the cytosol.

16. A host cell according to claim 1, wherein the recombinant host cell further comprises one or more copies of a nucleic acid encoding one or more of a phosphoenolpyruvate carboxykinase, a phosphoenolpyruvate carboxylase, a pyruvate carboxylase, a fumarase, a fumarate reductase and/or a succinate transporter.

17. A method for production of a dicarboxylic acid, wherein the method comprises fermenting the recombinant host cell according to claim 1 under conditions suitable for production of the dicarboxylic acid.

18. A method according to claim 17, further comprising recovering the dicarboxylic acid from the fermentation medium.

19. The method according to claim 17, wherein the dicarboxylic acid is succinic acid, malic acid and/or fumaric acid.

* * * * *